United States Patent
Schaefer et al.

(10) Patent No.: US 8,362,246 B2
(45) Date of Patent: Jan. 29, 2013

(54) BISPYRIMIDINES FOR ELECTRONIC APPLICATIONS

(75) Inventors: Thomas Schaefer, Liestal (CH); Heinz Wolleb, Fehren (CH); Christian Schildknecht, Mannheim (DE); Soichi Watanabe, Mannheim (DE); Christian Lennartz, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/315,687

(22) Filed: Dec. 9, 2011

(65) Prior Publication Data
US 2012/0149904 A1 Jun. 14, 2012

Related U.S. Application Data

(60) Provisional application No. 61/422,249, filed on Dec. 13, 2010.

(51) Int. Cl.
*C07D 403/10* (2006.01)
(52) U.S. Cl. ...................................................... 544/296
(58) Field of Classification Search .................... 544/296
See application file for complete search history.

(56) References Cited

U.S. PATENT DOCUMENTS

| | | | |
|---|---|---|---|
| 8,012,602 | B2 | 9/2011 | Schäfer et al. |
| 2001/0015432 | A1 | 8/2001 | Igarashi |
| 2001/0019782 | A1 | 9/2001 | Igarashi et al. |
| 2002/0024293 | A1 | 2/2002 | Igarashi et al. |
| 2002/0048689 | A1 | 4/2002 | Igarashi et al. |
| 2002/0055014 | A1 | 5/2002 | Okada et al. |
| 2002/0094453 | A1 | 7/2002 | Takiguchi et al. |
| 2007/0190355 | A1 | 8/2007 | Ikeda et al. |
| 2007/0224446 | A1 | 9/2007 | Nakano et al. |
| 2009/0066226 | A1 | 3/2009 | Sugita et al. |
| 2009/0102356 | A1 | 4/2009 | Wang et al. |
| 2010/0109514 | A1 | 5/2010 | Schäfer et al. |
| 2010/0240892 | A1 | 9/2010 | Schäfer et al. |
| 2010/0277060 | A1 | 11/2010 | Schaefer et al. |

FOREIGN PATENT DOCUMENTS

| | | |
|---|---|---|
| EP | 0 690 053 A2 | 1/1996 |
| EP | 0 926 216 A1 | 6/1999 |
| EP | 1 191 612 A2 | 3/2002 |
| EP | 1 191 613 A2 | 3/2002 |
| EP | 1 202 608 A2 | 5/2002 |
| EP | 1 211 257 A2 | 6/2002 |
| EP | 1 724 323 A1 | 11/2006 |
| EP | 1 970 976 A1 | 9/2008 |
| EP | 1 998 388 A1 | 12/2008 |
| EP | 2 034 538 A1 | 3/2009 |
| EP | 1 885 818 B1 | 1/2010 |
| JP | 2002-324678 | 11/2002 |
| JP | 2003-45662 | 2/2003 |
| JP | 2005-255561 | 9/2005 |
| JP | 2006-321750 | 11/2006 |
| JP | 2009-21336 | 1/2009 |
| JP | 2009-184987 | 8/2009 |
| JP | 2010-135467 | 6/2010 |
| KR | 10-2009-0008737 | 1/2009 |
| WO | WO 99/47474 A1 | 9/1999 |
| WO | WO 00/70655 A2 | 11/2000 |
| WO | WO 01/41512 A1 | 6/2001 |
| WO | WO 02/02714 A2 | 1/2002 |
| WO | WO 02/15645 A1 | 2/2002 |

(Continued)

OTHER PUBLICATIONS

International Search Report and Written Opinion issued Feb. 20, 2012 in Application No. PCT/EP2011/072040.

*Primary Examiner* — Kristin Bianchi
(74) *Attorney, Agent, or Firm* — Oblon, Spivak, McClelland, Maier & Neustadt, L.L.P.

(57) ABSTRACT

The present invention relates to compounds of formula

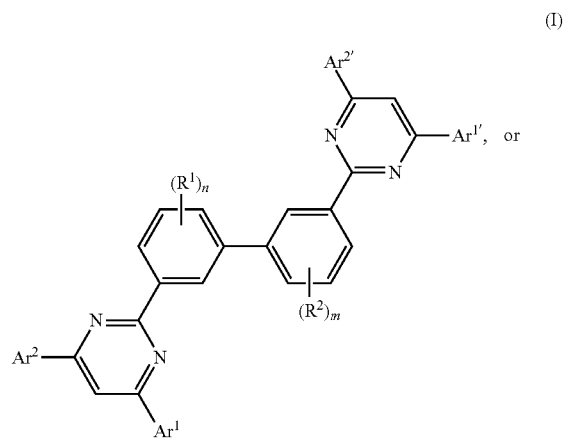

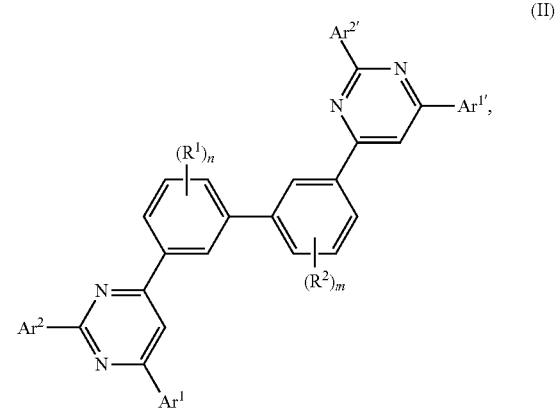

a process for their production and their use in electronic devices, especially electroluminescent devices. When used as electron transport material in electroluminescent devices, the compounds of formula I, or II may provide improved efficiency, stability, manufacturability, or spectral characteristics of electroluminescent devices.

19 Claims, No Drawings

FOREIGN PATENT DOCUMENTS

| | | | |
|---|---|---|---|
| WO | WO 02/060910 A1 | 8/2002 |
| WO | WO 2004/039786 A1 | 5/2004 |
| WO | WO 2005/019373 A2 | 3/2005 |
| WO | WO 2005/053055 A1 | 6/2005 |
| WO | WO 2005/085387 A1 | 9/2005 |
| WO | WO 2005/113704 A2 | 12/2005 |
| WO | WO 2006/056418 A2 | 6/2006 |
| WO | WO 2006/067074 A1 | 6/2006 |
| WO | WO 2006/100298 A1 | 9/2006 |
| WO | WO 2006/115301 A1 | 11/2006 |
| WO | WO 2006/121811 A1 | 11/2006 |
| WO | WO 2007/095118 A2 | 8/2007 |
| WO | WO 2007/101820 A1 | 9/2007 |
| WO | WO 2007/115970 A1 | 10/2007 |
| WO | WO 2007/115981 A1 | 10/2007 |
| WO | WO 2008/000727 A1 | 1/2008 |
| WO | WO 2008/034758 A2 | 3/2008 |
| WO | WO 2008/119666 A1 | 10/2008 |
| WO | WO 2009/003898 A1 | 1/2009 |
| WO | WO 2009/003919 A1 | 1/2009 |
| WO | WO 2009/008353 A1 | 1/2009 |
| WO | WO 2009/037155 A1 | 3/2009 |
| WO | WO 2009/054253 A1 | 4/2009 |
| WO | WO 2009/069442 A1 | 6/2009 |
| WO | WO 2009/084546 A1 | 7/2009 |
| WO | WO 2010/056669 A1 | 5/2010 |
| WO | WO 2010/079051 A1 | 7/2010 |
| WO | WO 2010/086089 A1 | 8/2010 |
| WO | WO 2010/090077 A1 | 8/2010 |
| WO | WO 2010/129323 A1 | 11/2010 |
| WO | WO 2011/073149 A1 | 6/2011 |

BISPYRIMIDINES FOR ELECTRONIC APPLICATIONS

The present invention relates to compounds of formula

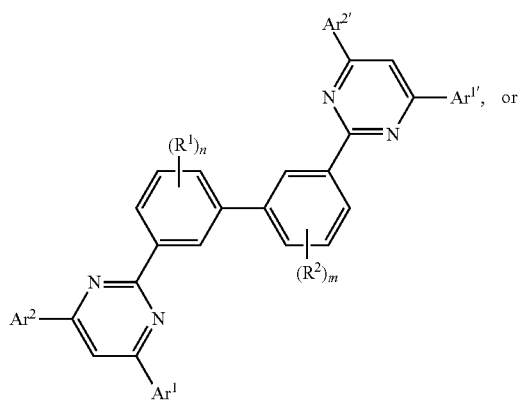

(I)

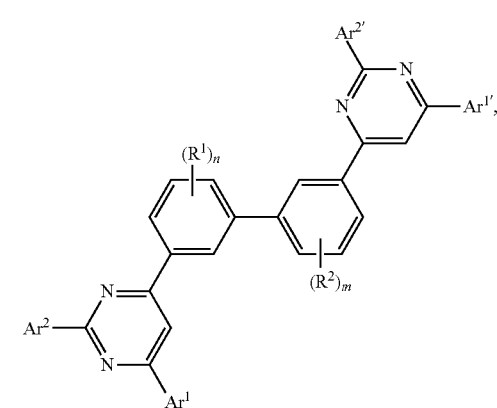

(II)

a process for their production and their use in electronic devices, especially electroluminescent devices. When used as electron transport material in electroluminescent devices, the compounds of formula I, or II may provide improved efficiency, stability, manufacturability, or spectral characteristics of electroluminescent devices.

EP-A-1,202,608 discloses EL devices comprising a carbazole compound of formula

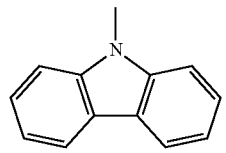

wherein R is

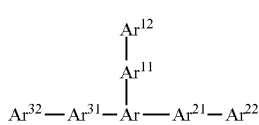

and X is C or N, which constitutes the hole transporting layer.

JP2002324678 relates to light emitting elements comprising at least one kind of compound of formula, wherein $$Ar^{32}-Ar^{31}-Ar-Ar^{21}-Ar^{22}$$
$$\overset{|}{Ar^{11}}$$
$$\overset{|}{Ar^{12}}$$

$Ar^{11}$, $Ar^{21}$ and $Ar^{31}$ denote arylene groups, $Ar^{12}$, $Ar^{22}$ and $Ar^{32}$ denote substituents or hydrogen atoms, wherein at least one of $Ar^{11}$, $A^{21}$, $A^{31}$, $A^{12}$, $A^{22}$ and $Ar^{32}$ is either a condensed ring aryl structure or a condensed ring heteroaryl structure; Ar denotes an arylene group or a heteroarylene group; and at least one amine derivative having a condensed ring group with two or more rings are contained in a luminous layer. As examples of compounds of the above formula, wherein Ar denotes a heteroarylene group the following two compounds are explicitly mentioned:

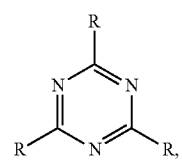

R is a group of formula

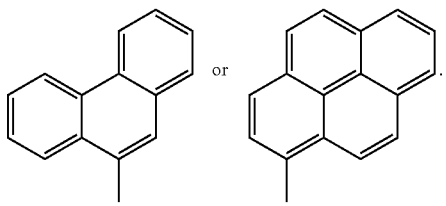

EP-A-926216 relates to EL devices using triaryl amine compounds, such as

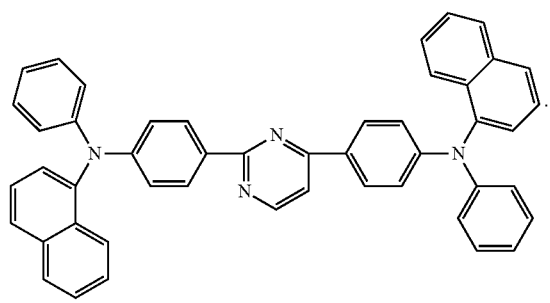 [SMILES: c1ccc(N(c2ccc(-c3ccnc(-c4ccc(N(c5ccccc5)c5cccc6ccccc56)cc4)n3)cc2)c2cccc3ccccc23)cc1]

EP-A-690 053 relates to the use of conjugated compounds containing two or more pyrimidine rings, which are part of the conjugated system, as electroluminescent materials. The conjugated compounds described in EP-A-690 053 comprise pyrimidin-2,5-diyl groups which do not carry substituents at positions 4 and 6.

Hanan, Garry S. et al., Canadian Journal of Chemistry (1997), 75(2), 169-182 disclose oligo-tridentate ligands based on alternating pyridines and pyrimidines, e.g.

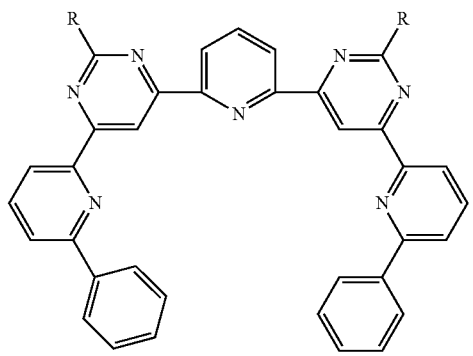

(R=H, Me, Ph), which were synthesized by Stille-type carbon-carbon bond-forming reactions. The terpyridine-like sites are designed to coalign upon metal complexation, giving rise to organized and rigidly spaced metal ions.

Shaker, Raafat M., Heteroatom Chemistry (2005), 16(6), 507-512 describes the synthesis of a series of 4,4'-(1,4-phenylene)-dipyrimidines, e.g.,

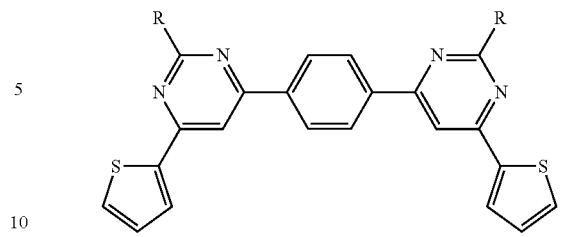

(R=Me, Ph or NH$_2$), by the reaction of amidines with the dienaminone, bis-chalcone, or ylidenemalononitrile.

JP2003045662 disclose compounds of the following formula

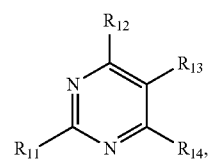
(1)

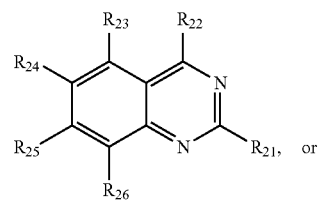
(2)

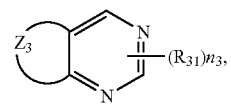
(3)

wherein $R_{11}$ to $R_{14}$ are H, or a monovalent substituent; at least one of $R_{11}$ to $R_{14}$ is an aromatic hydrocarbon group; $R_{21}$ to $R_{26}$ are H, or a monovalent substituent; $R_{31}$ is H, or a monovalent substituent; n3=0–2; $Z_3$ is a 5-membered ring.

The following "brigded" bispyrimidines are explicitly mentioned:

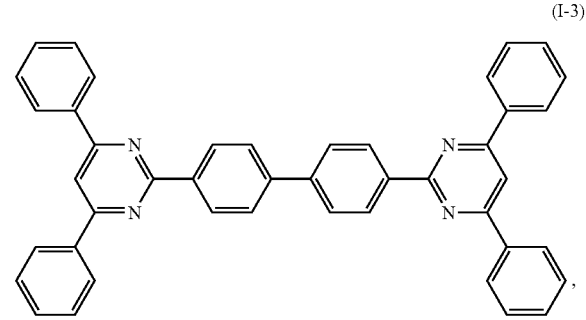
(I-3)

(II-1)
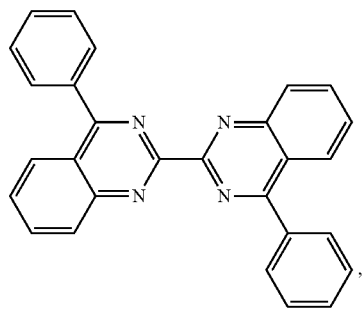,
(II-7)
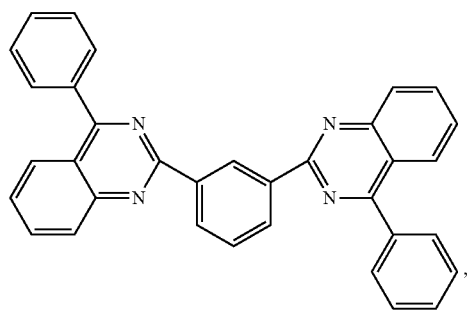,
(II-15)
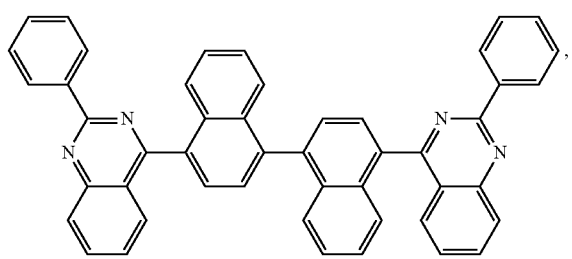,
(II-16)
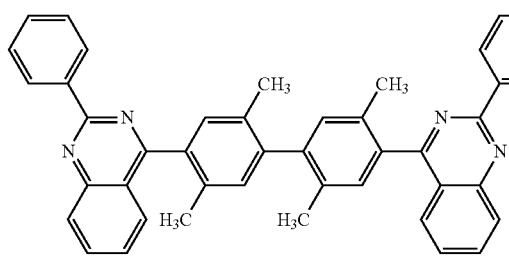,
(II-17)
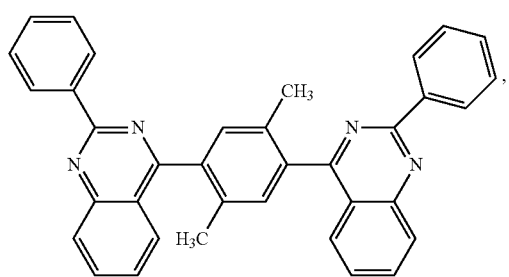,
(II-18)
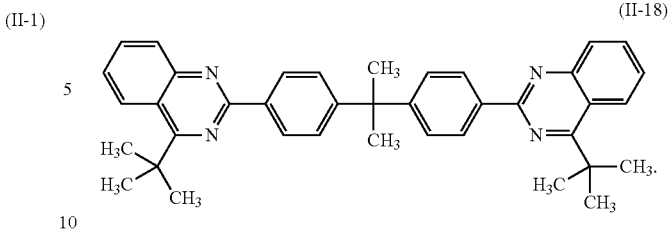.
WO04039786 discloses bispyrimidines of formula
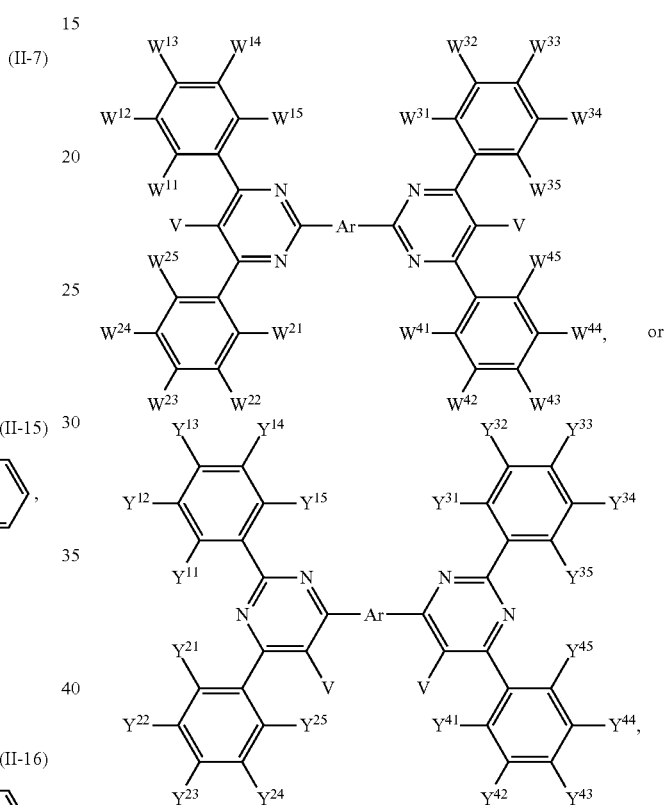 or
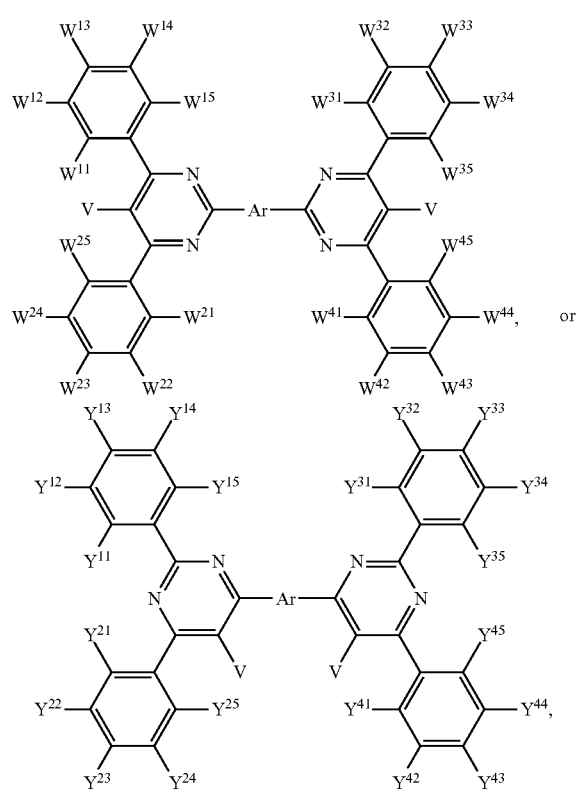,
wherein
Ar is a group of formula
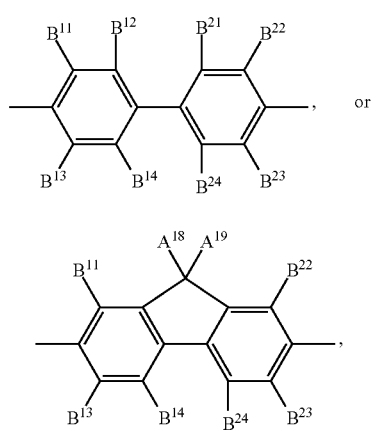, or especially

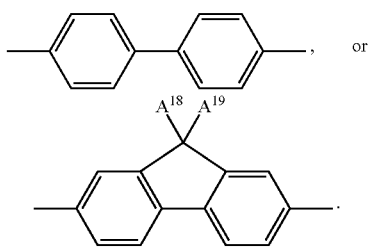

WO2008119666 discloses compounds of formula

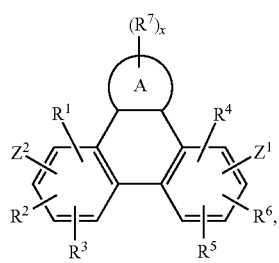

(I)

a process for their preparation and their use in organic light emitting diodes (OLEDs), especially as host for phosphorescent compounds. The hosts may function with phosphorescent materials to provide improved efficiency, stability, manufacturability, or spectral characteristics of electroluminescent devices. $Z^1$ and $Z^2$ can be a group of the formula

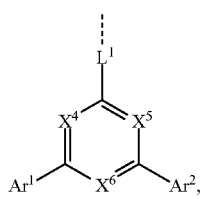

wherein $X^4$, $X^5$ and $X^6$ are independently of each other N, or CH, with the proviso that at least one, preferably at least two of the substituents $X^4$, $X^5$ and $X^6$ are N, and $Ar^1$ and $Ar^2$ are independently of each other optionally substituted $C_6$-$C_{24}$aryl, or $C_2$-$C_{20}$heteroaryl. The following compound is explicitly disclosed:

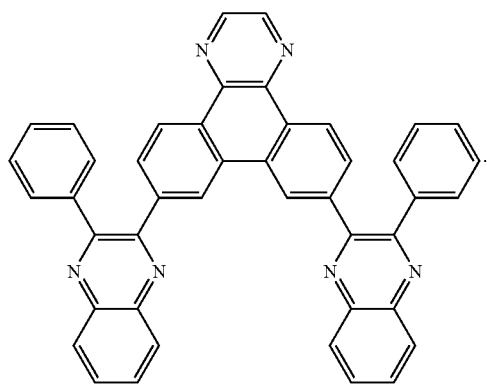 [SMILES: c1ccc(-c2nc3ccccc3nc2-c2ccc3c(c2)c2cc(-c4nc5ccccc5nc4-c4ccccc4)ccc2c2nccnc32)cc1]

WO2009037155 discloses electroluminescent devices, comprising a compound of the formula

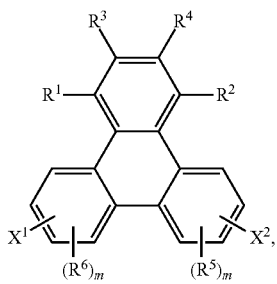

especially as host for phosphorescent compounds, wherein $X^1$ and $X^2$ can be a group of the formula

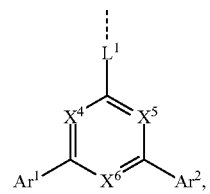

$X^4$, $X^5$ and $X^6$ are independently of each other N, or CH, with the proviso that at least one, preferably at least two of the substituents $X^4$, $X^5$ and $X^6$ are N, and $Ar^1$ and $Ar^2$ are independently of each other optionally substituted $C_6$-$C_{24}$aryl, or $C_2$-$C_{20}$heteroaryl. The hosts may function with phosphorescent materials to provide improved efficiency, stability, manufacturability, or spectral characteristics of electroluminescent devices.

WO2005053055 relates to EL devices, containing a hole blocking layer comprising a compound of the following structure

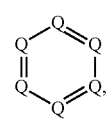

wherein Q is N or CR with the proviso that et least one Q is N, The following compounds are given as an example:

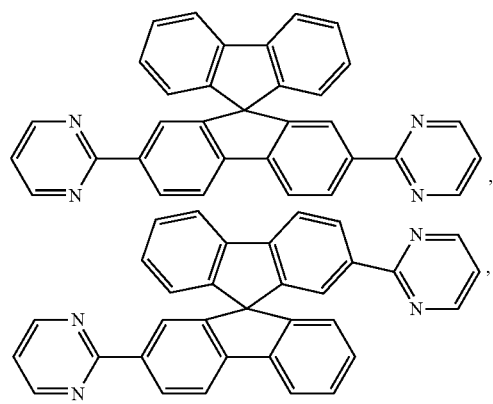

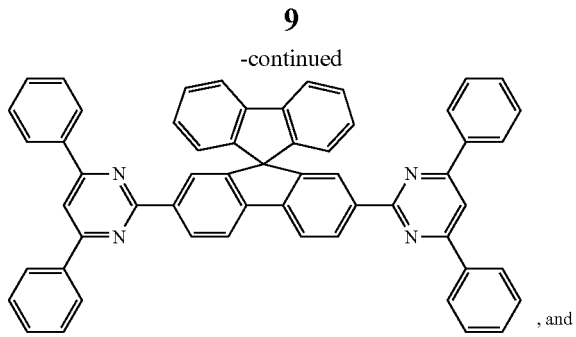

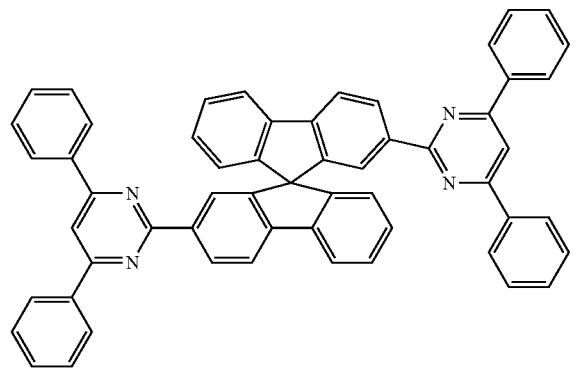

JP2009184987 describes compounds of the following structure for the use as electron transport materials:

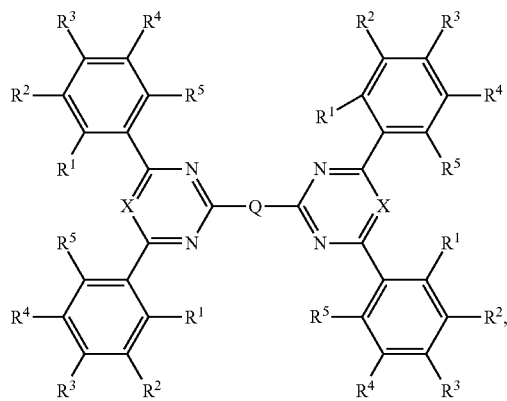

wherein X is CR, or N, and Q is

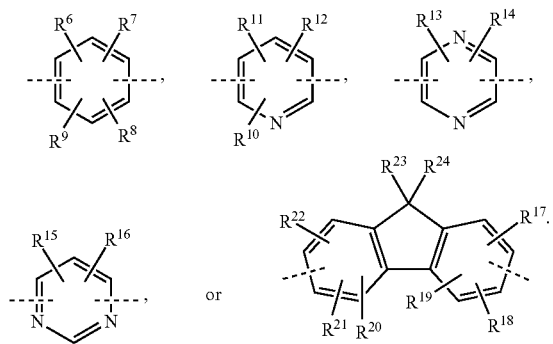

WO2009069442 relates to an organic electroluminescent device having high emission luminance and low driving voltage. The organic electroluminescent device contains at least one compound of formula

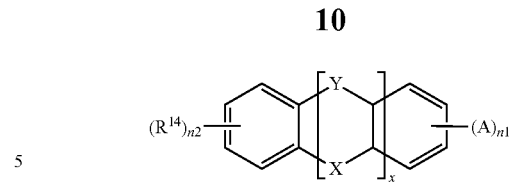

[A is a group of formula

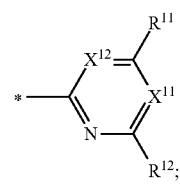

the sum of n1 and n2 is an integer of 6 to 8; $X^{11}$ and $X^{12}$=N or $CR^{13}$; $R^{13}$ and $R^{14}$ is H or substituent, but do not combine together to form a ring; when $X^{11}$ and $X^{12}$ are both $CR^{13}$, both groups $R^{13}$ may be the same as or different from each other; x is 0, or 1, when x=1, —Y— and —X— are a direct bond or —O—, —S— or —N($R^{15}$)—; and $R^{15}$ is a substituent].

Examples of such compounds are shown below:

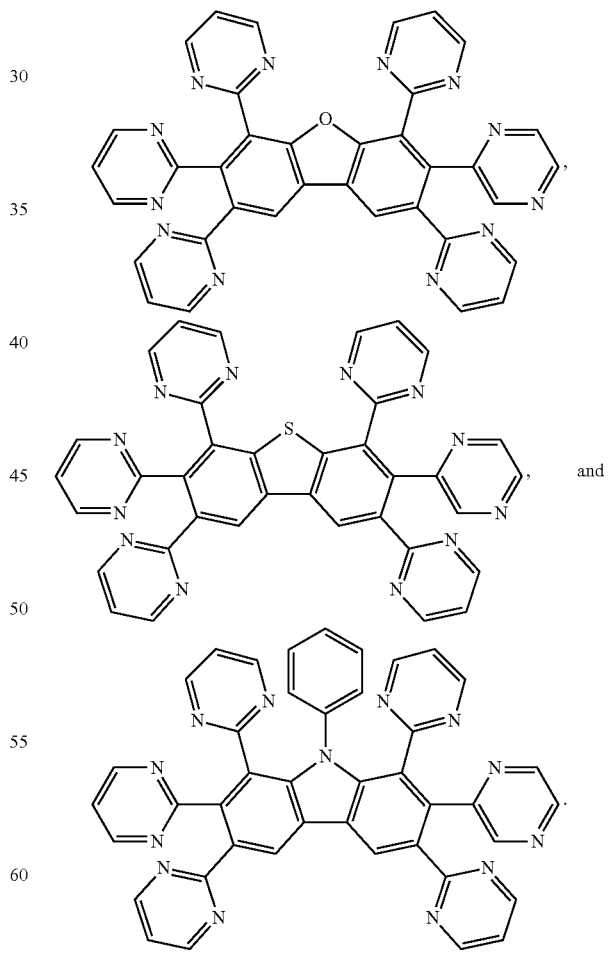

WO2009084546 describes an organic electroluminescent device (organic EL device), containing 2,2'-bispyrimidines of formula

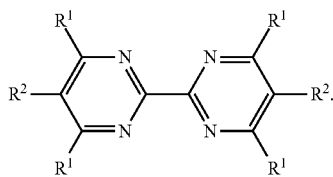

The light-emitting layer of the EL device contains a phosphorescent dopant and a bispyrimidine compound, such as, for example,

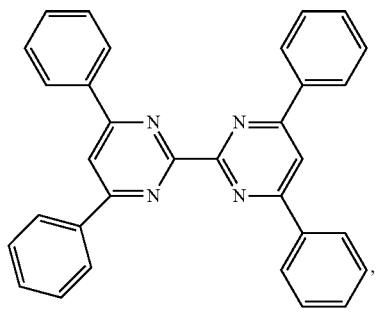 [SMILES: c1ccc(-c2cc(-c3ccccc3)nc(-c3nc(-c4ccccc4)cc(-c4ccccc4)n3)n2)cc1]

which serves as a host material.

WO2009054253 relates to an organic electroluminescent device. The organic electroluminescent device is characterized by containing at least one compound represented by the following general formula Ar-(A)$_n$ (In the formulae, Ar represents a monocyclic or bicyclic aromatic ring or an aromatic heterocyclic ring, each of which contains at least one hydrogen atom; n represents an integer of 3, 4 or 5; A represents a group represented by the general formula

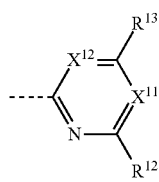

and a plurality of A's may be the same as or different from one another; $X^{11}$ and $X^{12}$ each represents a nitrogen atom or $CR^{13}$; $R^{11}$, $R^{12}$ and $R^{13}$ each represents a hydrogen atom or a substituent, but they do not combine together to form a ring; when $X^{11}$ and $X^{12}$ are both $CR^{13}$, $R^{13}$'s may be the same as or different from each other; and at least three of A's bonded to Ar are bonded to carbon atoms of Ar which are adjacent to one another.

U.S.2009102356 discloses organic compounds having electron-transporting and/or hole-blocking performance, wherein said organic compound is a multi-aryl substituted pyridine derivative. An example of such a compound is shown below:

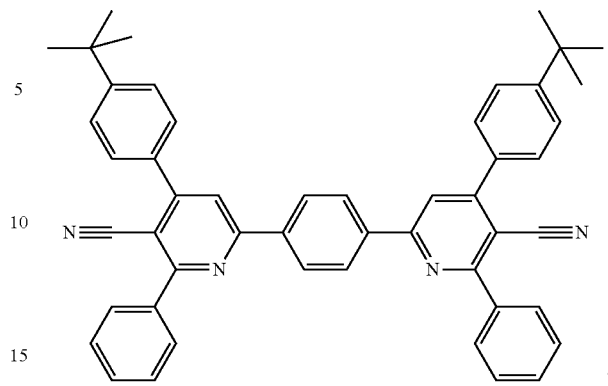

KR2009008737 describes compounds of the following structure as electron hole injection, electron injection and transport material for OLED.

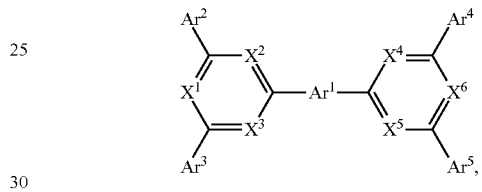

wherein $X^1$ to $X^6$ are N, or CR. Examples of such compounds are shown below:

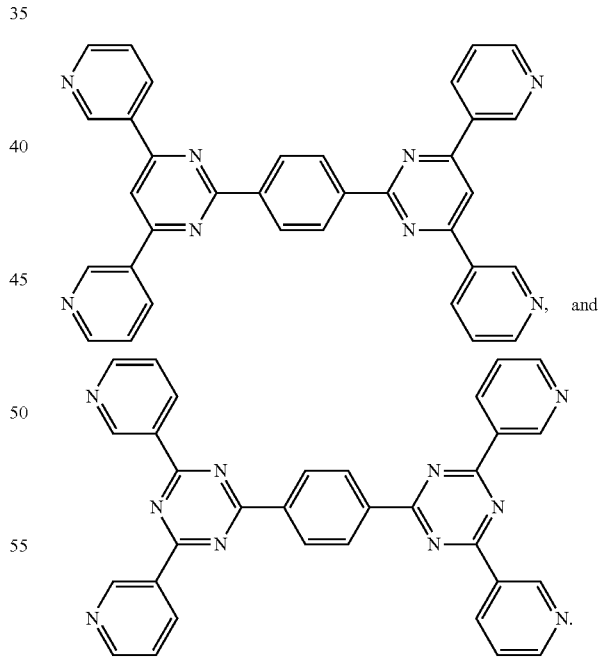

JP2009021336 relates to an organic electroluminescent element which has at least an anode, a light emission layer, an electron transporting layer, and a cathode as constitution layers such that the light emission layer contains at least a host compound and a metal complex. The host compound is a compound of formula

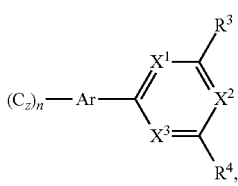

such as, for example,

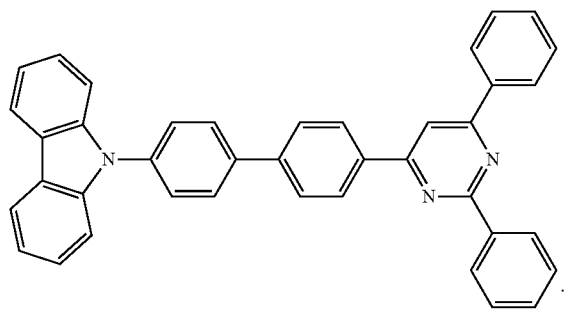 [SMILES: c1ccc(-c2cc(-c3ccc(-c4ccc(-n5c6ccccc6c6ccccc65)cc4)cc3)nc(-c3ccccc3)n2)cc1]

WO09008353 discloses an organic EL device containing a chrysene derivative, which has a larger energy gap than anthracenes, in an electron transport layer. The following bispyrimidine compounds are explicitly mentioned:

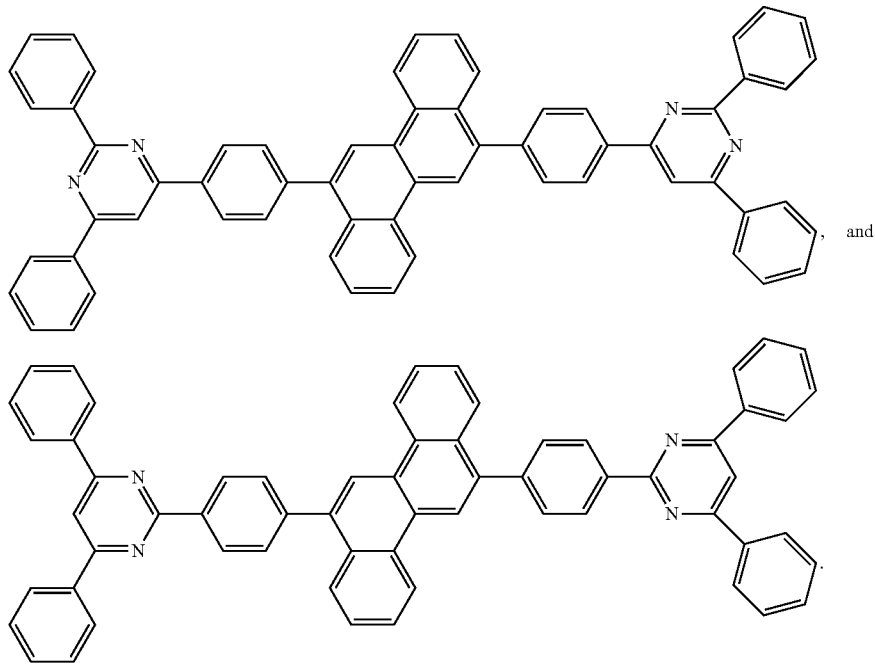

EP1724323 relates to an material for an organic electroluminescence device comprising a compound represented by the following general formula (1):

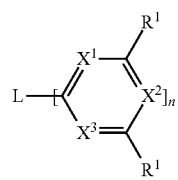

where: L represents a linking group having at least one meta bond;

$R^1$ and $R^2$ each independently represent a hydrogen atom, an alkyl group which has 1 to 50 carbon atoms and which may have a substituent, a heterocyclic group which has 5 to 50 ring atoms and which may have a substituent, an alkoxy group which has 1 to 50 carbon atoms and which may have a substituent, an aryloxy group which has 5 to 50 ring carbon atoms and which may have a substituent, an aralkyl group which has 7 to 50 ring carbon atoms and which may have a substituent, an alkenyl group which has 2 to 50 carbon atoms and which may have a substituent, an alkylamino group which has 1 to 50 carbon atoms and which may have a substituent, an arylamino group which has 5 to 50 ring carbon atoms and which may have a substituent, an aralkylamino group which has 7 to 50 ring carbon atoms and which may have a substituent, an aryl group which has 6 to 50 ring carbon atoms and which may have a substituent, or a cyano group;

$X^1$ to $X^3$ each independently represent =CR- or =N—, at least one of $X^1$ to $X^3$ representing =N— where R represents an aryl group which has 6 to 50 ring carbon atoms and which may have a substituent, a heterocyclic group which has 5 to 50 ring atoms and which may have a substituent, an alkyl group which has 1 to 50 carbon atoms and which may have a substituent, an alkoxy group which has 1 to 50 carbon atoms and which may have a substituent, an aralkyl group which has 7 to 50 ring carbon atoms and which may have a substituent, an aryloxy group which has 5 to 50 ring carbon atoms and which may have a substituent, an arylthio group which has 5 to 50 ring carbon atoms and which may have a substituent, a carboxyl group, a halogen atom, a cyano group, a nitro group, or a hydroxyl group; and n represents an integer of 1 to 5. The following bispyrimidine compounds are explicitly disclosed:

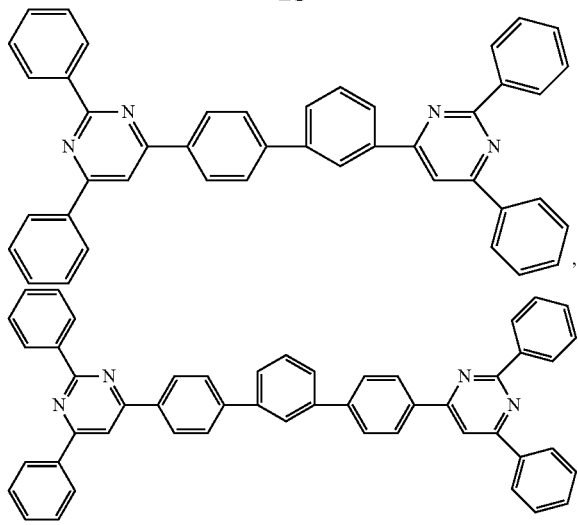

etc. The compound of formula (1) is preferably used as host material in combination with a phosphorescent dopant in the light emitting layer.

JP2005255561 provides a selective method for producing a multi-substituted pyrimidine suitable for a luminescent material, such as, for example,

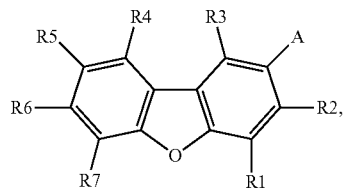

WO10090077 relates to an material for an organic electroluminescence device comprising a compound represented by the following general formula

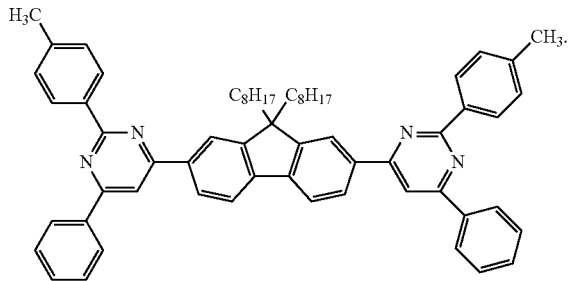
(1)

such as, for example,

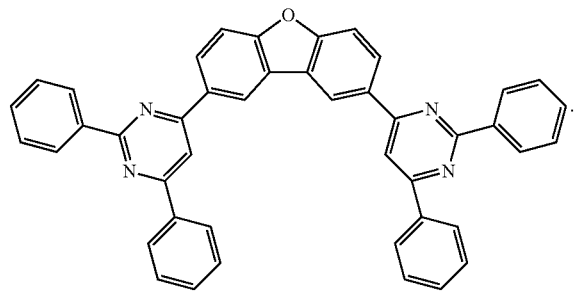 [SMILES: c1ccc(-c2cc(-c3ccc4oc5ccc(-c6cc(-c7ccccc7)nc(-c7ccccc7)n6)cc5c4c3)nc(-c3ccccc3)n2)cc1]

The following compound is explicitly disclosed in JP2010135467:

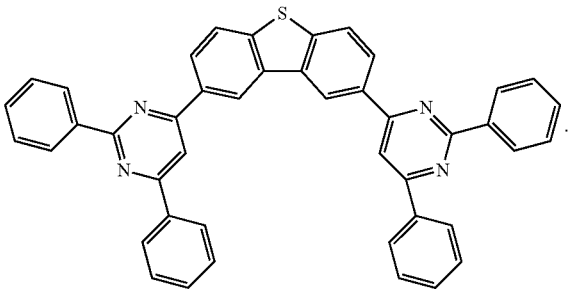 [SMILES: c1ccc(-c2cc(-c3ccc4sc5ccc(-c6cc(-c7ccccc7)nc(-c7ccccc7)n6)cc5c4c3)nc(-c3ccccc3)n2)cc1]

Notwithstanding these developments, there remains a need for organic light emitting devices comprising new electron transport materials to provide improved efficiency, stability, manufacturability, and/or spectral characteristics of electroluminescent devices.

Accordingly, it was the object of the present invention to provide compounds, which when used in organic electronic devices, especially organic light emitting devices showing good efficiencies, good operative lifetimes, good manufacturability, good spectral characteristics, a high stability to thermal stress, and/or a low operating voltage.

Certain organic compounds containing two pyrimidine moieties are found to be suitable for use in organo-electroluminescent devices. In particular, certain pyrimidine derivatives are suitable electron transporting materials, or hole blocking materials with good efficiency and durability. When the compounds are used as electron transporting material, they may also prevent holes or excitons from entering the electron transport layer.

Said object has been solved by compounds of the formula

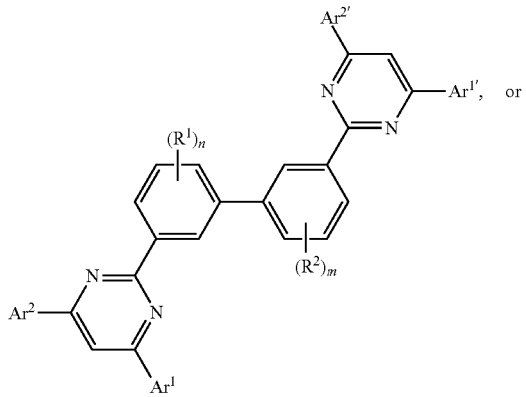
(I), or

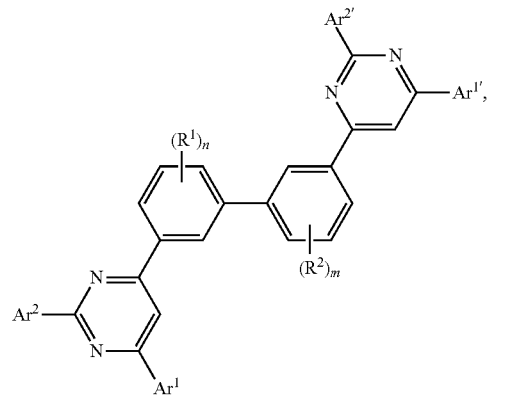
(II)

wherein $Ar^1$, $Ar^2$, $Ar^{1'}$ and $Ar^{2'}$ are independently of each other a $C_6$-$C_{24}$aryl group, or a $C_2$-$C_{30}$heteroaryl group, which can optionally be substituted by G, a $C_4$-$C_{18}$cycloalkyl, a $C_6$-$C_{10}$aryl group, a $C_6$-$C_{10}$aryl group which is substituted by by $C_1$-$C_8$alkyl, a $C_2$-$C_5$heteroaryl group, or a $C_2$-$C_5$heteroaryl group, which is substituted by by $C_1$-$C_8$alkyl, $R^1$ and $R^2$ can be the same or different at each occurrence and are F, CN, $NR^{45}R^{45'}$, a $C_1$-$C_{25}$alkyl group, a $C_4$-$C_{18}$cycloalkyl group, a $C_1$-$C_{25}$alkoxy group which is substituted by E or interrupted by D, a $C_6$-$C_{24}$aryl group, a $C_6$-$C_{24}$aryl group which is substituted by G, a $C_2$-$C_{30}$heteroaryl group, or a $C_2$-$C_{30}$heteroaryl group, which is substituted by G, m and n are 0, 1, 2, 3, or 4, D is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—, E is —OR$^{69}$, —SR$^{69}$, —NR$^{65}$R$^{66}$, —COR$^{68}$, —COOR$^{67}$, —CONR$^{65}$R$^{66}$, —CN, or halogen, G is E, or $C_1$-$C_{25}$alkyl, $R^{45}$ and $R^{45'}$ are independently of each other a $C_1$-$C_{25}$alkyl group, a $C_4$-$C_{18}$cycloalkyl group, in which one or more carbon atoms which are not in neighbourhood to each other could be replaced by —NR$^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^1$, and $R^{45''}$ is a $C_1$-$C_{25}$alkyl group, or a $C_4$-$C_{18}$cycloalkyl group, $R^{63}$ and $R^{64}$ are independently of each other H, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, or ring system;

$R^{67}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{68}$ is H; $C_6$-$C_{18}$aryl; $C_6$-$C_{18}$aryl which is substituted by $C_1$-$C_{10}$alkyl, or $C_1$-$C_{18}$alkoxy; $C_1$-$C_{18}$alkyl; or $C_1$-$C_{18}$alkyl which is interrupted by —O—, $R^{69}$ is $C_6$-$C_{18}$aryl, $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl.

$R^1$ and $R^2$ are preferably methyl, ethyl, propyl, iso-propyl, n-butyl, t-putyl, or phenyl.

m and n are preferably 0.

In a preferred embodiment the present invention is directed to compounds of formula

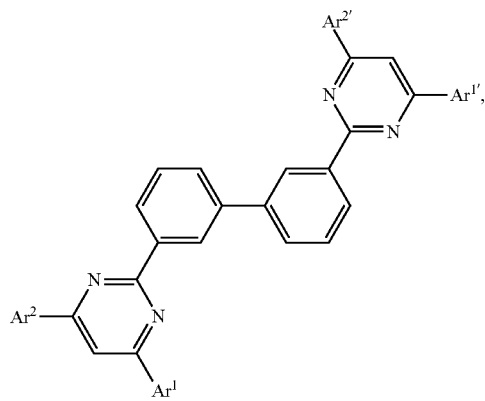

(Ia)

wherein $Ar^1$, $Ar^2$, $Ar^{1'}$ and $Ar^{2'}$ are as defined above.

Preferably, $Ar^1$, $Ar^2$, $Ar^{1'}$ and $Ar^{2'}$ are independently of each other selected from

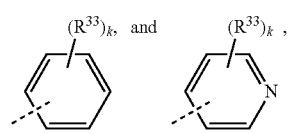

wherein $R^{33}$ is a $C_1$-$C_{25}$alkyl group, a $C_4$-$C_{18}$cycloalkyl group, a $C_1$-$C_{25}$alkoxy group, a $C_6$-$C_{10}$aryl group, a $C_6$-$C_{10}$aryl group which is substituted by by $C_1$-$C_8$alkyl, a $C_2$-$C_5$heteroaryl group, or a $C_2$-$C_5$heteroaryl group, which is substituted by by $C_1$-$C_8$alkyl, and k is 0, 1, 2, 3, or 4.

Preferably $R^{33}$ is $C_1$-$C_8$alkyl group, a $C_6$-$C_{10}$aryl group, a $C_6$-$C_{10}$aryl group which is substituted by $C_1$-$C_8$alkyl, a $C_2$-$C_5$heteroaryl group, or a $C_2$-$C_5$heteroaryl group, which is substituted by $C_1$-$C_8$alkyl.

k is preferably 0, 1, or 2, most preferred 0.

More preferably, $Ar^1$, $Ar^2$, $Ar^{1'}$ and $Ar^{2'}$ are independently of each other selected from

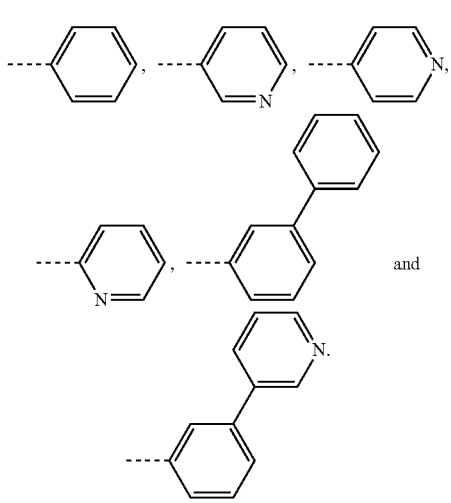

Compounds B-1 to B-8 are particularly preferred. Reference is made to claim 7.

In another preferred embodiment the present invention is directed to compounds of formula

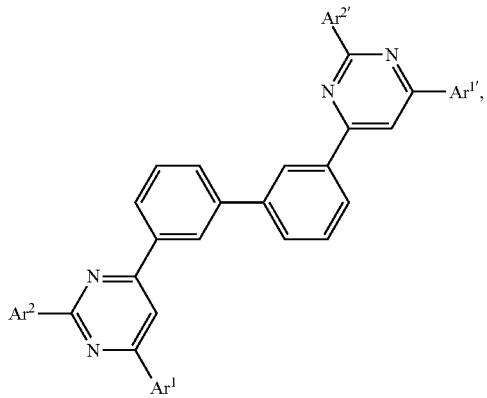
(IIa)

wherein $Ar^1$, $Ar^2$, $Ar^{1'}$ and $Ar^{2'}$ are as defined in claim 1.

Preferably, $Ar^1$, $Ar^2$, $Ar^{1'}$ and $Ar^{2'}$ are independently of each other selected from

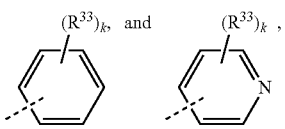

wherein $R^{33}$ is a $C_1$-$C_{25}$alkyl group, a $C_4$-$C_{18}$cycloalkyl group, a $C_6$-$C_{10}$aryl group, a $C_6$-$C_{10}$aryl group which is substituted by by $C_1$-$C_5$alkyl, a $C_2$-$C_5$heteroaryl group, or a $C_2$-$C_5$heteroaryl group, which is substituted by by $C_1$-$C_8$alkyl, and k is 0, 1, 2, 3, or 4.

More preferably, $Ar^1$, $Ar^2$, $Ar^{1'}$ and $Ar^{2'}$ are independently of each other selected from

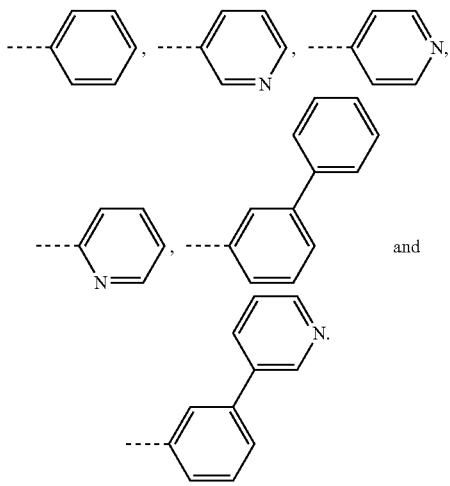

Compounds A-1 to A-8 are particularly preferred. Reference is made to claim 4.

The compounds of formula I of the present invention can be prepared according to a process, which comprises reacting a compound of formula

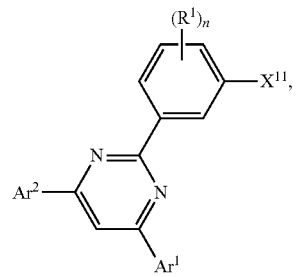
(III)

wherein $X^{11}$ stands for halogen, such as bromo, or iodo, with a compound of formula

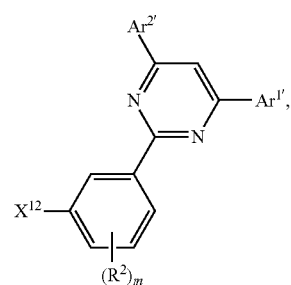
(IV)

wherein $X^{12}$ is —B(OH)$_2$, —B(OY$^1$)$_2$,

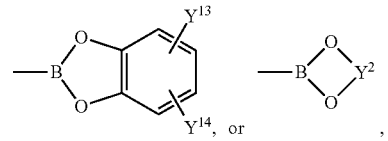

wherein $Y^1$ is independently in each occurrence a $C_1$-$C_{18}$alkylgroup and $Y^2$ is independently in each occurrence a $C_2$-$C_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein Y$^3$, Y$^4$, Y$^5$, Y$^6$, Y$^7$, Y$^8$, Y$^9$, Y$^{10}$, Y$^{11}$ and Y$^{12}$ are independently of each other hydrogen, or a $C_1$-$C_{18}$alkylgroup, especially —C(CH$_3$)$_2$C(CH$_3$)$_2$—, —C(CH$_3$)$_2$CH$_2$C(CH$_3$)$_2$—, or —CH$_2$C(CH$_3$)$_2$CH$_2$—, and Y$^{13}$ and Y$^{14}$ are independently of each other hydrogen, or a $C_1$-$C_{18}$alkylgroup, in the presence of a base and a catalyst in a solvent, wherein $Ar^1$, $Ar^{1'}$, $Ar^2$, $Ar^{2'}$, m, n, R$^1$ and R$^2$ are as defined above.

The compounds of formula II of the present invention can be prepared according to a process, which comprises reacting a compound of formula

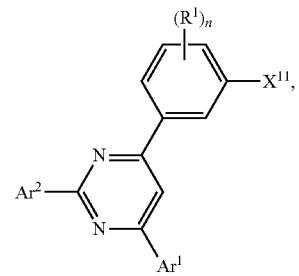
(V)

wherein $X^{11}$ stands for halogen, such as bromo, or iodo, with a compound of formula

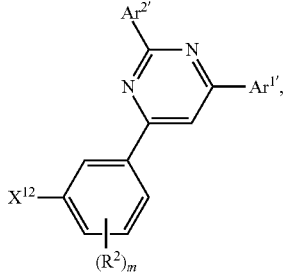

(VI)

wherein $X^{12}$ is —B(OH)$_2$, —B(OY$^1$)$_2$,

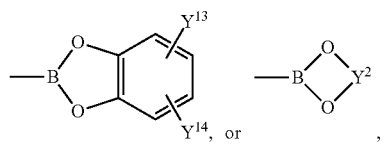

wherein $Y^1$ is independently in each occurrence a $C_1$-$C_{18}$alkylgroup and $Y^2$ is independently in each occurrence a $C_2$-$C_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein Y$^3$, Y$^4$, Y$^5$, Y$^6$, Y$^7$, Y$^8$, Y$^9$, Y$^{10}$, Y$^{11}$ and Y$^{12}$ are independently of each other hydrogen, or a $C_1$-$C_{18}$alkylgroup, especially —C(CH$_3$)$_2$C(CH$_3$)$_2$—, —C(CH$_3$)$_2$CH$_2$C(CH$_3$)$_2$—, or —CH$_2$C(CH$_3$)$_2$CH$_2$—, and Y$^{13}$ and Y$^{14}$ are independently of each other hydrogen, or a $C_1$-$C_{18}$alkylgroup, in the presence of a base and a catalyst in a solvent, wherein Ar$^1$, Ar$^{1'}$, Ar$^2$, Ar$^{2'}$, m, n, R$^1$ and R$^2$ are as defined above. The catalyst may be one of the μ-halo(triisopropylphosphine)(η$^3$-allyl)palladium(II) type (see for example WO99/47474).

Preferably, the reaction is carried out in the presence of an organic solvent, such as an aromatic hydrocarbon or a usual polar organic solvent, such as benzene, toluene, xylene, tetrahydrofurane, or dioxane, or mixtures thereof, most preferred toluene. Usually, the amount of the solvent is chosen in the range of from 1 to 10 l per mol of boronic acid derivative. Also preferred, the reaction is carried out under an inert atmosphere such as nitrogen, or argon. Further, it is preferred to carry out the reaction in the presence of an aqueous base, such as an alkali metal hydroxide or carbonate such as NaOH, KOH, Na$_2$CO$_3$, K$_2$CO$_3$, Cs$_2$CO$_3$ and the like, preferably an aqueous K$_2$CO$_3$ solution is chosen. Usually, the molar ratio of the base to boronic acid or boronic ester derivative is chosen in the range of from 0.5:1 to 50:1, very especially 1:1. Generally, the reaction temperature is chosen in the range of from 40 to 180° C., preferably under reflux conditions. Preferred, the reaction time is chosen in the range of from 1 to 80 hours, more preferably from 20 to 72 hours. In a preferred embodiment a usual catalyst for coupling reactions or for polycondensation reactions is used, preferably Pd-based, which is described in WO2007/101820. The palladium compound is added in a ratio of from 1:10000 to 1:50, preferably from 1:5000 to 1:200, based on the number of bonds to be closed. Preference is given, for example, to the use of palladium(II) salts such as PdAc$_2$ or Pd$_2$dba$_3$ and to the addition of ligands selected from the group consisting of

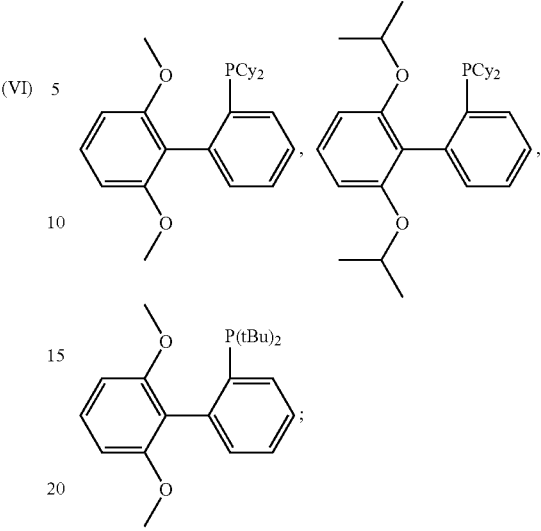

wherein Cy=

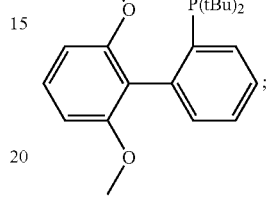

The ligand is added in a ratio of from 1:1 to 1:10, based on Pd. Also preferred, the catalyst is added in solution, or suspension. Preferably, an appropriate organic solvent, such as the ones described above, preferably benzene, toluene, xylene, THF, dioxane, more preferably toluene, or mixtures thereof, is used. The amount of solvent usually is chosen in the range of from 1 to 10 l per mol of boronic acid derivative.

The synthesis of pyrimidines carrying bromine units, i.e. the compounds of formula III and V, can be done in analogy to the methods described in U.S.20070190355 and Majid M. Heravi et al., Tetrahedron Letters 50 (2009) 662-666.

Compounds of formula IV and VI can be obtained by reacting compounds of formula III and V with (OY$^1$)$_2$B—B(OY$^1$)$_2$,

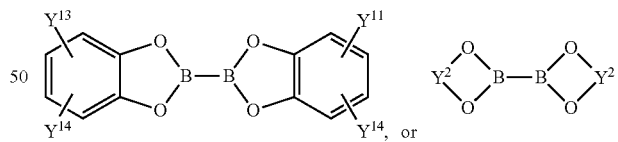

in the presence of a catalyst, such as, for example, [1,1-bis(diphenylphosphino)ferrocene]dichloropalladium(II), complex (Pd(Cl)$_2$(dppf)), and a base, such as, for example, potassium acetate, in a solvent, such as, for example, dimethyl formamide, dimethyl sulfoxide, dioxane and/or toluene (cf. Prasad Appukkuttan et al., Synlett 8 (2003) 1204).

The compounds of of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices (=organic light-emitting diodes (OLEDs)).

Accordingly, a further subject of the present invention is directed to an electronic device, comprising a compound according to the present invention.

The electronic device is preferably an electroluminescent device.

The compounds of formula I, or II, can in principal be used in any layer of an EL device, but are preferably used as electron transport material.

Hence, a further subject of the present invention is directed to an electron transport layer, comprising a compound of the present invention.

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, iso-propyl, n-butyl, sec.-butyl, isobutyl, tert.-butyl, n-pentyl, 2-pentyl, 3-pentyl, 2,2-dimethylpropyl, 1,1,3,3-tetramethyl-pentyl, n-hexyl, 1-methylhexyl, 1,1,3,3,5,5-hexamethyl-hexyl, n-heptyl, isoheptyl, 1,1,3,3-tetramethylbutyl, 1-methylheptyl, 3-methyl-heptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, iso-butyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobu-toxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, iso-propoxy, n-butoxy, sec.-butoxy, isobutoxy, tert.-butoxy.

The term "cycloalkyl group" is typically $C_4$-$C_{18}$cycloalkyl, especially $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

$C_6$-$C_{24}$aryl ($C_6$-$C_{18}$aryl), which optionally can be substituted, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted.

$C_2$-$C_{30}$heteroaryl represents a ring with five to seven ring atoms or a condensed ring system, wherein nitrogen, oxygen or sulfur are the possible hetero atoms, and is typically a heterocyclic group with five to 30 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenox-ythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chi-nazolinyl, cinnolinyl, pteridinyl, carbazolyl, carbolinyl, ben-zotriazolyl, benzoxazolyl, phenanthridinyl, acridinyl, pyrim-idinyl, phenanthrolinyl, phenazinyl, isothiazolyl, phenothiazinyl, isoxazolyl, furazanyl or phenoxazinyl, which can be unsubstituted or substituted.

The $C_6$-$C_{24}$aryl ($C_6$-$C_{18}$aryl) and $C_2$-$C_{30}$heteroaryl groups are preferably substituted by one, or more $C_1$-$C_8$alkyl groups.

The term "aryl ether group" is typically a $C_{6-24}$aryloxy group, that is to say O—$C_{6-24}$aryl, such as, for example, phenoxy or 4-methoxyphenyl.

Possible substituents of the above-mentioned groups are $C_1$-$C_8$alkyl, a hydroxyl group, a mercapto group, $C_1$-$C_8$-alkoxy, $C_1$-$C_8$alkylthio, halogen, halo-$C_1$-$C_8$alkyl, or a cyano group.

If a substituent, such as, for example $R^1$ occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$-$R^x$, where $R^x$ is H or $C_1$-$C_{10}$alkyl or $C_2$-$C_{10}$alkanoyl (e.g. CO—CH($C_2H_5$) $C_4H_9$), $CH_2$—CH($OR^{y'}$)-$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H;

$C_1$-$C_8$alkylene-COO—$R^z$, e.g. $CH_2COOR^z$, $CH(CH_3)$ $COOR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)$ $CH_2$—O—CO—$C(CH_3)$=$CH_2$.

The organic electronic device of the present application is, for example, an organic solar cell (organic photovoltaics), a switching element. such as an organic transistors, for example organic FET and organic TFT, organic light emitting field effect transistor (OLEFET), or an organic light-emitting diode (OLED), preference being given to OLEDs.

The present application relates to the use of the compounds of formula I, or II preferably as electron transport layer in an organic electronic device.

Accordingly, the present application is also directed to an organic layer, especially an electron transport layer, comprising a compound of formula I, or II.

Suitable structures of organic electronic devices are known to those skilled in the art and are specified below.

The organic transistor generally includes a semiconductor layer formed from an organic layer with hole transport capacity and/or electron transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or electron transport capacity. In addition, it is possible for further layers known to those skilled in the art to be present in the organic solar cell. The layer with electron transport capacity may comprise the compounds of formula I, or II.

The present invention further relates to an organic light-emitting diode comprising an anode An and a cathode Ka, a light-emitting layer E arranged between the anode An and the cathode Ka, an electron transport layer arranged between the cathode Ka and the light-emitting layer E, and if appropriate at least one further layer selected from the group consisting of at least one blocking layer for holes/excitons, at least one blocking layer for electrons/excitons, at least one hole injection layer, at least one hole transport layer and at least one electron injection layer, wherein the electron transport layer comprises a compound of formula I, or II.

Structure of the Inventive OLED

The inventive organic light-emitting diode (OLED) thus generally has the following structure:

an anode (An) and a cathode (Ka) and a light-emitting layer E arranged between the anode (An) and the cathode (Ka) and an electron transport layer arranged between the cathode Ka and the light-emitting layer E.

The inventive OLED may, for example—in a preferred embodiment—be formed from the following layers:
1. Anode
2. Hole transport layer
3. Light-emitting layer
4. Blocking layer for holes/excitons
5. Electron transport layer
6. Cathode Layer sequences different than the aforementioned structure are also possible, and are known to those skilled in the art. For example, it is possible that the OLED does not have all of the layers mentioned; for example, OLEDs which have layers (1), (3), (4), (5) and (6), are likewise suitable. In addition, the OLEDs may have a blocking layer for electrons/excitons between the hole transport layer (2) and the light-emitting layer (3).

It is additionally possible that a plurality of the aforementioned functions (electron/exciton blocker, hole/exciton blocker, hole injection, hole transport, electron injection, electron transport) are combined in one layer and are assumed, for example, by a single material present in this layer. For example, a material used in the hole transport layer, in one embodiment, may simultaneously block excitons and/or electrons.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron transport layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole transport layer should be matched to the work function of the anode, and the LUMO (lowest unoccupied molecular orbital) of the electron transport layer should be matched to the work function of the cathode, provided that the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the periodic table of the elements (IUPAC version) are used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed. The material used for the anode (1) is preferably ITO.

Suitable hole transport materials for layer (2) of the inventive OLEDs are disclosed, for example, in Kirk-Othmer Encyclopedia of Chemical Technology, 4th edition, Vol. 18, pages 837 to 860, 1996. Both hole-transport molecules and polymers can be used as the hole transport material. Hole-transport molecules typically used are selected from the group consisting of tris[N-(1-naphthyl)-N-(phenylamino)] triphenylamine (1-NaphDATA), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4''-tris(N,N-diphenylamino)triphenylamine (TDTA), 4,4',4''-tris(N-carbazolyl)triphenylamine (TCTA), N,N'-bis(naphthalen-2-yl)-N,N'-bis(phenyl)benzidine (β-NPB), N,N'-bis(3-methylphenyl)-N,N'-bis(phenyl)-9,9-spirobifluorene (Spiro-TPD), N,N'-bis(naphthalen-1-yl)-N,N'-bis(phenyl)-9,9-spirobifluorene (Spiro-NPB), N,N'-bis(3-methylphenyl)-N,N'-bis(phenyl)-9,9-dimethylfluorene (DMFL-TPD), di[4-(N,N-ditolylamino)phenyl]cyclohexane, N,N'-bis(naphthalen-1-yl)-N,N'-bis(phenyl)-9,9-dimethylfluorene, N,N'-bis(naphthalen-1-yl)-N,N'-bis(phenyl)-2,2-dimethylbenzidine, N,N'-bis(naphthalen-1-yl)-N,N'-bis(phenyl)benzidine, N,N'-bis(3-methylphenyl)-N,N'-bis(phenyl)benzidine, 2,3,5,6-tetrafluoro-7,7,8,8-tetracyanoquinodimethane (F4-TCNQ), 4,4',4''-tris(N-3-methylphenyl-N-phenylamino)triphenylamine, 4,4',4''-tris(N-(2-naphthyl)-N-phenyl-amino)triphenylamine, pyrazino[2,3f]-[1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di[4-(N,N-ditolylamino)phenyl]benzidine (NTNPB), N,N'-diphenyl-N,N'-di[4-(N,N-diphenylamino)phenyl]benzidine (NPNPB), N,N'-di(naphthalen-2-yl)-N,N'-diphenylbenzene-1,4-diamine (6-NPP), N,N'-bis(3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (Spiro-TAD), 9,9-bis

[4-(N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N,N-bis(naphthalen-2-yl)-N,N'-bisphenylamino)phenyl]-9H-fluorene (NPBAPF), 2,2',7,7'-tetrakis[N-naphthalenyl(phenyl)amino]-9,9'-spirobifluorene (Spiro-2NPB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (Spiro-5), 2,2'-bis[N,N-bis(biphenyl-4-yl)amino]-9,9-spirobifluorene (2,2'-Spiro-DBP), 2,2'-bis(N,N-diphenylamino)-9,9-spirobifluorene (Spiro-BPA), 2,2',7,7'-tetra(N,N-ditolyl)aminospirobifluorene (Spiro-TTB), N,N,N',N'-tetranaphthalen-2-ylbenzidine (TNB), porphyrin compounds and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole transport materials, the band gap of the at least one hole transport material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is fac-Iridium-tris(1,3-diphenylbenzimidazolin-2-yliden-C,C$^{2'}$) (Ir(dpbic)$_3$) with the formula:

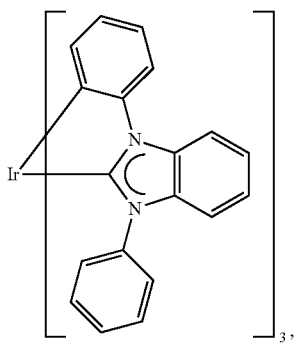

which is disclosed, for example, in WO2005/019373. Preferably, the hole transport layer comprises a compound of formula

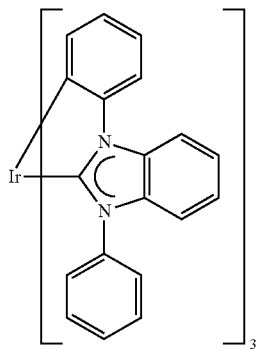

doped with molybdenum oxide (MoO$_x$), especially MoO$_3$, or rhenium oxide (ReO$_x$), especially ReO$_3$. The dopant is contained in an amount of from 0.1% by weight, preferably 1 to 50% by weight, more preferably 3 to 15% by weight, based on the amount of dopant and carbene complex.

The light-emitting layer (3) comprises at least one emitter material. In principle, it may be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance.

Suitable metal complexes for use in the inventive OLEDs are described, for example, in documents WO 02/60910 A1, U.S. 2001/0015432 A1, U.S. 2001/0019782 A1, U.S. 2002/0055014 A1, U.S. 2002/0024293 A1, U.S. 2002/0048689 A1, EP 1 191 612 A2, EP 1 191 613 A 2, EP 1 211 257 A2, U.S. 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669 and WO10086089.

The light emitting layer comprises preferably a compound of the formula

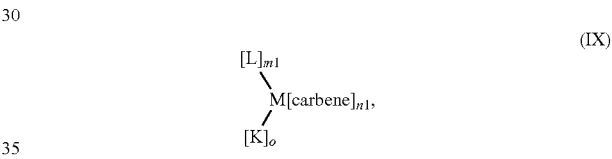

(IX)

which are described in WO 2005/019373 A2, wherein the symbols have the following meanings:

M is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom;

Carbene is a carbene ligand which may be uncharged or monoanionic and monodentate, bidentate or tridentate, with the carbene ligand also being able to be a biscarbene or triscarbene ligand;

L is a monoanionic or dianionic ligand, which may be monodentate or bidentate;

K is an uncharged monodentate or bidentate ligand selected from the group consisting of phosphines; phosphonates and derivatives thereof, arsenates and derivatives thereof; phosphites; CO; pyridines; nitriles and conjugated dienes which form a π complex with M$^1$;

n1 is the number of carbene ligands, where n1 is at least 1 and when n1>1 the carbene ligands in the complex of the formula I can be identical or different;

m1 is the number of ligands L, where m1 can be 0 or >1 and when m1>1 the ligands L can be identical or different;

o is the number of ligands K, where o can be 0 or >1 and when o>1 the ligands K can be identical or different;

where the sum n1+m1+o is dependent on the oxidation state and coordination number of the metal atom and on the denticity of the ligands carbene, L and K and also on the charge on the ligands, carbene and L, with the proviso that n1 is at least 1.

More preferred are metal-carbene complexes of the general formula

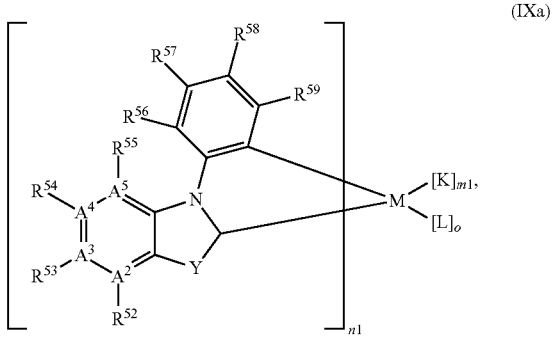

(IXa)

which are described in U.S. patent applications Ser. Nos. 61/286046, 61/323885 and Europen patent application 10187176.2 (WO2011073149), where M, n1, Y, $A^2$, $A^3$, $A^4$, $A^5$, $R^5$, $R^{52}$, $R^{53}$, $R^{54}$, $R^{55}$, $R^{56}$, $R^{57}$, $R^{58}$, $R^{59}$, K, L, m1 and o are each defined as follows:

M is Ir, or Pt, n1 is an integer selected from 1, 2 and 3,

Y is $NR^{51}$, O, S or $C(R^{25})_2$, $A^2$, $A^3$, $A^4$, and $A^5$ are each independently N or C, where 2 A=nitrogen atoms and at least one carbon atom is present between two nitrogen atoms in the ring, $R^{51}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{52}$, $R^{53}$, $R^{54}$ and $R^{55}$ are each, if $A^2$, $A^3$, $A^4$ and/or $A^5$ is N, a free electron pair, or, if $A^2$, $A^3$, $A^4$ and/or $A^5$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{53}$ and $R^{54}$ together with $A^3$ and $A^4$ form an optionally substituted, unsaturated ring optionally interrupted by at least one further heteroatom and having a total of 5 to 18 carbon atoms and/or heteroatoms, $R^{56}$, $R^{57}$, $R^{58}$ and $R^{59}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{56}$ and $R^{57}$, $R^{57}$ and $R^{58}$ or $R^{58}$ and $R^{56}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if $A^5$ is C, $R^{55}$ and $R^{56}$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{25}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, K is an uncharged mono- or bidentate ligand, L is a mono- or dianionic ligand, preferably monoanionic ligand, which may be mono- or bidentate, m1 is 0, 1 or 2, where, when m1 is 2, the K ligands may be the same or different, o is 0, 1 or 2, where, when o is 2, the L ligands may be the same or different.

The compound of formula IX is preferably a compound of the formula:

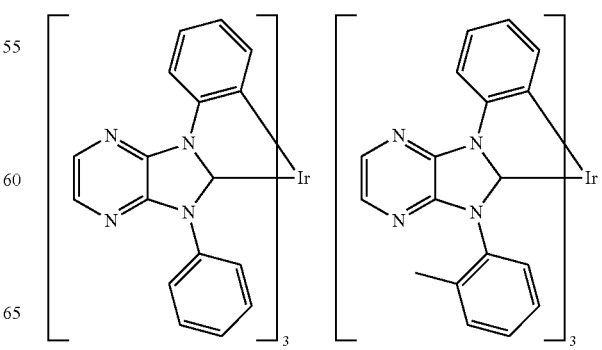

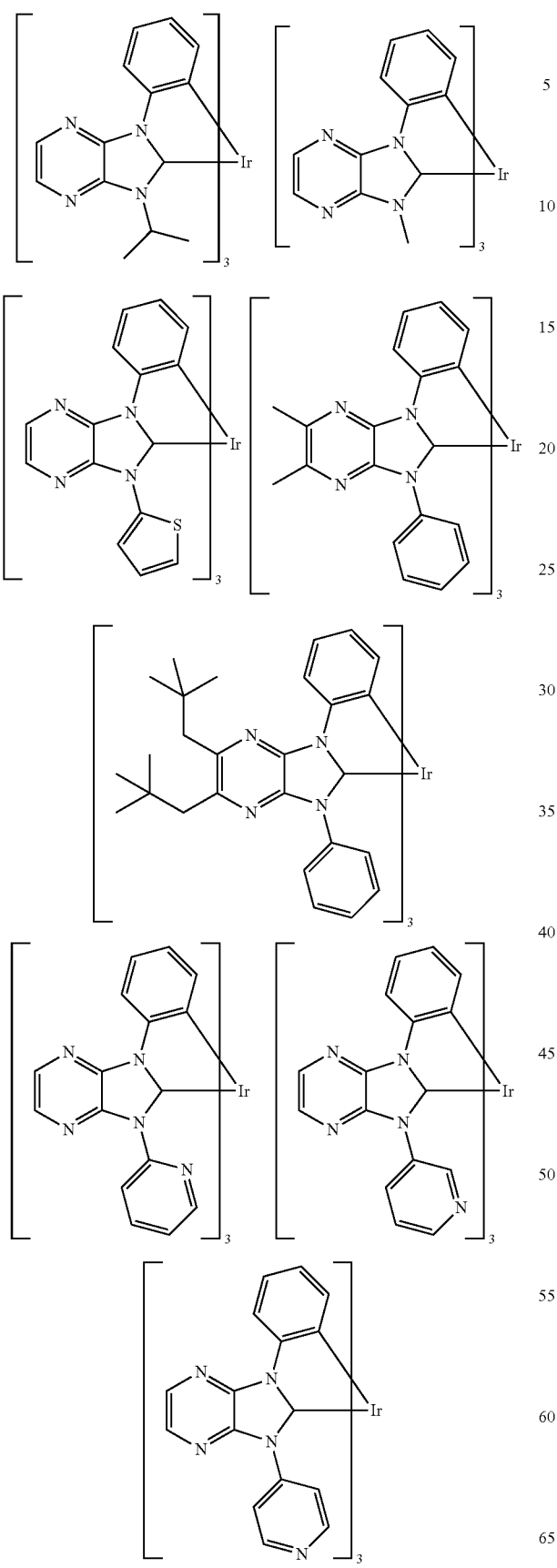
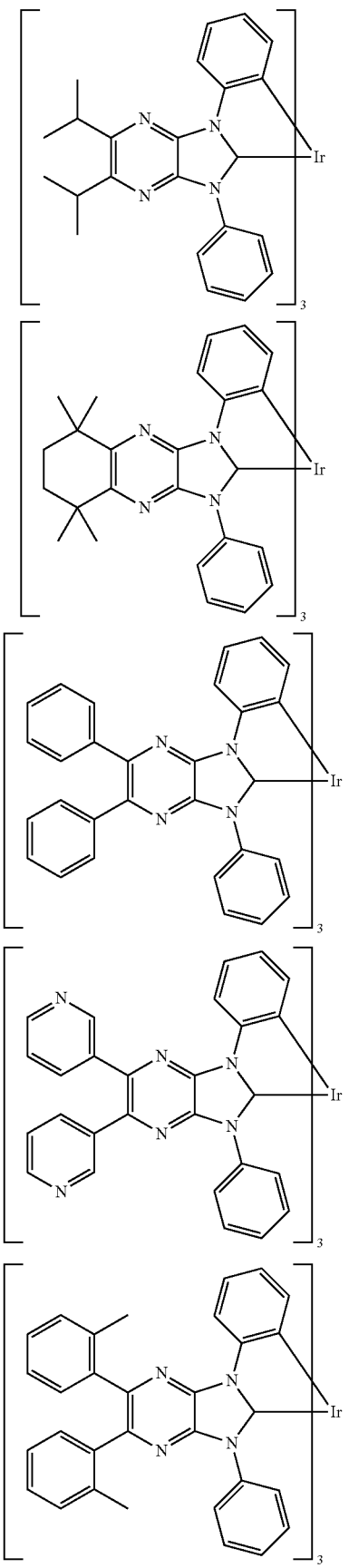

33
-continued
34
-continued
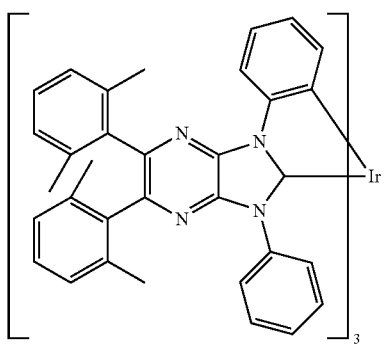
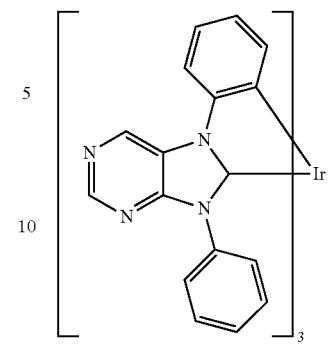
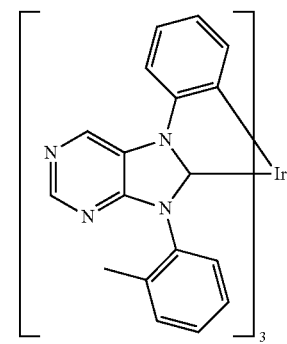
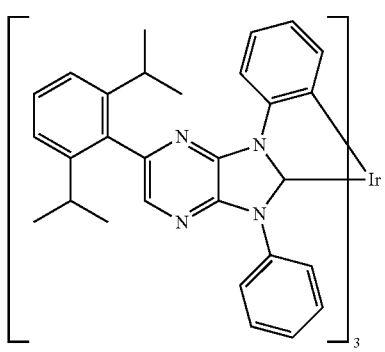
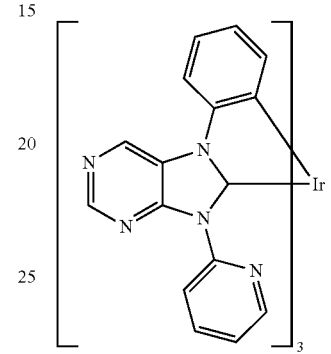
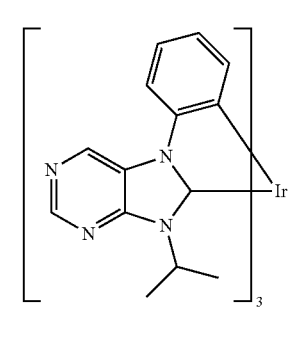
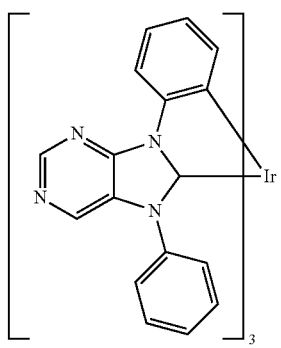
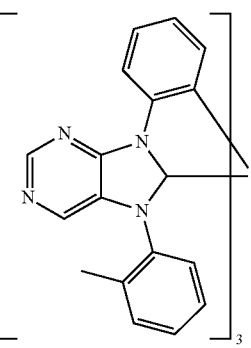
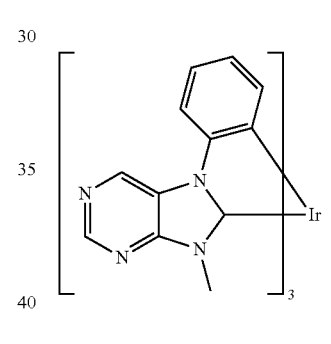
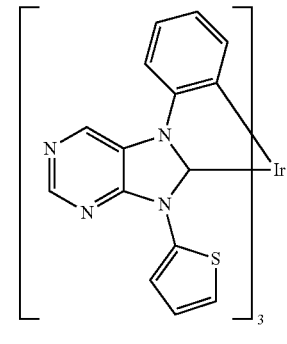
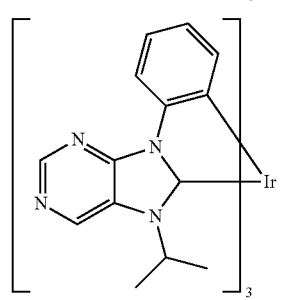
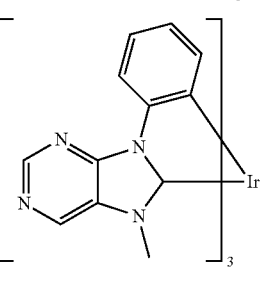
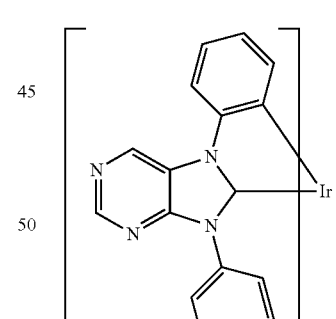
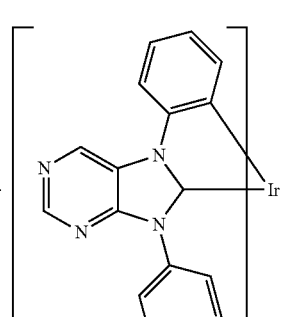
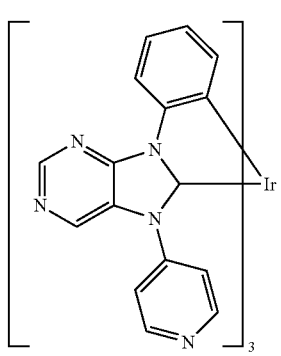
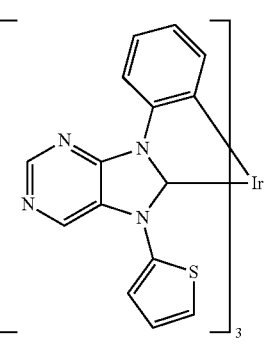
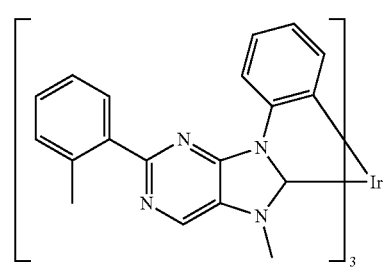

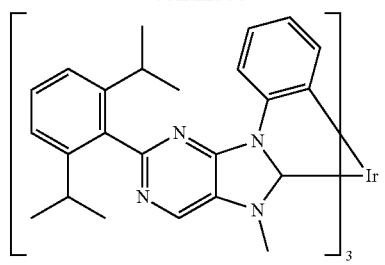
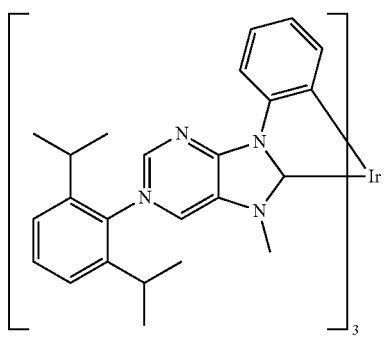
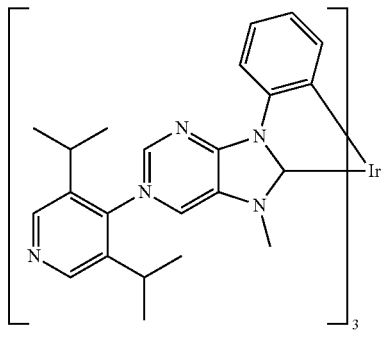
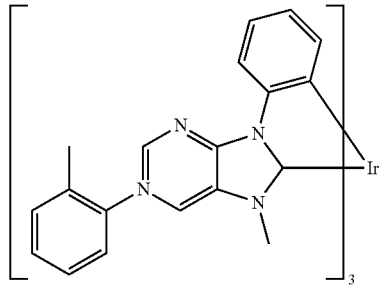
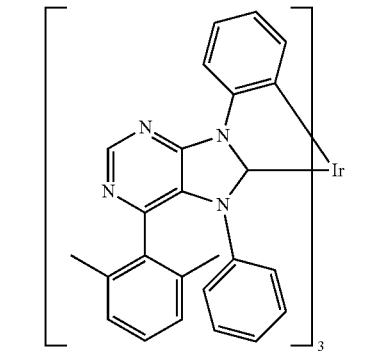
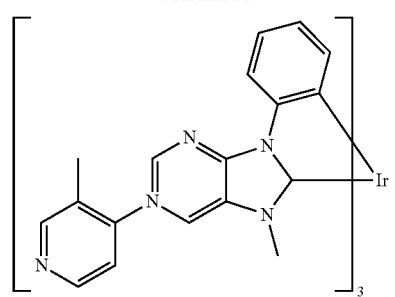
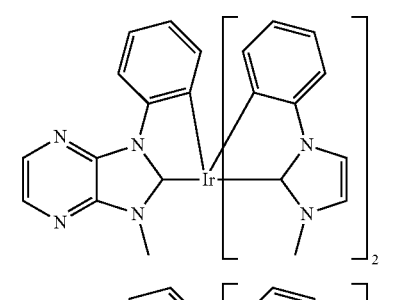
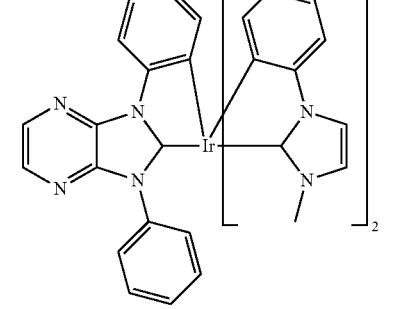
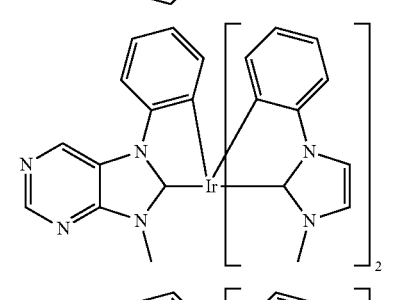
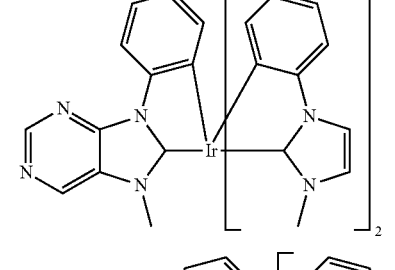
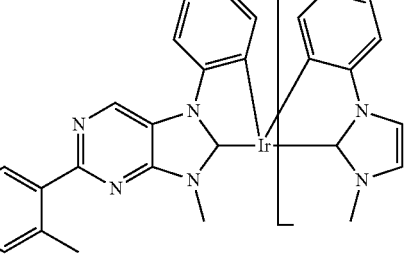

-continued
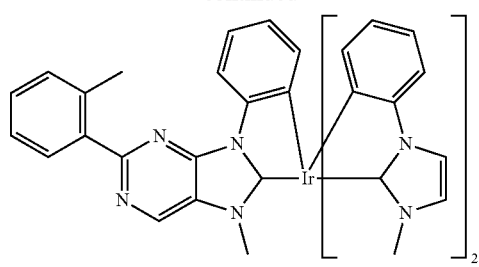
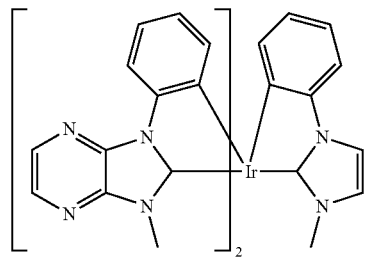
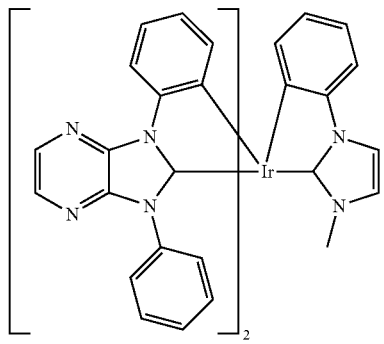
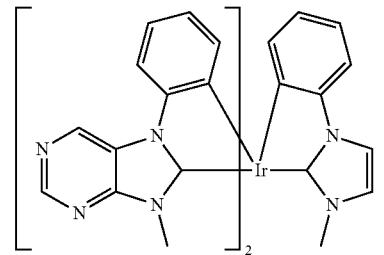
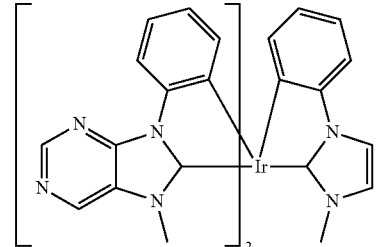
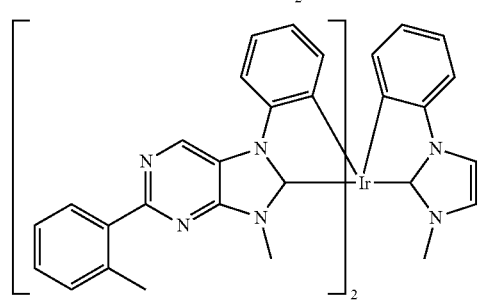
-continued
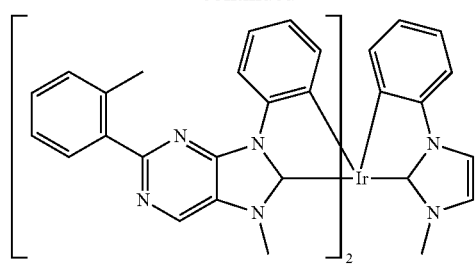
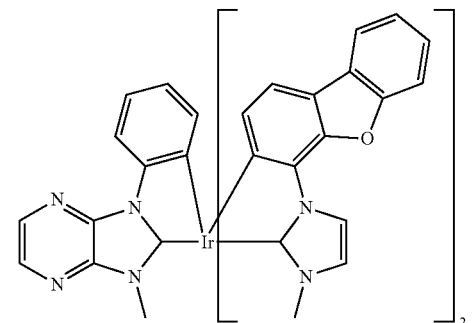
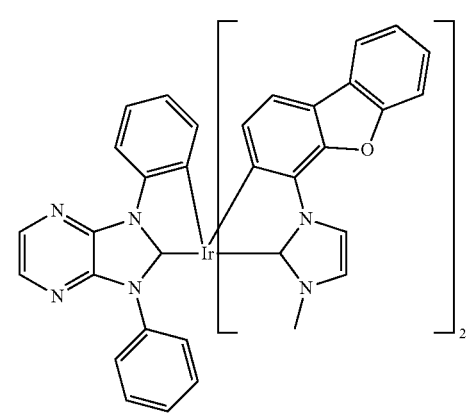
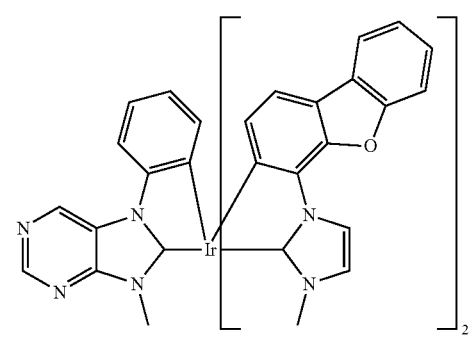
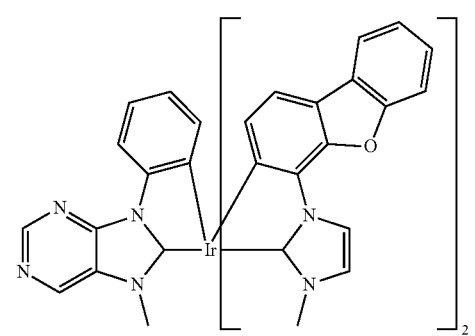

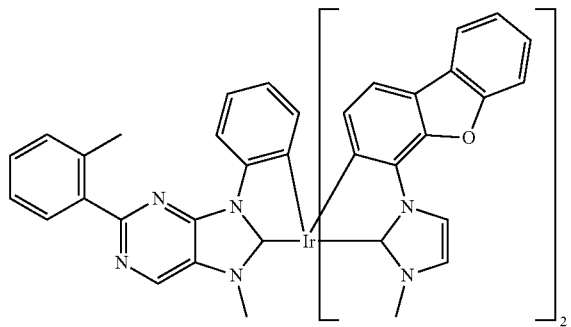
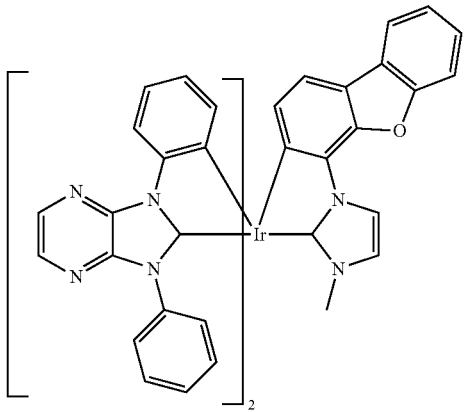
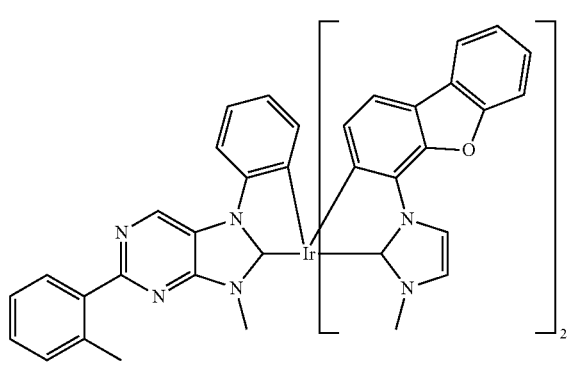
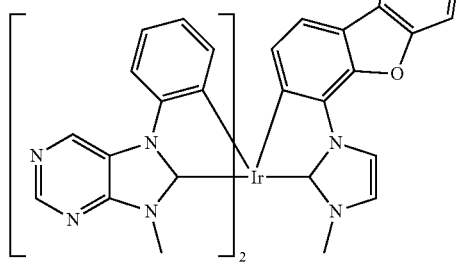
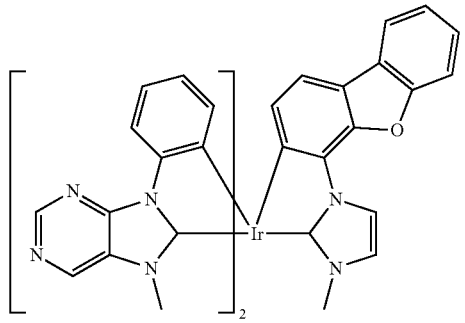
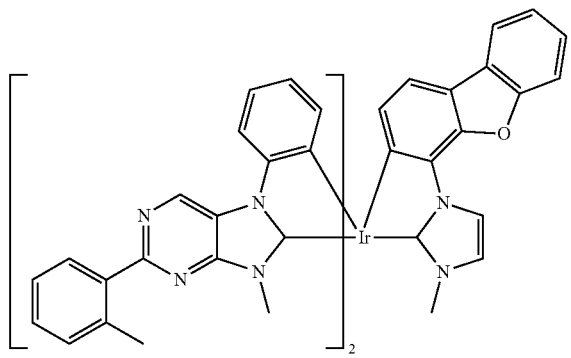
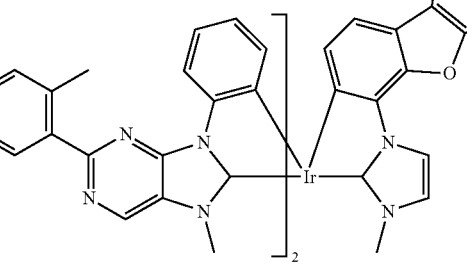
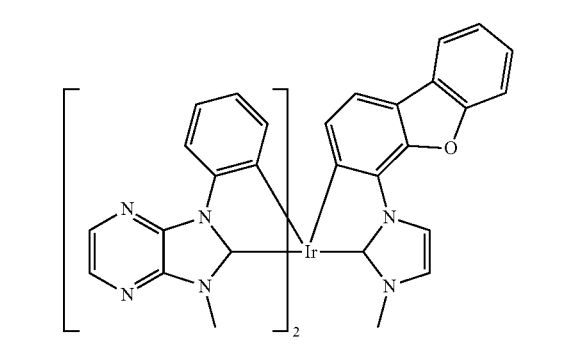
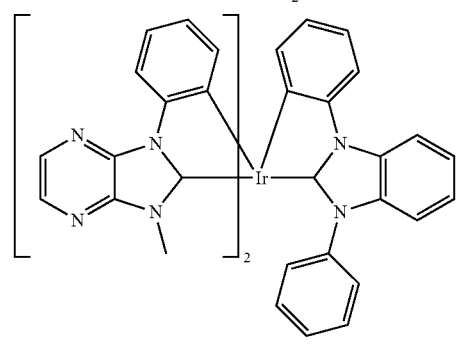

-continued
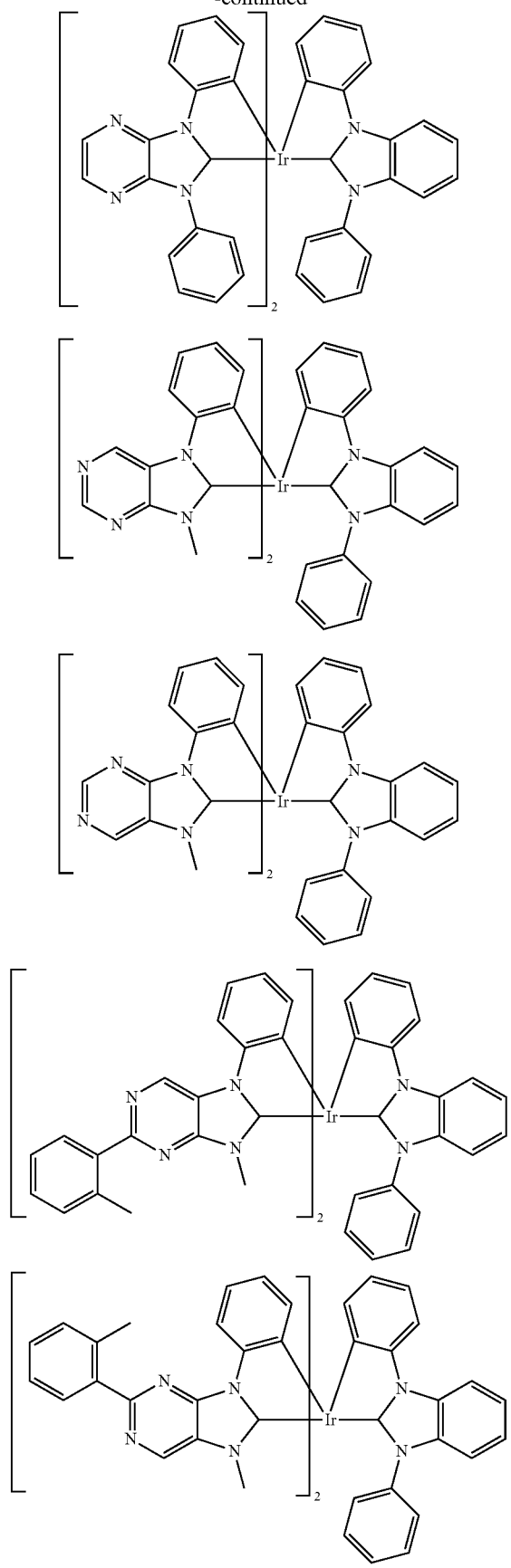
-continued
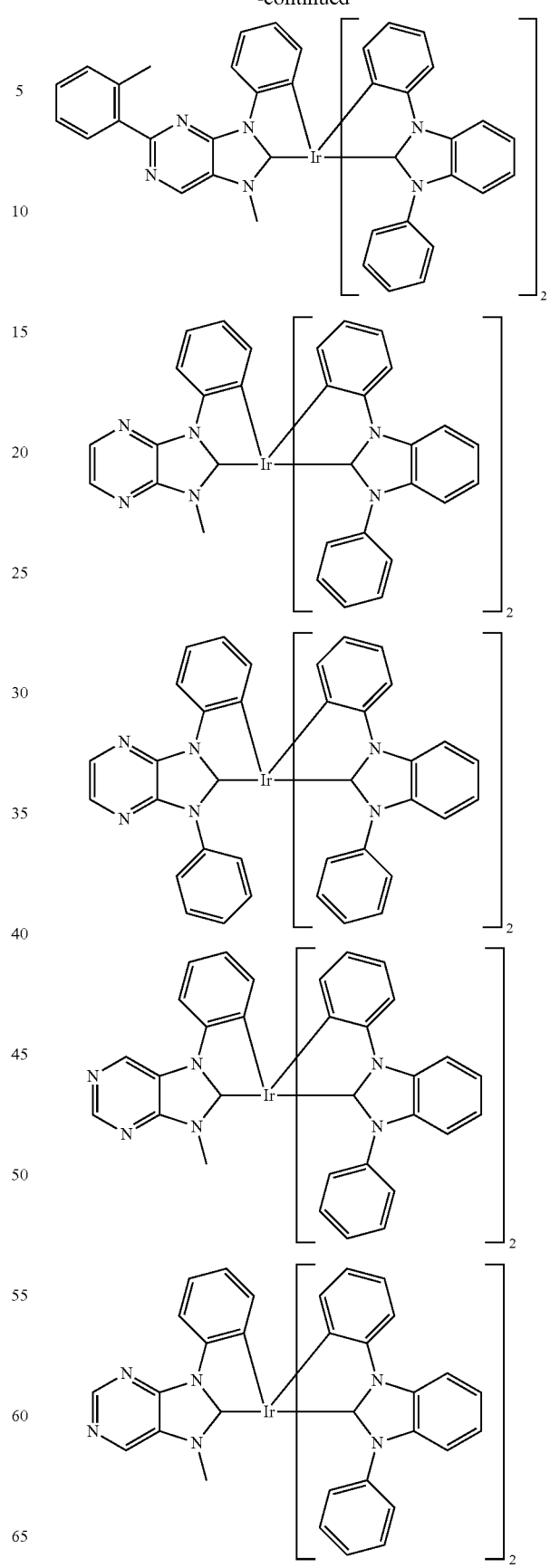

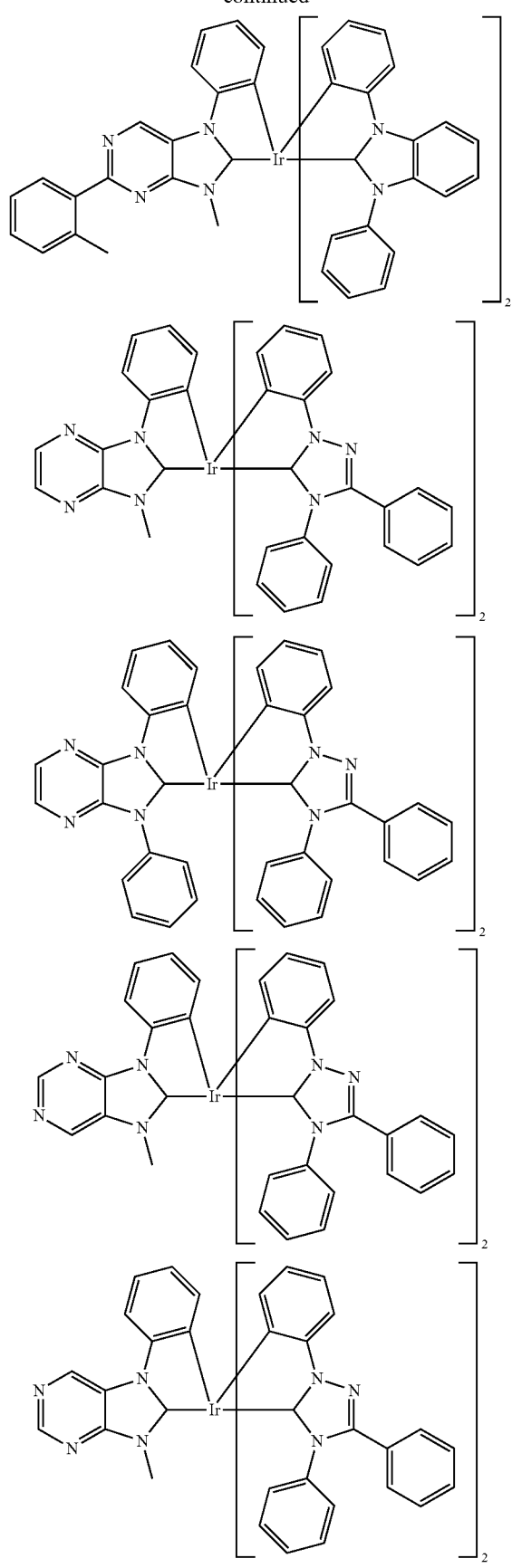
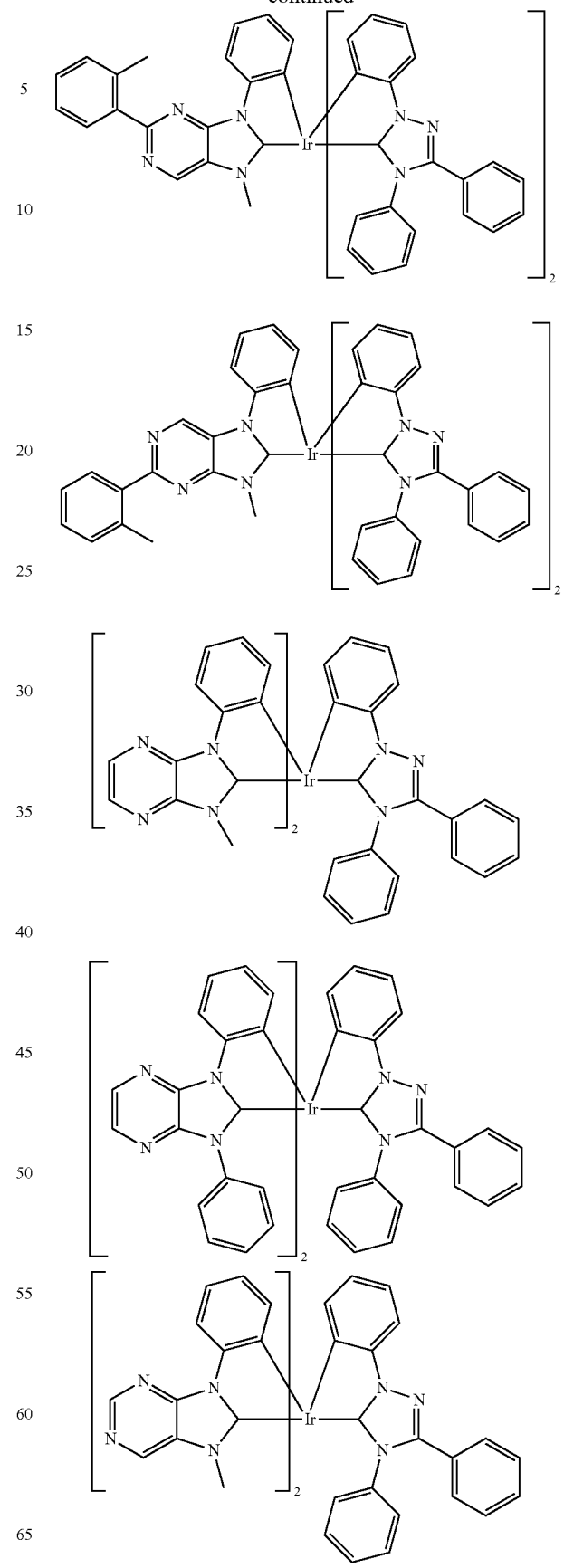

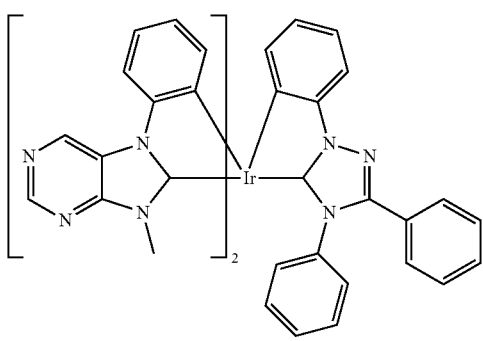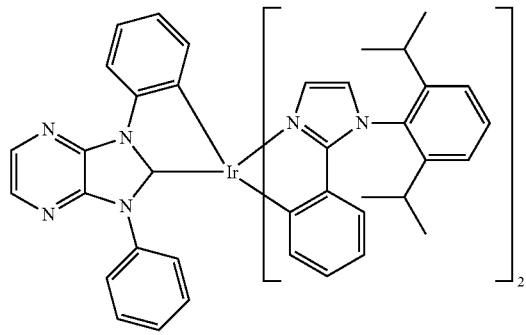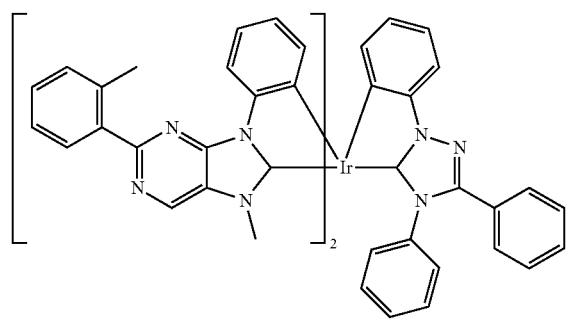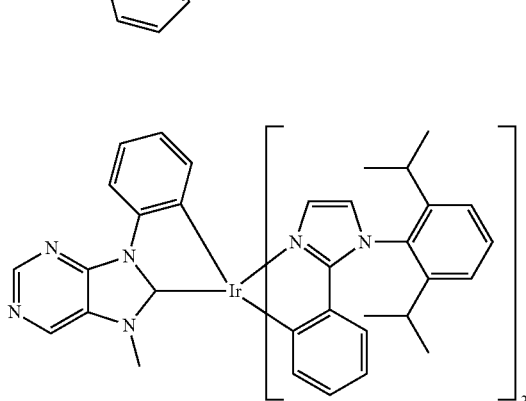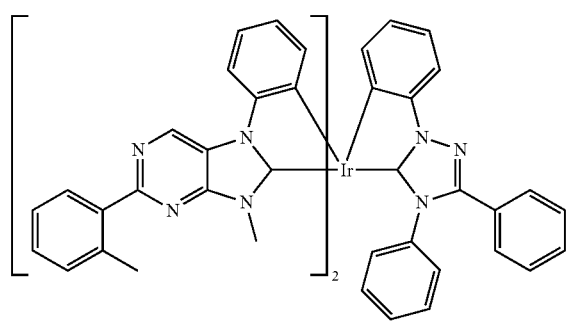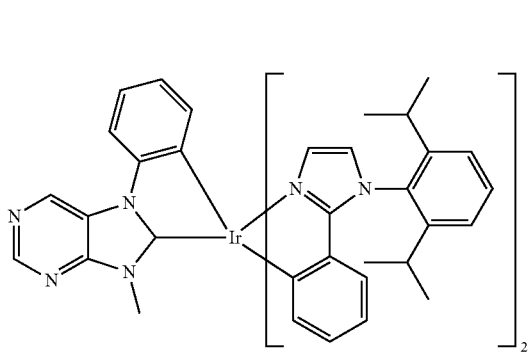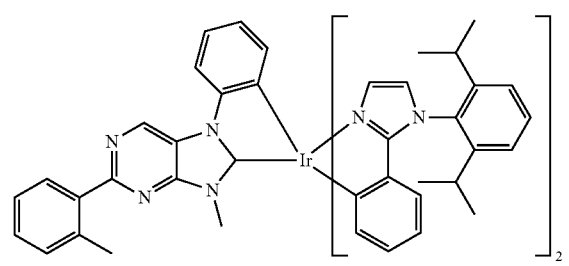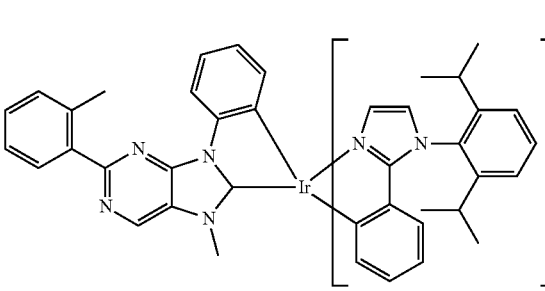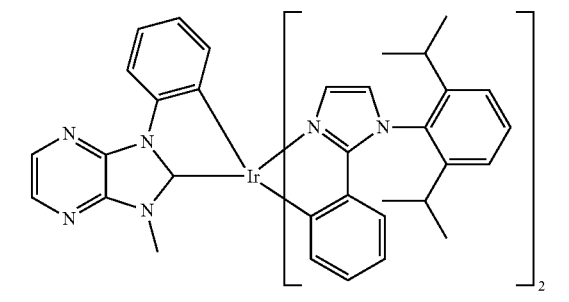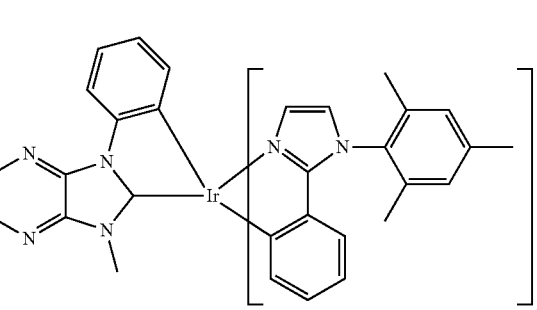

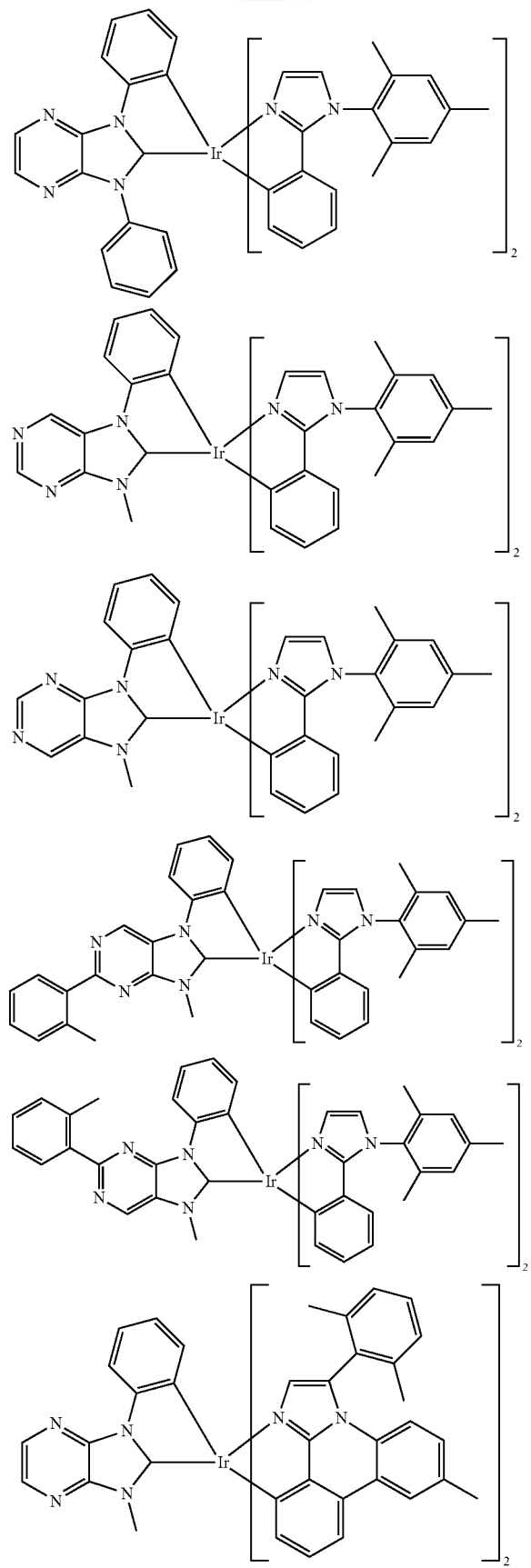
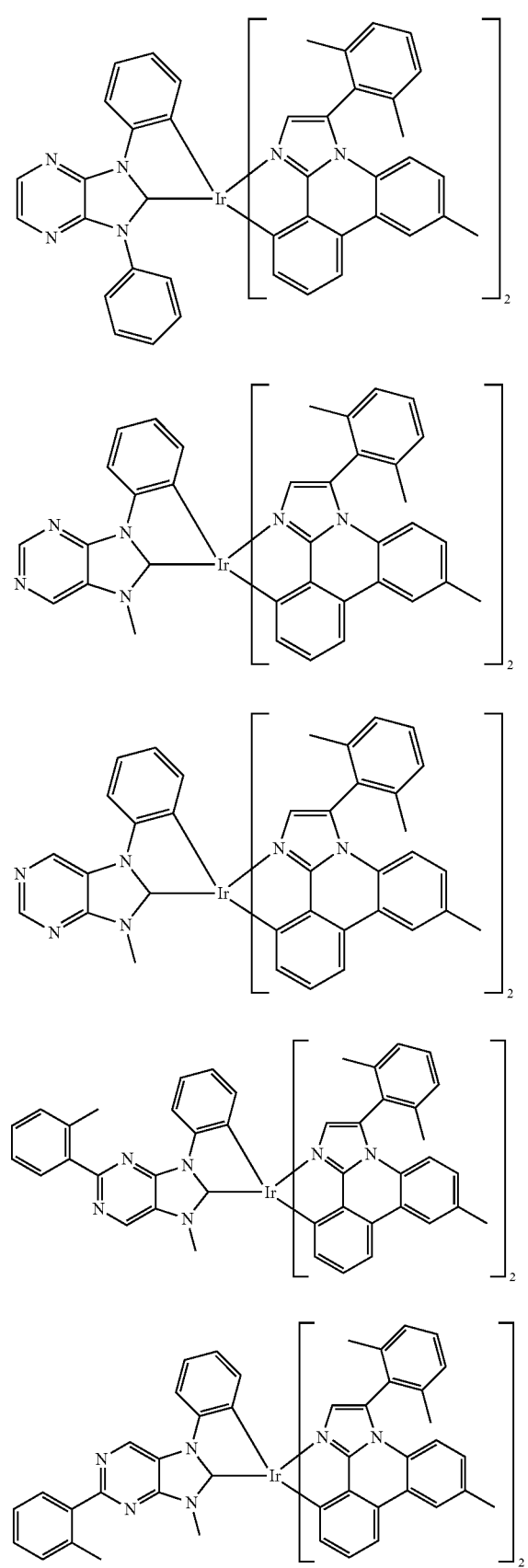

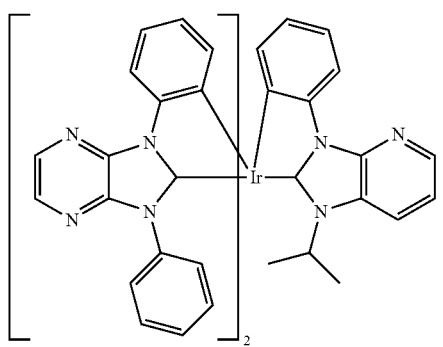
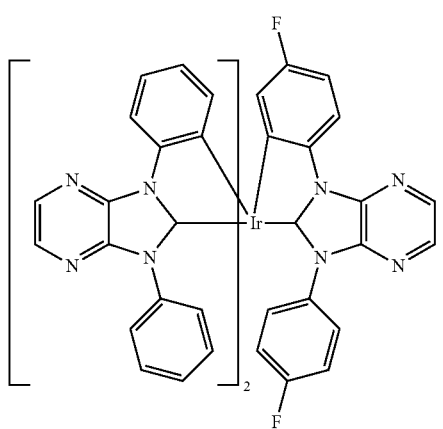
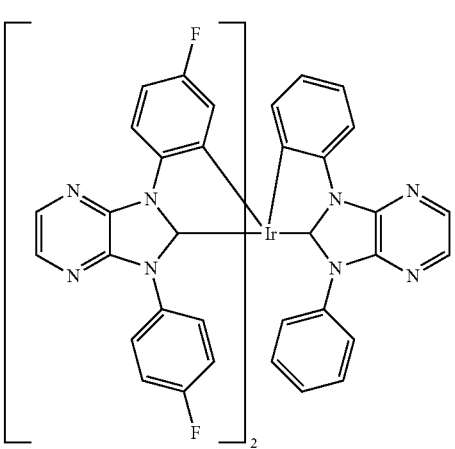
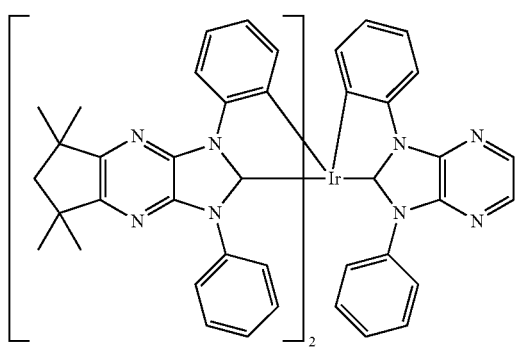
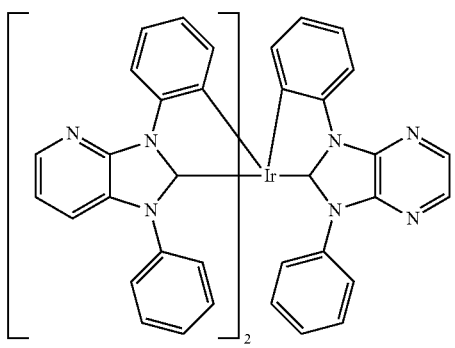
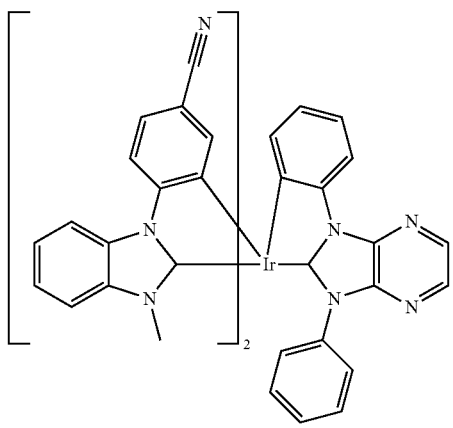
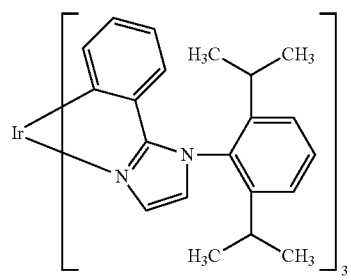
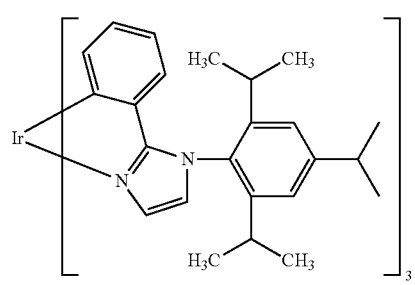
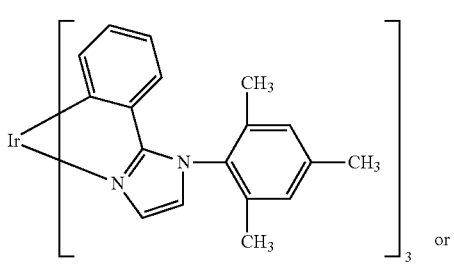

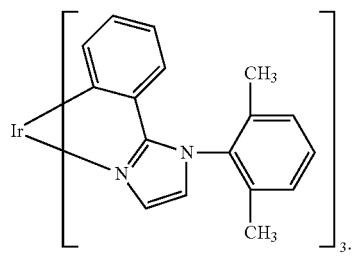

The homoleptic metal-carbene complexes may be present in the form of facial or meridional isomers, preference being given to the facial isomers.

In the case of the heteroleptic metal-carbene complexes, four different isomers may be present, preference being given to the pseudo-facial isomers.

Further suitable metal complexes are the commercially available metal complexes tris(2-phenylpyridine)iridium (III), iridium(III)tris(2-(4-tolyl)pyridinato-N,C$^{2'}$), bis(2-phenylpyridine)(acetylacetonato)iridium(III), iridium(III)tris(1-phenylisoquinoline), iridium(III) bis(2,2'-benzothienyl)pyridinato-N,C$^{3'}$)(acetylacetonate), tris(2-phenylquinoline)iridium(III), iridium(III)bis(2-(4,6-difluorophenyl)pyridinato-N,C$^2$)picolinate, iridium(III)bis(1-phenylisoquinoline)(acetylacetonate), bis(2-phenylquinoline)(acetylacetonato)iridium(III), iridium(III)bis(di-benzo[f,h]quinoxaline)(acetylacetonate), iridium(III)bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetylacetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-yl-yridine)(acetylacetonato)iridium(III).

In addition, the following commercially available materials are suitable: tris(dibenzoylacetonato)mono(phenanthroline)europium(III), tris(dibenzoylmethane)mono(phenanthroline)europium(III), tris(dibenzoylmethane)mono(5-aminophenanthroline)europium(III), tris(di-2-naphthoylmethane)mono(phenanthroline)europium(III), tris(4-bromobenzoylmethane)mono(phenanthroline)europium(III), tris(di(biphenyl)methane)mono(phenanthroline)europium(III), tris(dibenzoylmethane)mono(4,7-diphenylphenanthroline)europium(III), tris(dibenzoylmethane)mono(4,7-dimethylphenanthroline)europium(III), tris(dibenzoylmethane)mono(4,7-dimethylphenanthrolinedisulfonic acid)europium(III) disodium salt, tris[di(4-(2-(2-ethoxyethoxy)ethoxy)benzoylmethane)]mono(phenanthroline)europium(III) and tris[di[4-(2-(2-ethoxyethoxy)ethoxy)benzoylmethane)]mono(5-aminophenanthroline)europium(III), osmium(II) bis(3-(trifluoromethyl)-5-(4-tert-butylpyridyl)-1,2,4-triazolato) diphenylmethylphosphine, osmium(II)bis(3-(trifluoromethyl)-5-(2-pyridyl)-1,2,4-triazole) dimethylphenylphosphine, osmium(II)bis(3-(trifluoromethyl)-5-(4-tert-butylpyridyl)-1,2,4-triazolato) dimethylphenylphosphine, osmium(II)bis(3-(trifluoromethyl)-5-(2-pyridyl)pyrazolato) dimethylphenylphosphine, tris[4,4'-di-tert-butyl(2,2')-bipyridine]ruthenium(III), osmium(II)bis(2-(9,9-dibutylfluorenyl)-1-isoquinoline(acetylacetonate).

Suitable triplet emitters are, for example, carbene complexes. In one embodiment of the present invention, the compounds of the formula X are used in the light-emitting layer as matrix material together with carbene complexes as triplet emitters.

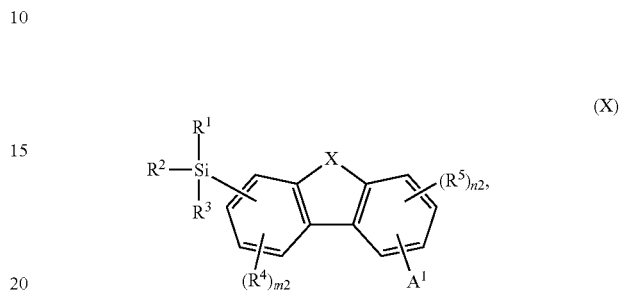

wherein

X is NR, S, O or PR;

R is aryl, heteroaryl, alkyl, cycloalkyl, or heterocycloalkyl;

A$^1$ is —NR$^6$R$^7$, —P(O)R$^8$R$^9$, —PR$^{10}$R$^{11}$, —S(O)$_2$R$^{12}$, —S(O)R$^{13}$, —SR$^{14}$, or —OR$^{15}$;

R$^1$, R$^2$ and R$^3$ are independently of each other aryl, heteroaryl, alkyl, cycloalkyl, or heterocycloalkyl, wherein at least on of the groups R$^1$, R$^2$, or R$^3$ is aryl, or heteroaryl;

R$^4$ and R$^5$ are independently of each other alkyl, cycloalkyl, heterocycloalkyl, aryl, heteroaryl, a group A, or a group having donor, or acceptor characteristics;

n2 and m2 are independently of each other 0, 1, 2, or 3;

R$^6$, R$^7$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and R$^8$, R$^9$, R$^{10}$, R$^{11}$, R$^{12}$, R$^{13}$, R$^{14}$ and R$^{15}$ are independently of each other aryl, heteroaryl, alkyl, cycloalkyl, or heterocycloalkyl. Compounds of formula X, such as, for example,

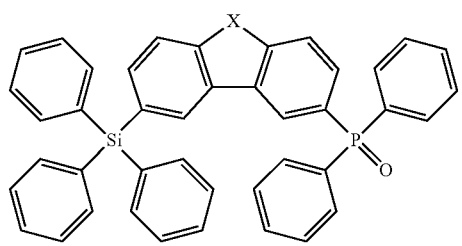

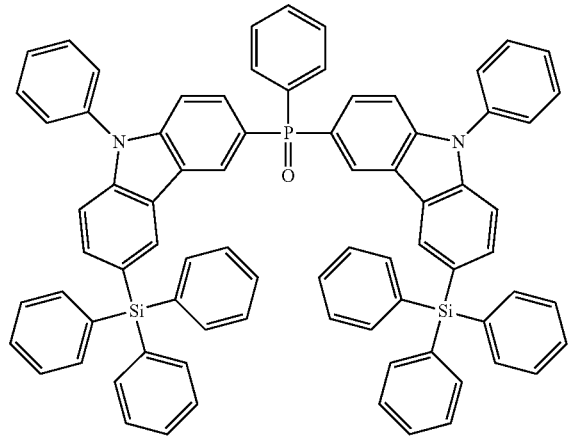
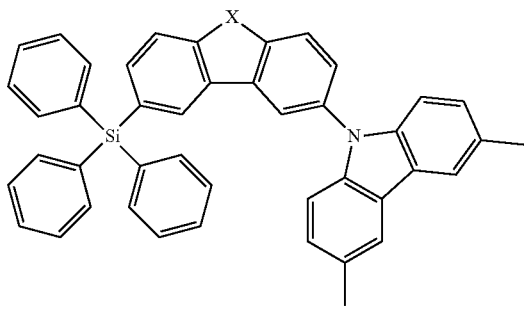
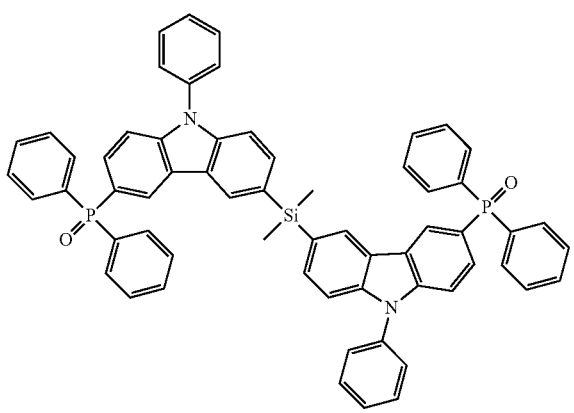
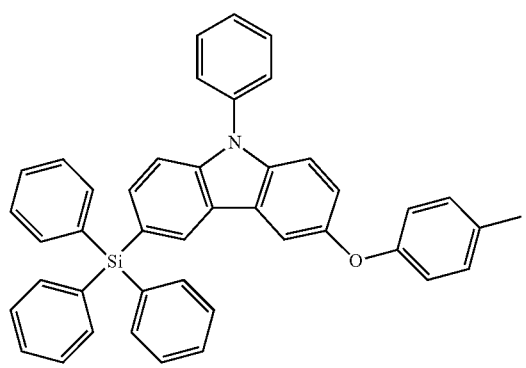
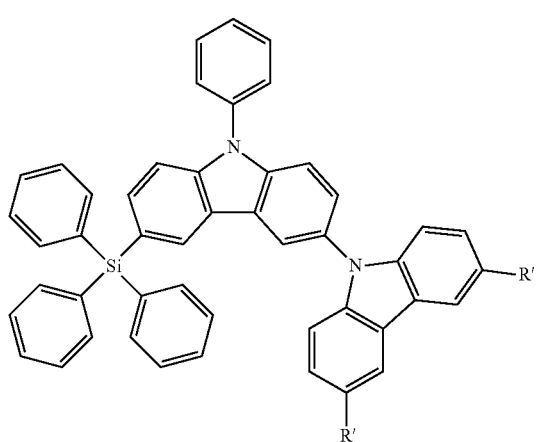
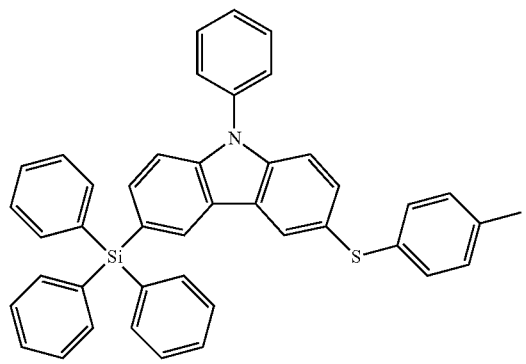
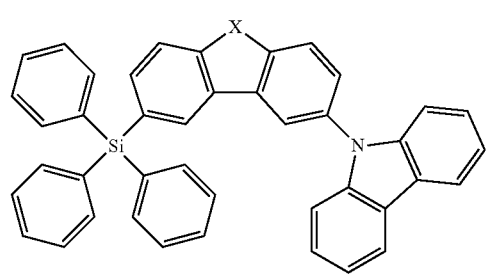
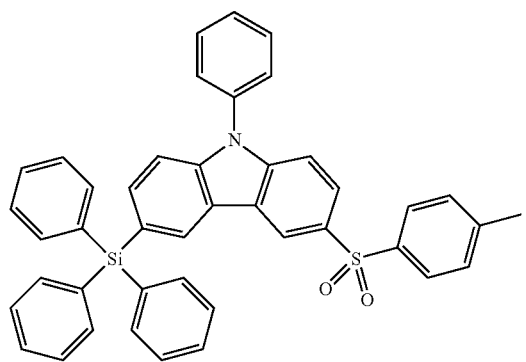

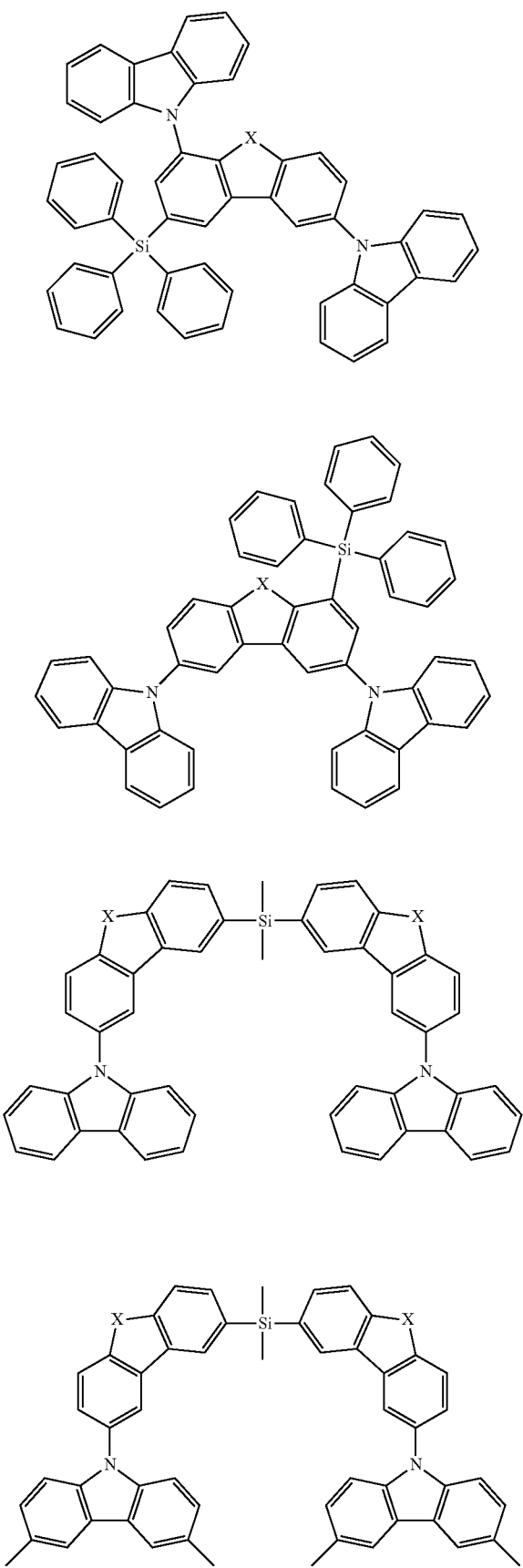
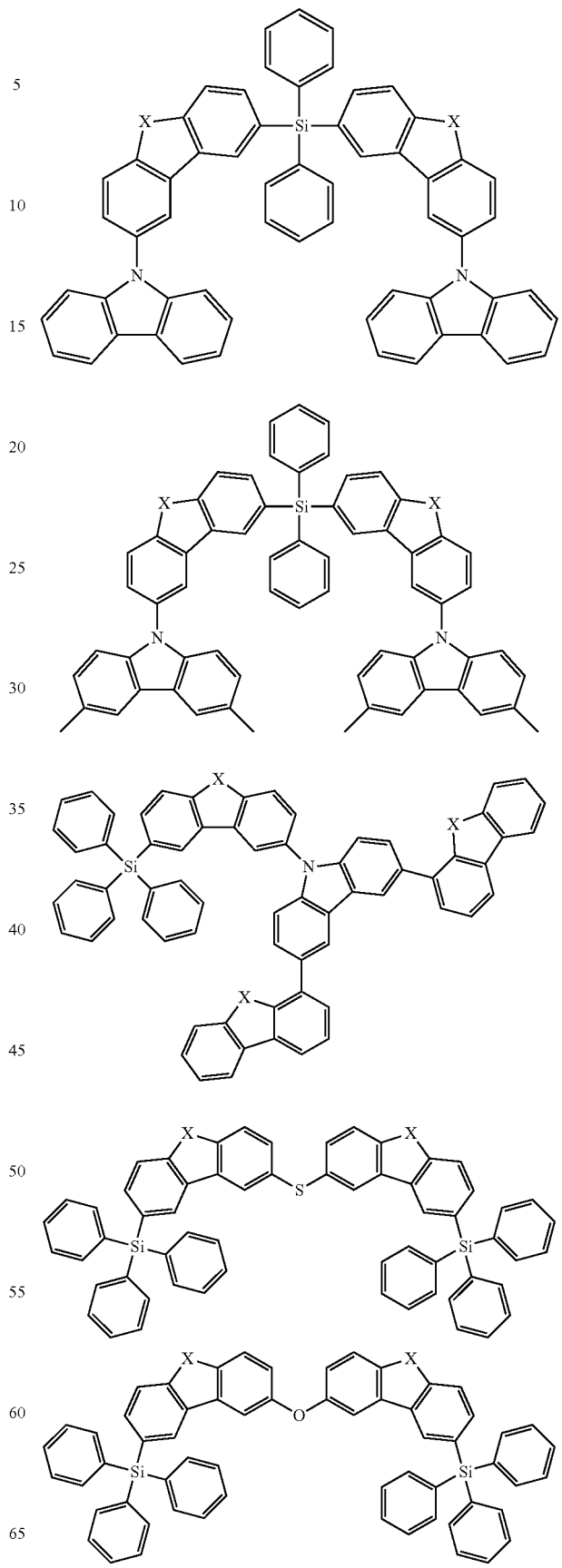

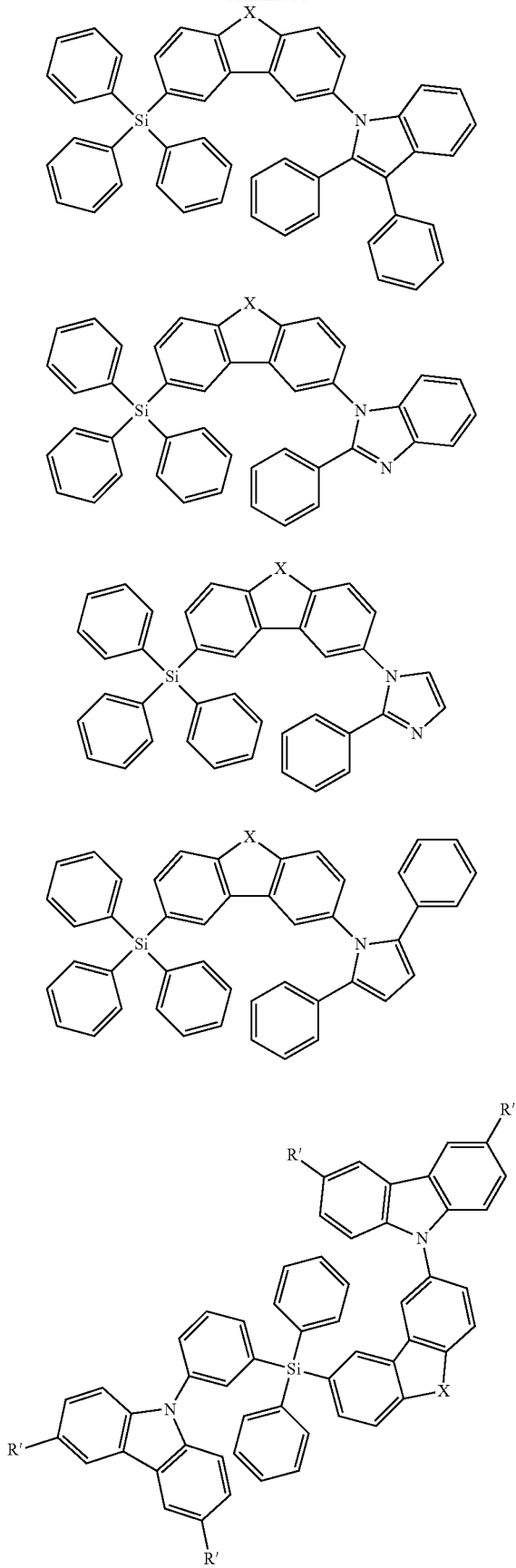
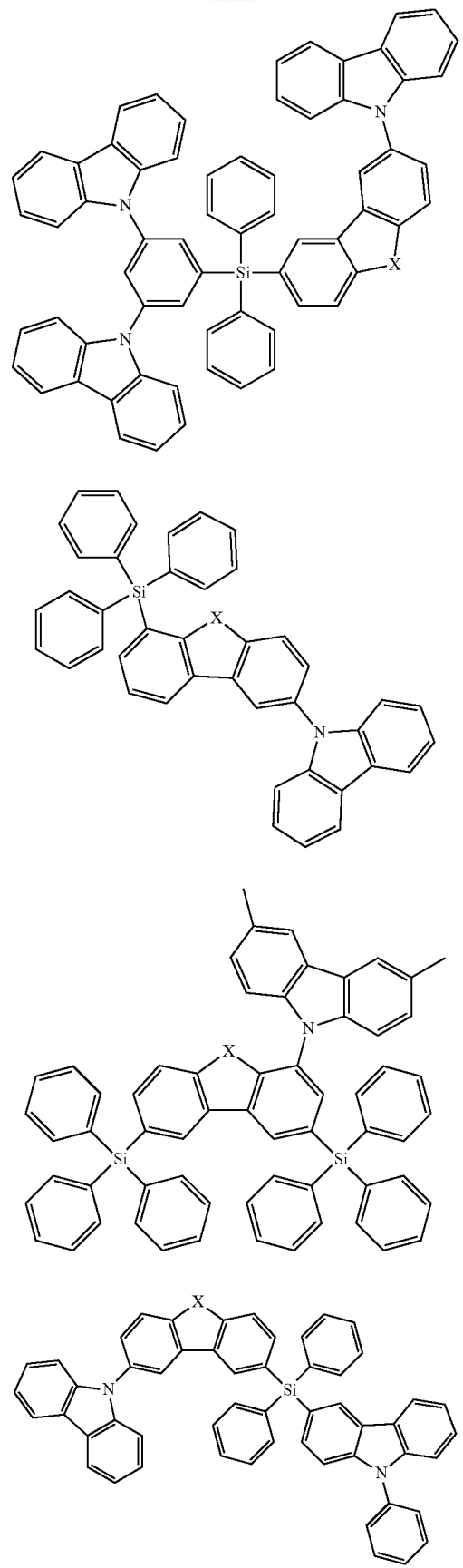

59
-continued
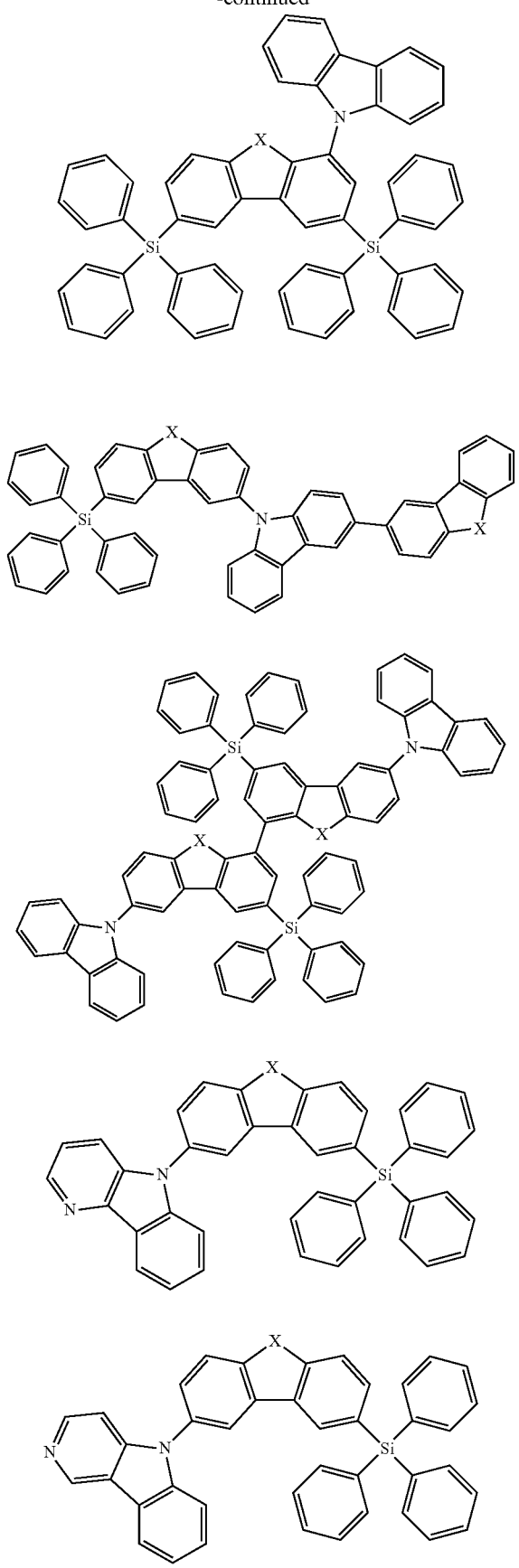
60
-continued
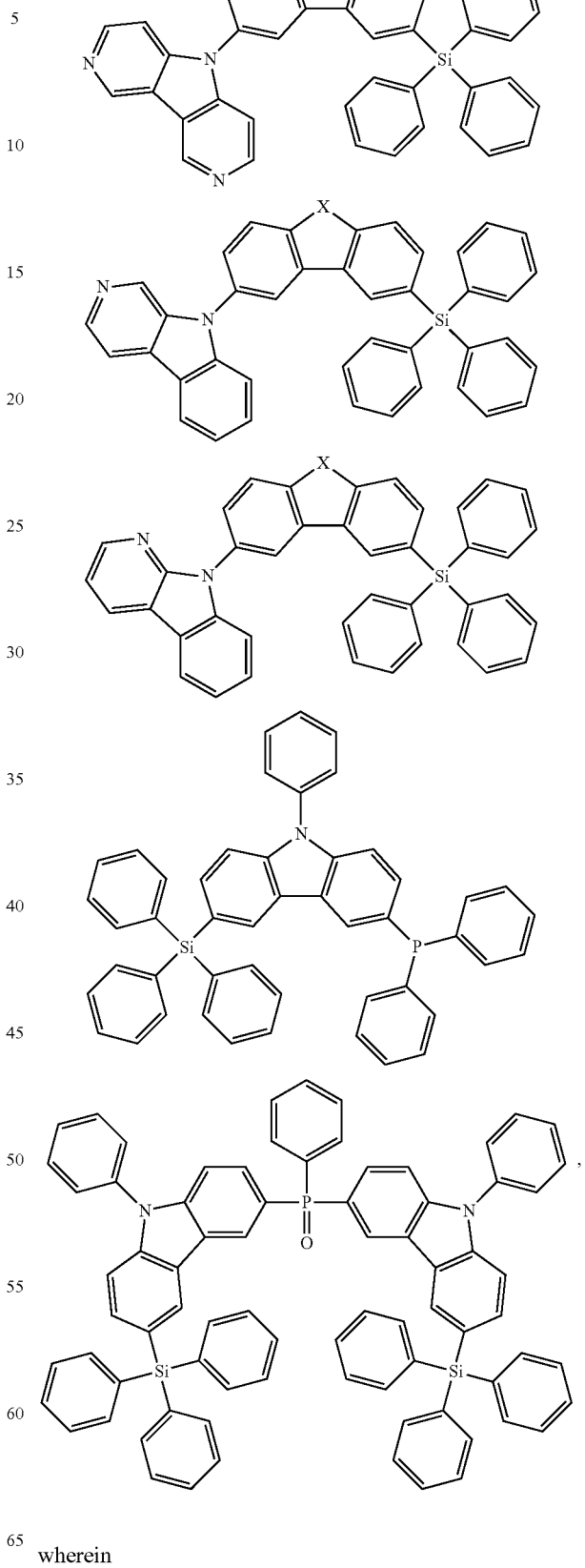
wherein
X is S, or O, and R' is H, or CH$_3$;

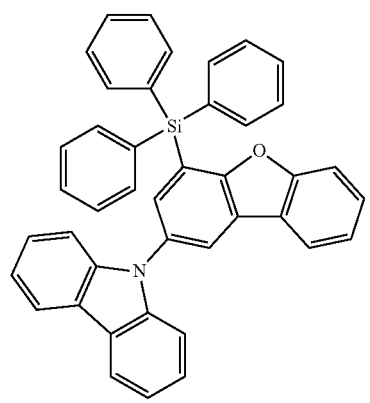
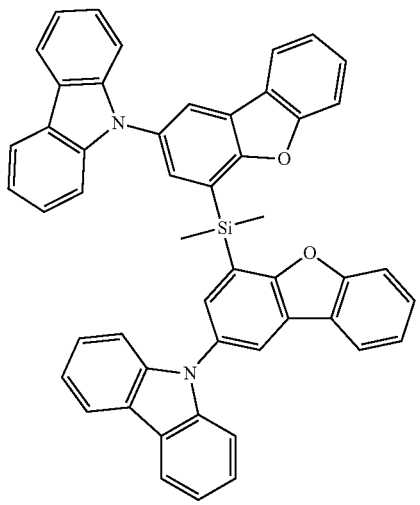
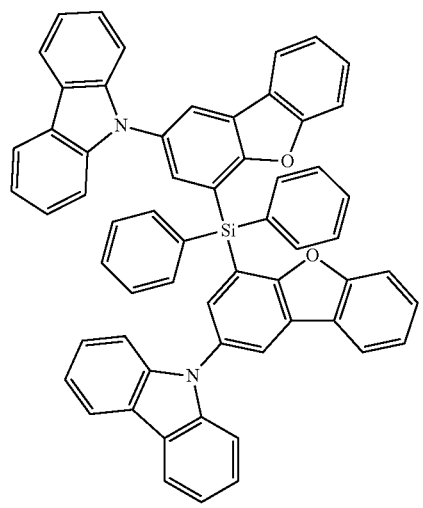
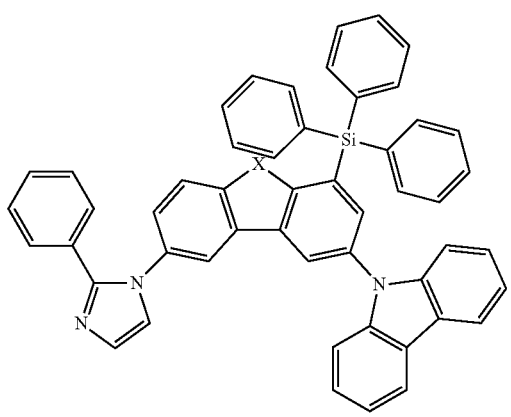
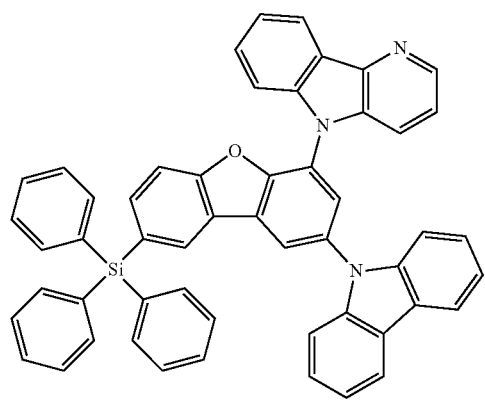
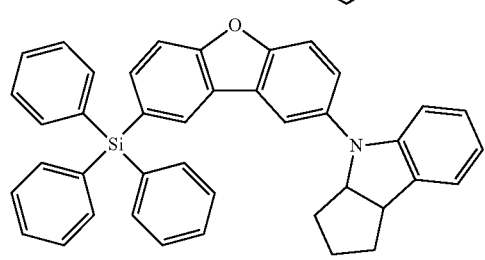

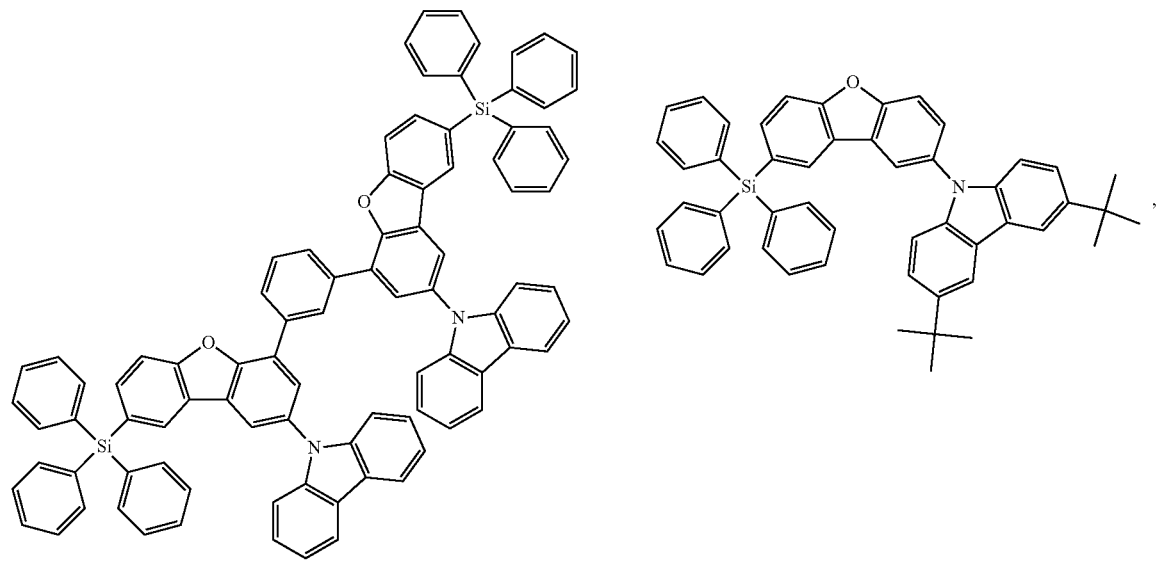
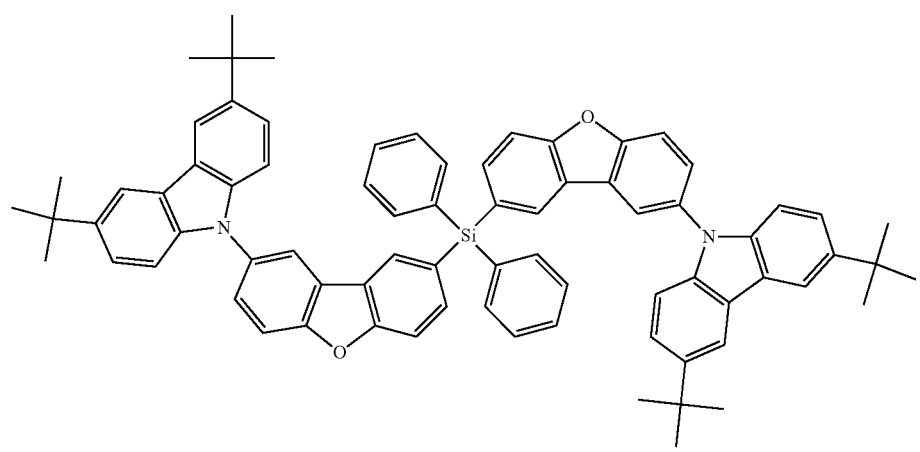
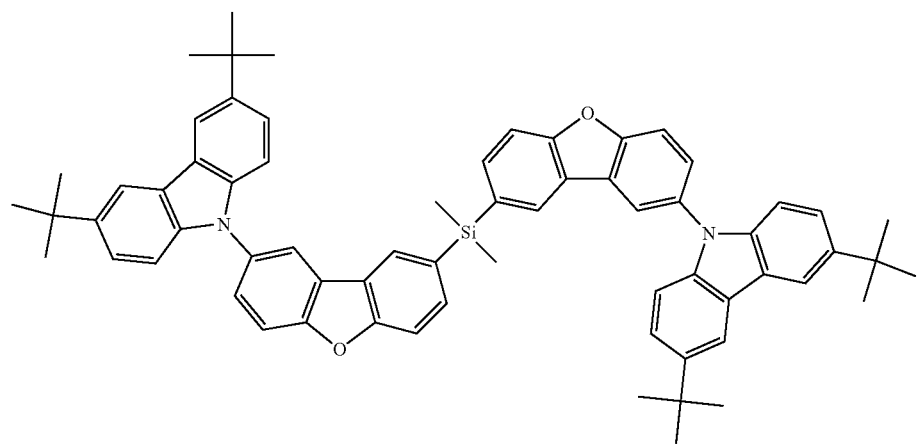

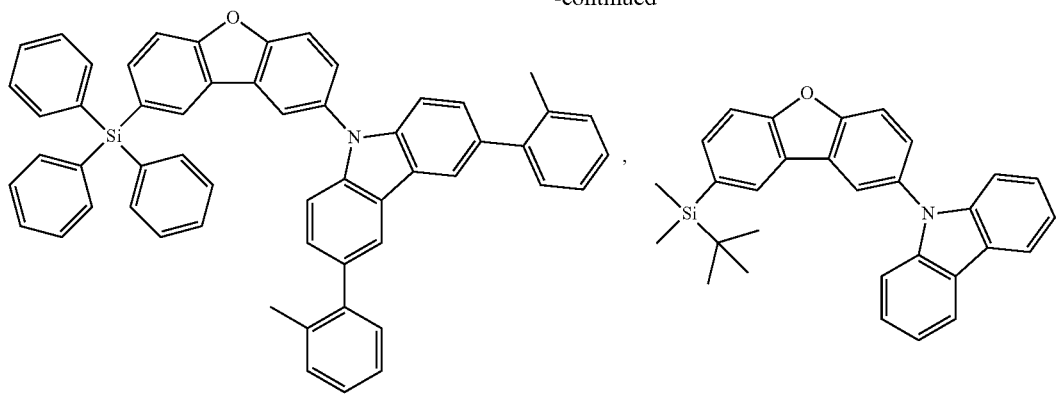
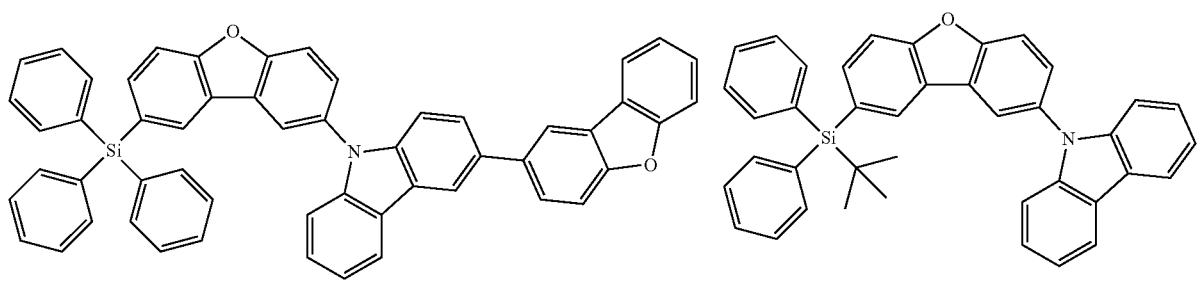
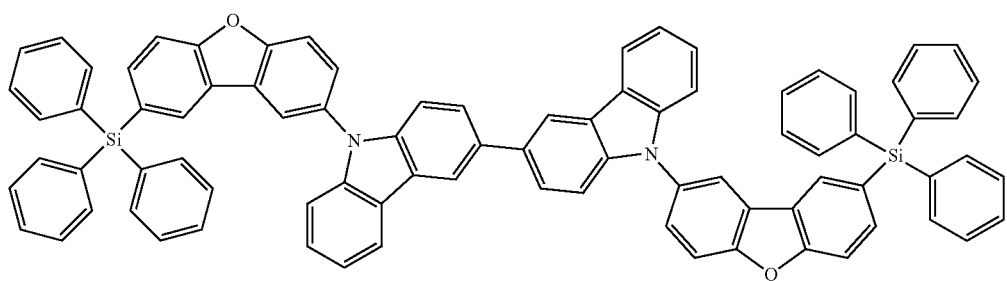
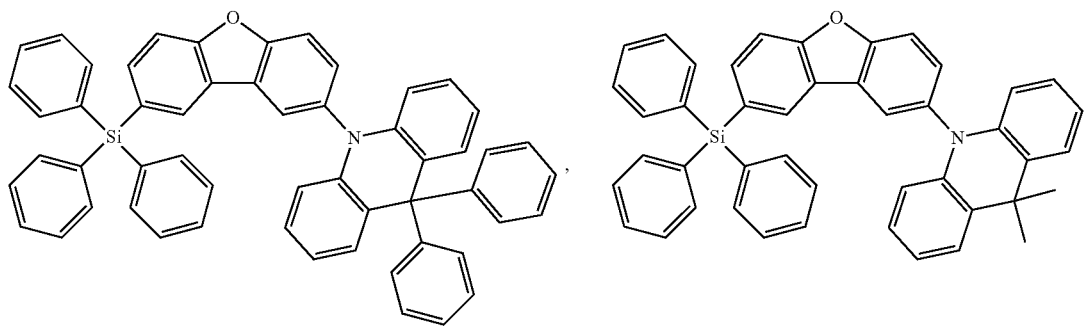
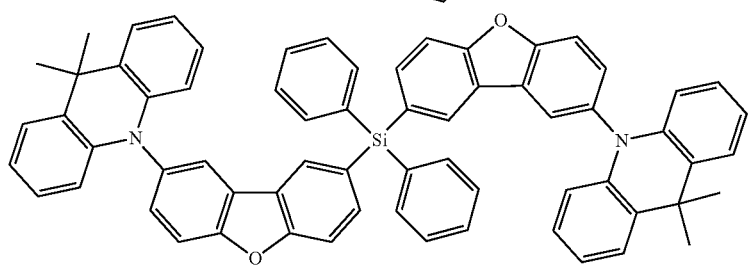

-continued
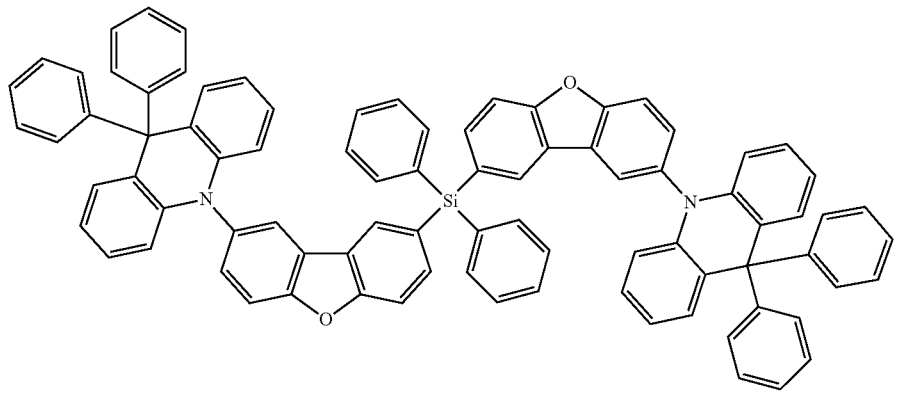
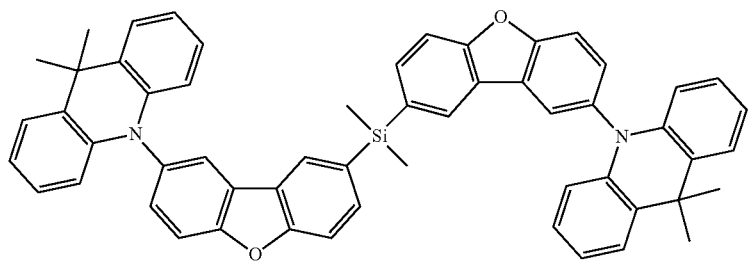
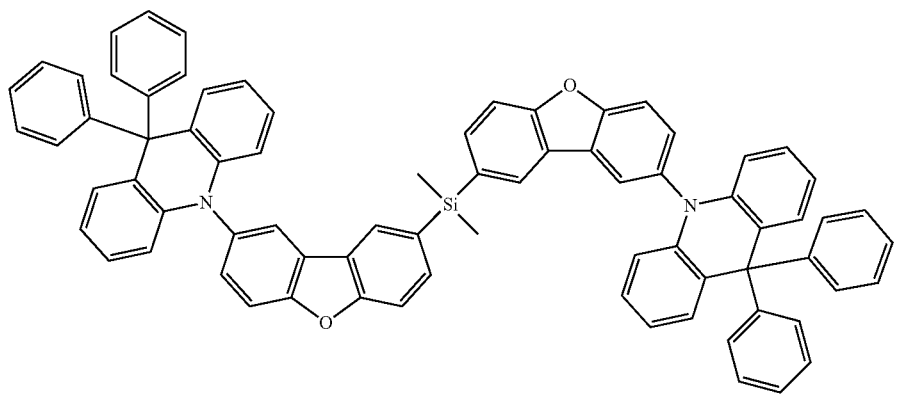
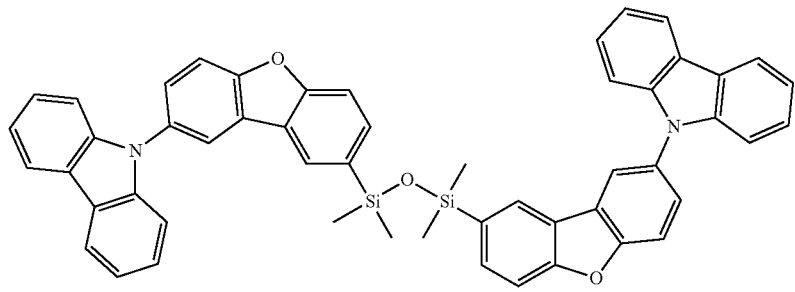

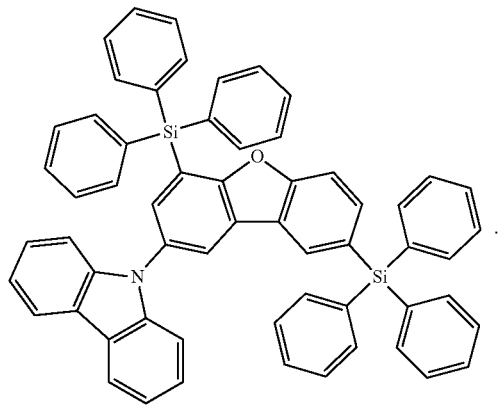
are described in WO2010/079051.
In addition, dibenzofuranes described, for example, in U.S.2009066226, EP1885818B1, EP1970976, EP1998388, EP2034538, U.S.2007/0224446A1, WO2009/069442A1, WO2010/090077A1 and JP 2006/321750A are suitable as matrix materials.
Examples of preferred matrix materials are shown below:
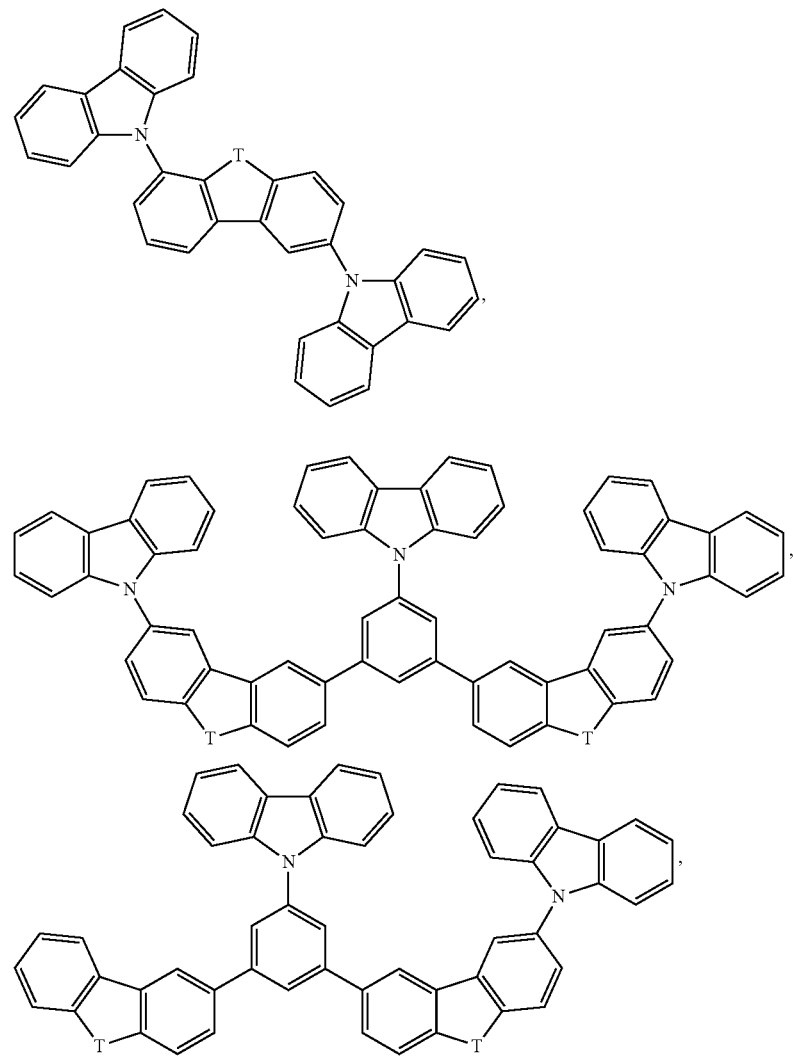

-continued
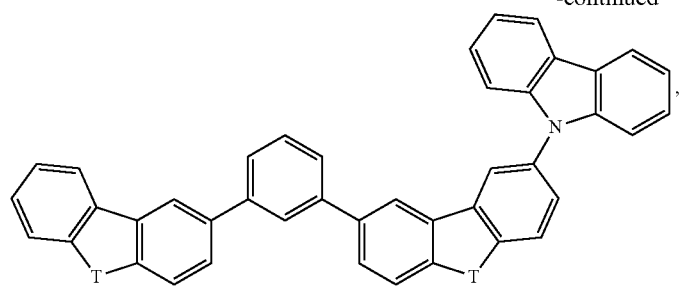
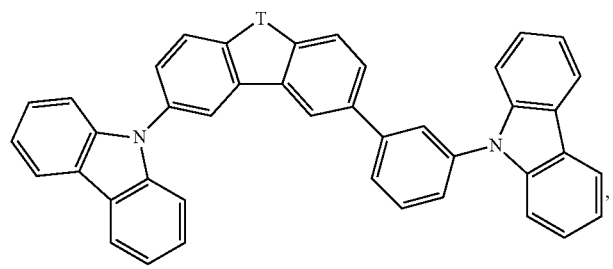
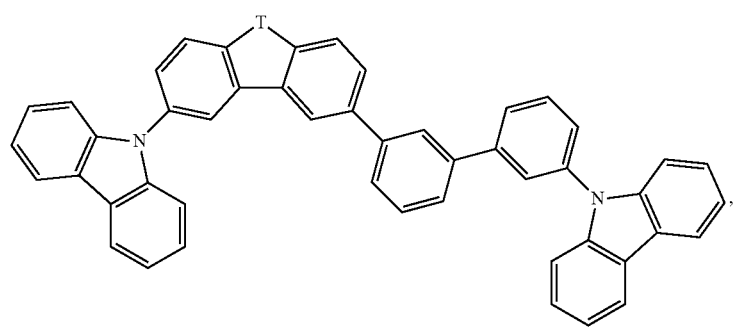
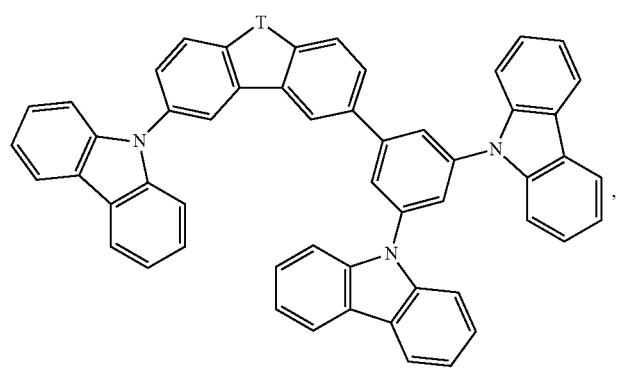
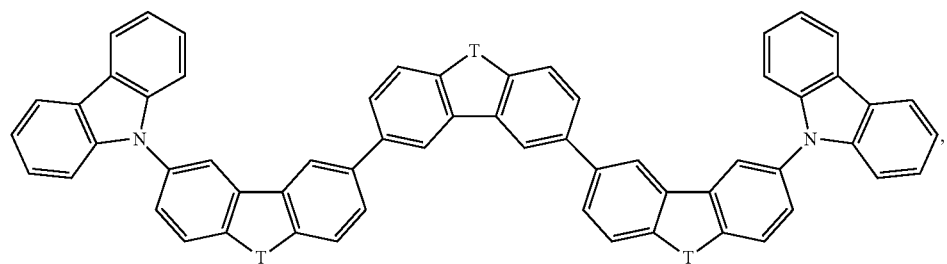

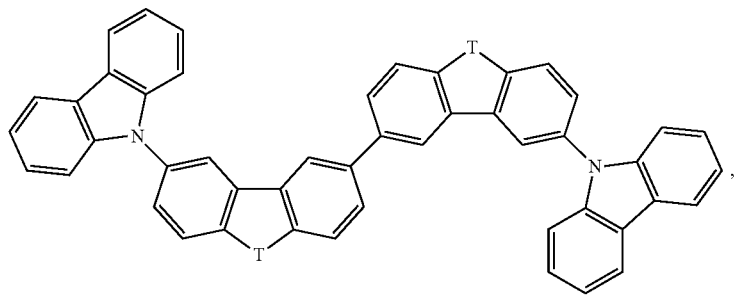
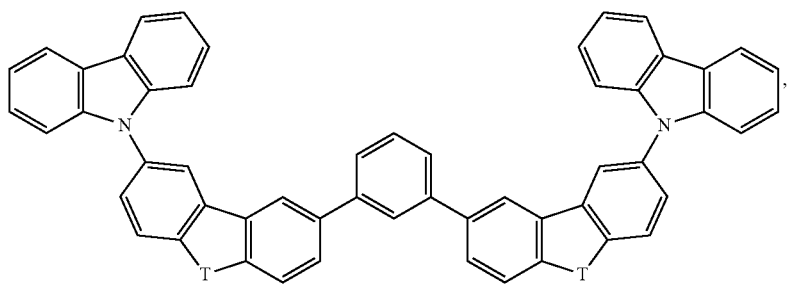
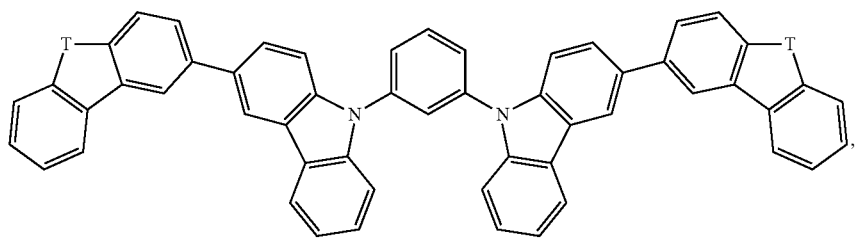
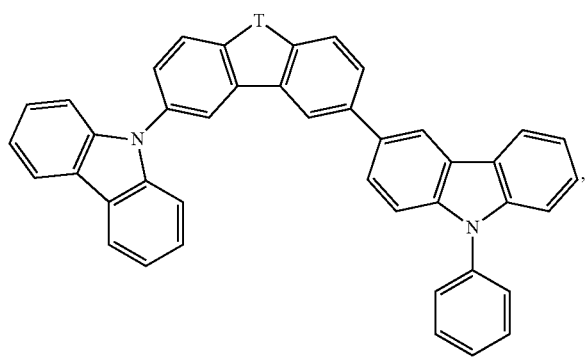
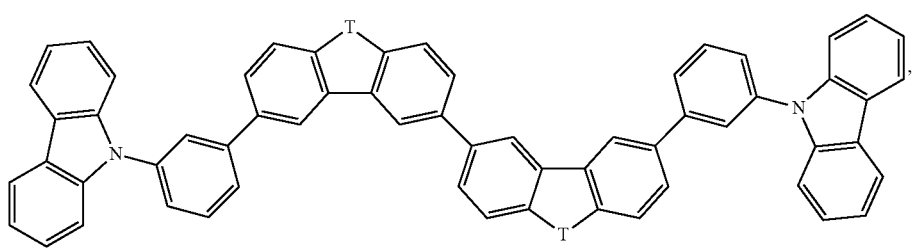

-continued
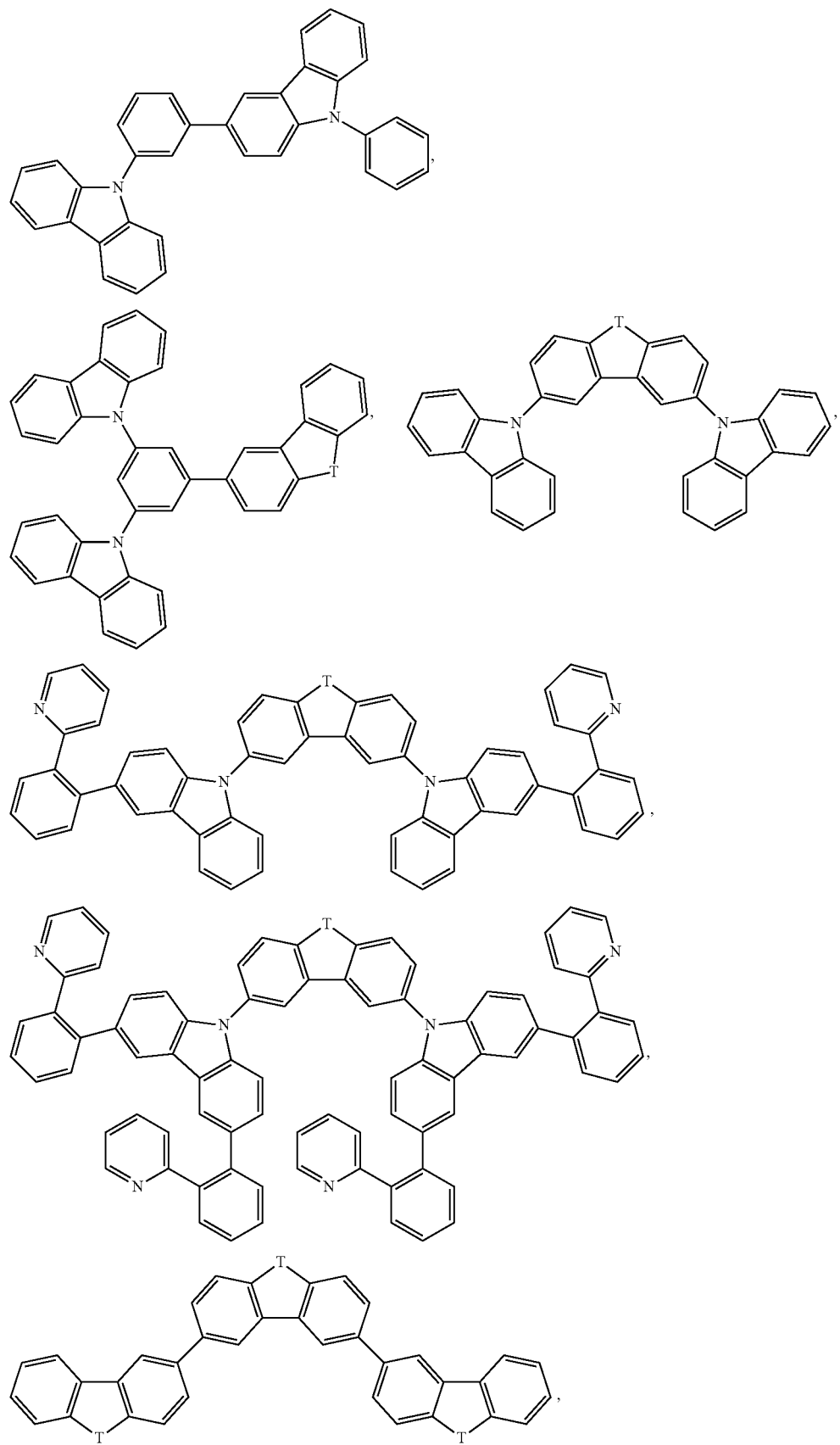

-continued

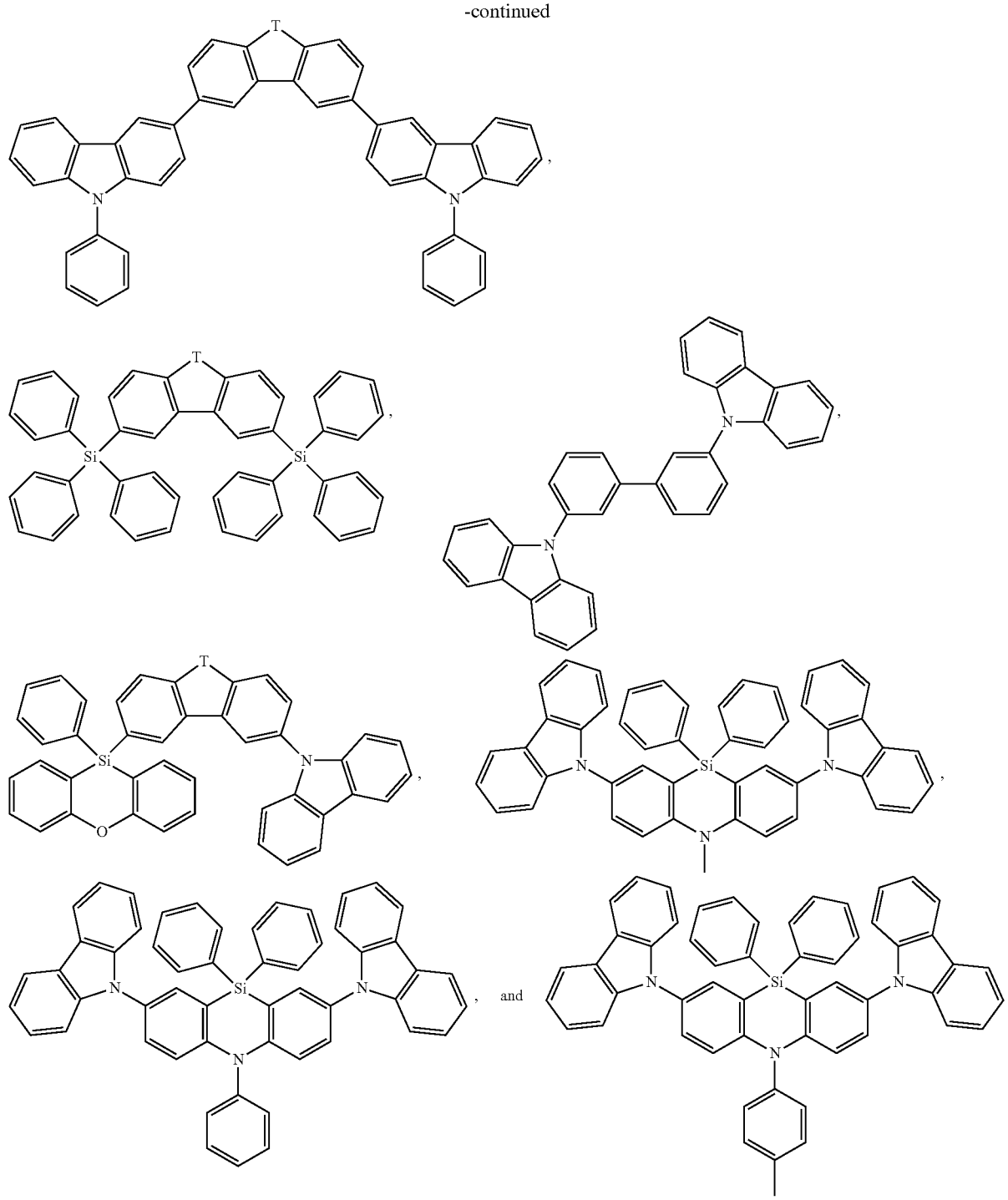

In the above-mentioned compounds T is O, or S, preferably O. If T occurs more than one time in a molecule, all groups T have the same meaning.

Suitable carbene complexes are known to those skilled in the art and are described, for example, in WO 2005/019373 A2, WO 2006/056418 A2, WO 2005/113704, WO 2007/115970, WO 2007/115981 and WO 2008/000727.

The light-emitting layer may comprise further components in addition to the emitter material. For example, a fluroescent dye may be present in the light-emitting layer in order to alter the emission color of the emitter material. In addition—in a preferred embodiment—a matrix material can be used. This matrix material may be a polymer, for example poly(N-vinyl-carbazole) or polysilane. The matrix material may, however, be a small molecule, for example 4,4'-N,N'-dicarbazolebiphenyl (CDP=CBP) or tertiary aromatic amines, for example TCTA. In a preferred embodiment of the present invention, at least one compound of the formula X is used as matrix material.

In a preferred embodiment, the light-emitting layer is formed from 2 to 40% by weight, preferably 5 to 35% by weight, of at least one of the aforementioned emitter materials and 60 to 98% by weight, preferably 65 to 95% by weight, of at least one of the aforementioned matrix materials—in one embodiment at least one compound of the formula X—where the sum total of the emitter material and of the matrix material adds up to 100% by weight.

In a preferred embodiment, the light-emitting layer comprises a compound of formula X, such as, for example,

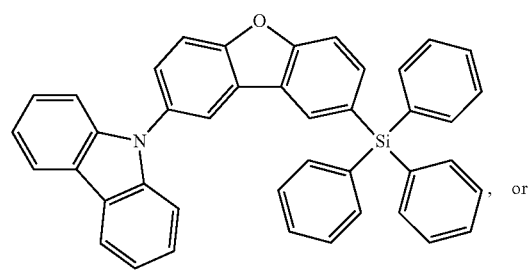

, or

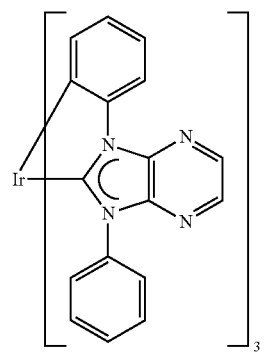

and 60 to 98% by weight, preferably 65 to 95% by weight, of a compound of the formula X and

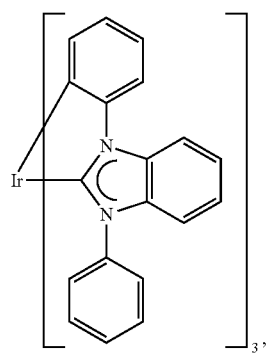

where the sum total of the carben complexes and of the compound of formula X adds up to 100% by weight.

In a further embodiment, the compounds of the formula X are used as hole/exciton blocker material, preferably together with carbene complexes as triplet emitters. The compounds of the formula X may be used as matrix materials or both as matrix materials and as hole/exciton blocker materials together with carbene complexes as triplet emitters.

Suitable metal complexes for use together with the compounds of the formula X as matrix material and/or hole/exciton blocker material, in OLEDs are thus, for example, also carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application.

Hole blocker materials typically used in OLEDs are compounds of formula X, 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-conducting material. Further suitable hole blockers and/or electron transport materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, and two carbene complexes, preferably of formula

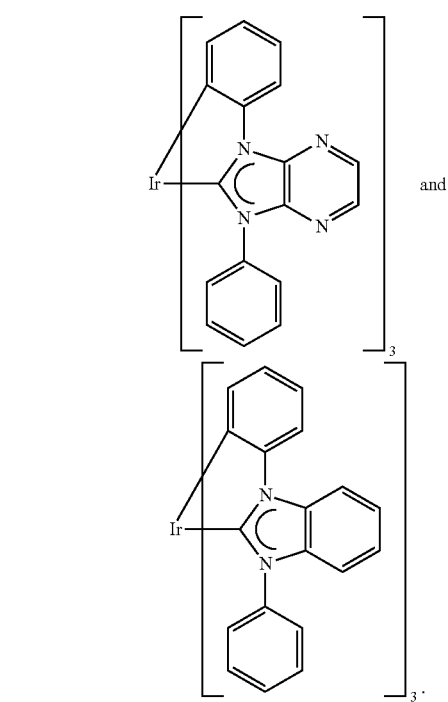

In said embodiment, the light-emitting layer is formed from 2 to 40% by weight, preferably 5 to 35% by weight, of 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f]-[1,10]-phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylben-zothiophene S-oxides and disilylben-zothiophene S,S-dioxides, as specified, for example, in WO2009003919 (PCT/EP2008/058207) and WO2009003898 (PCT/EP2008/058106) and disilyl compounds as disclosed in WO2008/034758, as a blocking layer for holes/excitons (4) or as matrix materials in the light-emitting layer (3).

In addition—in one embodiment—it is possible to use carbene complexes as hole transport materials, the band gap of the at least one hole transport material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is fac-Iridium-tris(1,3-diphenylbenzimidazolin-2-yliden-C,C$^{2I}$) (Ir(dpbic)$_3$) with the formula:

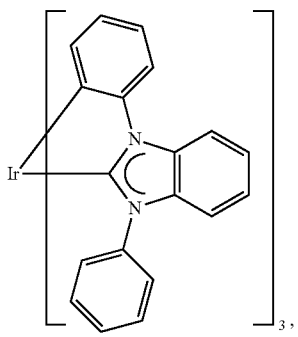

which is disclosed, for example, in WO2005/019373. Preferably, the hole transport layer comprises Ir(dpbic)$_3$ doped with molybdenum oxide (MoO$_x$), especially MoO$_3$, or rhenium oxide (ReO$_x$), especially ReO$_3$. The dopant is contained in an amount of from 0.1% by weight, preferably 1 to 8% by weight, more preferably 3 to 5% by weight, based on the amount of dopant and carbene complex.

In a preferred embodiment, the present invention relates to an inventive OLED comprising the layers (1) anode, (2) hole transport layer, (3) light-emitting layer, (4) blocking layer for holes/excitons, (5) electron transport layer and (6) cathode, and if appropriate further layers, wherein the electron transport layer comprises the compounds of formula I, or II.

The electron transport layer (5) of the inventive OLEDs comprises the compounds of formula I, or II. The layer (5) preferably improves the mobility of the electrons.

Among the materials mentioned above as hole transport materials and electron transport materials, some may fulfil several functions. For example, some of the electron-transporting materials are simultaneously hole-blocking materials when they have a low-lying HOMO. These can be used, for example, in the blocking layer for holes/excitons (4).

The charge transport layers can also be electronically doped in order to improve the transport properties of the materials used, in order firstly to make the layer thicknesses more generous (avoidance of pinholes/short circuits) and in order secondly to minimize the operating voltage of the device. For example, the hole transport materials can be doped with electron acceptors; for example, phthalocyanines or arylamines such as TPD or TDTA can be doped with tetrafluorotetracyanquinodimethane (F4-TCNQ) or with MoO$_3$ or WO$_3$. The electron transport materials can be doped, for example, with alkali metals, for example Alq3 with lithium. In addition, electron transports can be doped with salts such as Cs$_2$CO$_3$, or 8-hydroxyquinolato-lithium (Liq). Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo. Appl. Phys. Lett., Vol. 82, No. 25, 23 Jun. 2003 and Pfeiffer et al., Organic Electronics 2003, 4, 89-103. For example, the hole transport layer may, in addition to a carbene complex, e.g. Ir(dpbic)$_3$, be doped with MoO$_3$ or WO$_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the periodic table of the elements (old IUPAC version), comprising the lanthanides and actinides, for example samarium. In addition, it is also possible to use metals such as aluminum or indium, and combinations of all metals mentioned. In addition, alkali metal-comprising organometallic compounds, or alkali metal fluorides, such as, for example, LiF, CsF, or KF, can be applied between the organic layer and the cathode in order to reduce the operating voltage.

The OLED according to the present invention may additionally comprise further layers which are known to those skilled in the art. For example, a layer which facilitates the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to facilitate the transport of negative charge and/or to match the band gaps between the layers to one another. Alternatively, this layer may serve as a protective layer.

In a preferred embodiment, the inventive OLED, in addition to layers (1) to (6), comprises at least one of the following layers mentioned below:
  a hole injection layer between the anode (1) and the hole-transport layer (2);
  a blocking layer for electrons between the hole-transport layer (2) and the light-emitting layer (3);
  an electron injection layer between the electron-transport layer (5) and the cathode (6).

Materials for a hole injection layer may be selected from copper phthalocyanine, 4,4',4"-tris(N-3-methylphenyl-N-phenylamino)triphenylamine (m-MTDATA), 4,4',4"-tris(N-

(2-naphthyl)-N-phenylamino)triphenylamine (2T-NATA), 4,4',4''-tris(N-(1-naphthyl)-N-phenylamino)triphenylamine (1T-NATA), 4,4',4''-tris(N,N-diphenylamino)triphenylamine (NATA), titanium oxide phthalocyanine, 2,3,5,6-tetrafluoro-7,7,8,8-tetracyanoquino-dimethane (F4-TCNQ), pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di-[4-(N,N-ditolylamino)phenyl]benzidine (NTNPB), N,N'-diphenyl-N,N'-di-[4-(N,N-diphenylamino)phenyl]benzidine (NPNPB), N,N'-di(naphthalen-2-yl)-N,N'-diphenylbenzene-1,4-diamine (α-NPP). In principle, it is possible that the hole injection layer comprises at least one compound of the formula X as hole injection material.

As a material for the electron injection layer, CsF, KF, or lithium quinolate (Liq), for example, can be selected. CsF is more preferred than KF, or Liq.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semi-transports, typically ITO, or IZO, or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer have greater thicknesses than the layer thicknesses specified when they are electrically doped.

Use of the electron transport layer of the present application makes it possible to obtain OLEDs with high efficiency and with low operating voltage. Frequently, the OLEDs obtained by the use of the electron transport layer of the present application additionally have high lifetimes. The efficiency of the OLEDs can additionally be improved by optimizing the other layers of the OLEDs. Shaped substrates and novel hole-transport materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, MP3 players, vehicles and destination displays on buses and trains. Further devices in which the inventive OLEDs can be used are, for example, keyboards; items of clothing; furniture; wallpaper.

In addition, the electron transport layer of the present application can be used in OLEDs with inverse structure. The structure of inverse OLEDs and the materials typically used therein are known to those skilled in the art. In addition, the present invention relates to an apparatus selected from the group consisting of stationary visual display units such as visual display units of computers, televisions, visual display units in printers, kitchen appliances and advertising panels, illuminations, information panels, and mobile visual display units such as visual display units in cellphones, laptops, digital cameras, MP3 players, vehicles and destination displays on buses and trains; illumination units; keyboards; items of clothing; furniture; wallpaper, comprising the inventive organic electronic device, or the inventive organic layer, especially electron transport layer.

The following examples are included for illustrative purposes only and do not limit the scope of the claims. Unless otherwise stated, all parts and percentages are by weight.

EXAMPLES

Example 1

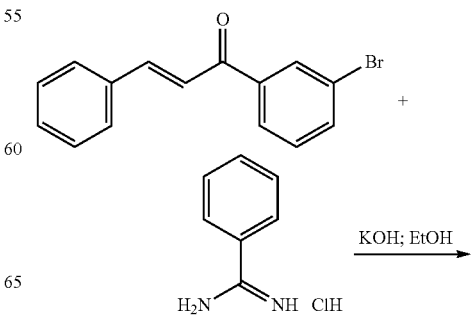

-continued

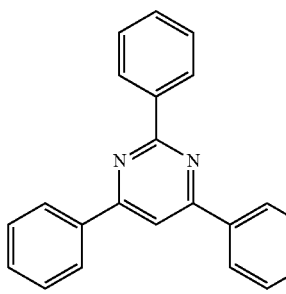

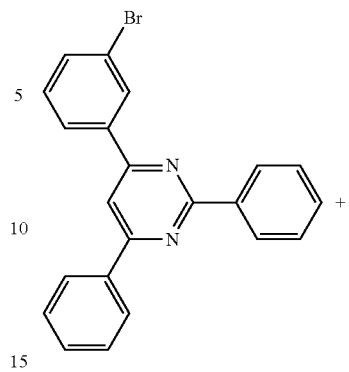

a) 5.45 g (34.8 mmol) benzamidine hydrochloride hydrate and 4.10 g (73.1 mmol) potassium carbonate in 50 ml ethanol are stirred at 90° C. under dry air. 20.0 g (69.7 mmol) (E)-1-(3-bromophenyl)-3-phenyl-prop-2-en-1-one in 20 ml hot ethoxy-ethanol are added slowly. After 24 h the reaction mixture is cooled to 25° C., the product is filtered off, washed with ethanol, water and again ethanol and is used without further purification in step b) (yield 7.84 g (58%)).

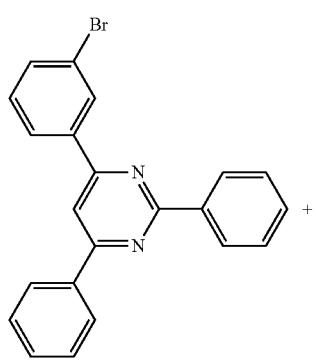

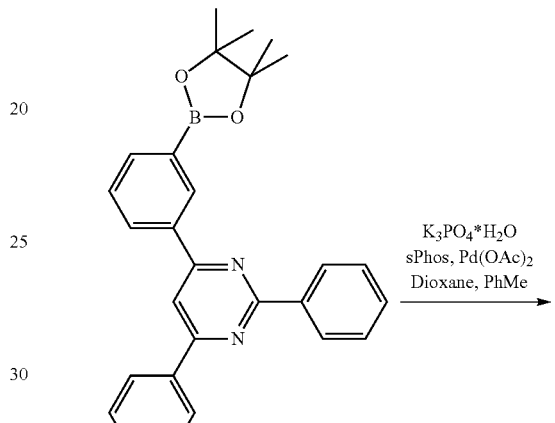

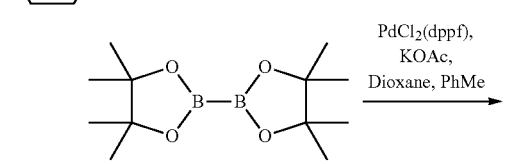

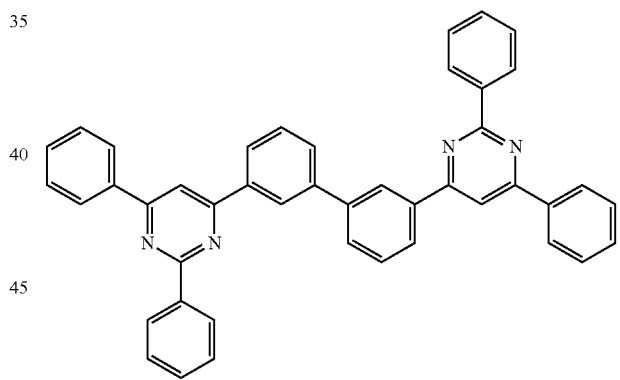

b) 5.20 g (13.4 mmol) 4-(3-bromophenyl)-2,6-diphenyl-pyrimidine, 8.18 g (32.2 mmol) 4,4,5,5-tetramethyl-2-(4,4,5,5-tetramethyl-1,3,2-dioxaborolan-2-yl)-1,3,2-dioxaborolane and 7.91 g (80.6 mmol) potassium acetate are degassed with argon. 60 ml DMF are added and the mixture is degassed with argon. 120 mg (0.16 mmol) PdCl₂(dppf) (1,1'-bis(diphenylphosphino)ferrocene-palladium(II)dichloride) are added. The reaction mixture is stirred at 60° C. for 26 h, poured on ice and the product is filtered off.

c) 5.55 g (12.8 mmol) of the product of example 1a, 4.50 g (11.6 mmol) 4-(3-bromophenyl)-2,6-diphenyl-pyrimidine and 14.1 g (58.1 mmol) potassium phosphate tribasic monohydrate are degassed with argon. 40 ml dioxane,100 ml toluene and 25 ml water are added. The mixture is degassed with argon. 286 mg (0.697 mmol) 2-dicyclohexylphosphino-2',6'-dimethoxybiphenyl (SPhos) and 261 mg (0.116 mmol) palladium(II)acetate are added. The reaction mixture is stirred for 24 h at 100° C. 40 ml of a 1% sodium cyanide solution are added and the reaction mixture is refluxed for 1 h. The product (Cpd. A-1) is filtered off and is washed with water and ethanol.

1H NMR (300 MHz, THF-$d_8$, δ): 8.80-8.85 (m, 6H), 8.48-8.55 (m, 8H), 8.00-8.03 (m, 2H), 7.76 (t, J=5.8 Hz, 2H), 7.51-7.61 (m. 12H).

Example 2

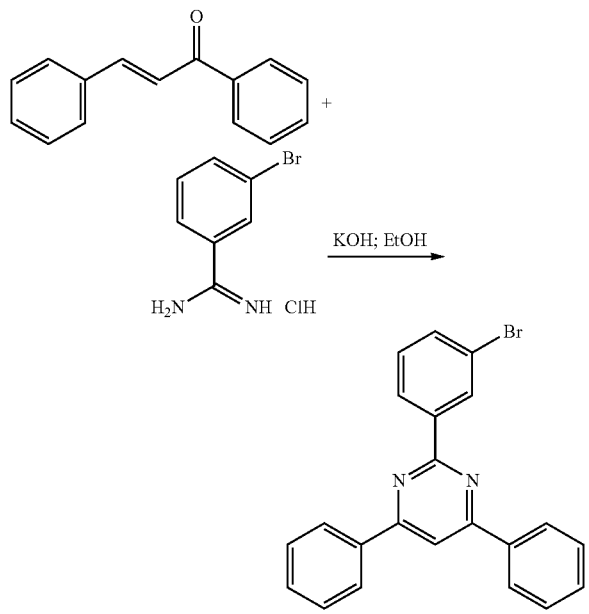

a) 2-(3-bromophenyl)-4,6-diphenyl-pyrimidine is synthesized as described in WO05085387A1.

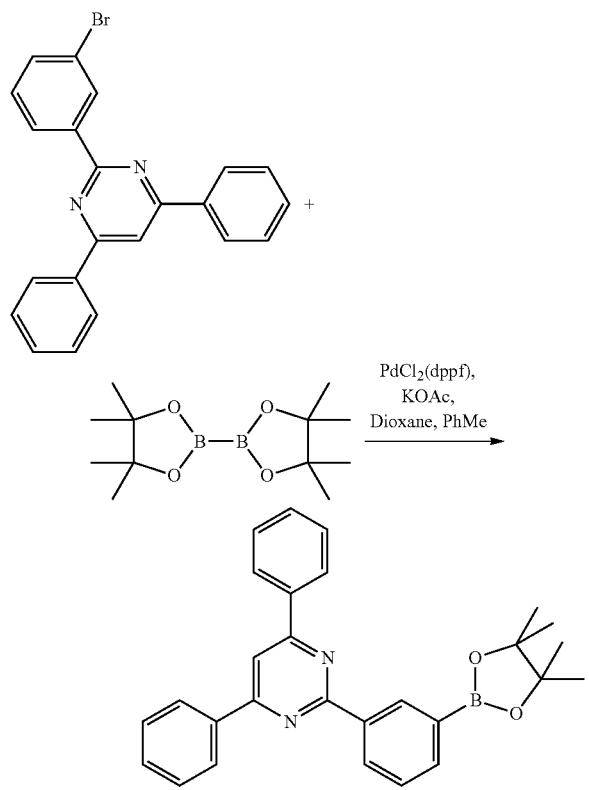

b) 6.00 g (15.5 mmol) 2-(3-bromophenyl)-4,6-diphenyl-pyrimidine, 9.44 g (37.2 mmol) 4,4,5,5-tetramethyl-2-(4,4,5, 5-tetramethyl-1,3,2-dioxaborolan-2-yl)-1,3,2-dioxaborolane, 7.60 g (77.5 mmol) potassium acetate are degassed with argon. 60 ml DMF and $PdCl_2$ (dppf) (1,1'-bis(diphenylphosphino)ferrocene-palladium(II)dichloride) are added. The reaction mixture is stirred at 60° C. for 28 h and is then poured onto ice. The water phase is extracted with diethyl ether. The organic phase is dried with magnesium sulfate and the solvent is distilled off. The product is used without purification in ste c).

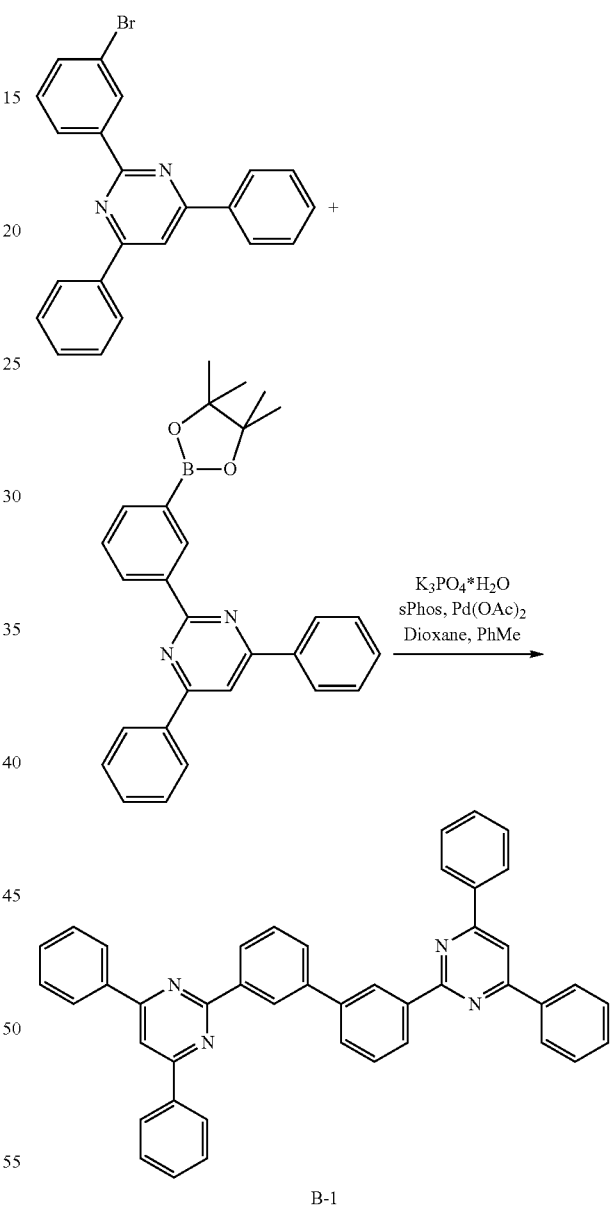

B-1 c) 3.50 g (8.06 mmol) of the product of example 2b), 2.31 g g (8.06 mmol) 4-(3-bromophenyl)-2,6-diphenyl-pyrimidine and 9.77 g (40.3 mmol) potassium phosphate tribasic monohydrate are degassed with argon. 30 ml dioxane, 70 ml toluene and 20 ml water are added. 199 mg (0.483 mmol) 2-dicyclohexylphosphino-2',6'-dimethoxybiphenyl (SPhos) and 18 mg (0.081 mmol) palladium(II)acetate are added. The reaction mixture is stirred for 24 h at 100° C. 40 ml of a 1% sodium cyanide solution are added and the reaction mixture is refluxed for 1 h. The product is filtered off and is washed with water and ethanol. Column chromatography on silica gel with toluene/ethyl acetate 19/1 results in compound B-1 (yield: 8%). MS (APCI (pos): m/z (%): 615 (M$^{+1}$, 100%).

$^1$H NMR (300 MHz, THF-d$_8$,): 9.29 (s, 2H), 8.90 (d, J=7.9 Hz, 2H), 8.54-8.58 (m, 8H), 8.46 (s, 2H), 8.04 (d, J=8.0 Hz, 2H), 7.78 (t, J=8.0 Hz, 2H), 7.60-7.62 (m, 12H).

Application Example 1

The ITO substrate used as the anode is first cleaned with commercial detergents for LCD production (Deconex® 20NS, and 25ORGAN-ACID® neutralizing agent) and then in an acetone/isopropanol mixture in an ultrasound bath. To eliminate any possible organic residues, the substrate is exposed to a continuous ozone flow in an ozone oven for a further 25 minutes. This treatment also improves the hole injection properties of the ITO. Then Plexcore® OC AJ20-1000 (commercially available from Plextronics Inc.) is spin-coated and dried to form a hole injection layer (~40 nm).

Thereafter, the organic materials specified below are applied by vapor deposition to the clean substrate at a rate of approx. 0.5-5 nm/min at about 10$^{-7}$-10$^{-9}$ mbar. As a hole transport and exciton blocker, Ir(dpbic)$_3$ (for preparation, see Ir complex (7) in the application WO 2005/019373) is applied to the substrate with a thickness of 20 nm, wherein the first 10 nm are doped with MoO$_x$ (~10%) to improve the conductivity.

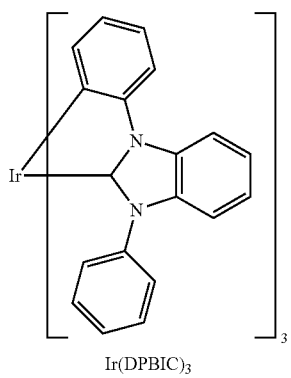
Ir(DPBIC)$_3$

Subsequently, a mixture of 30% by weight of compound

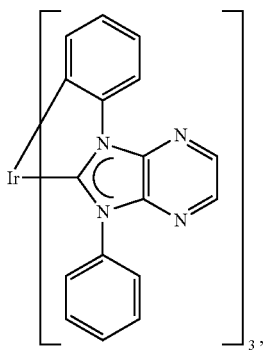

10% by weight of compound

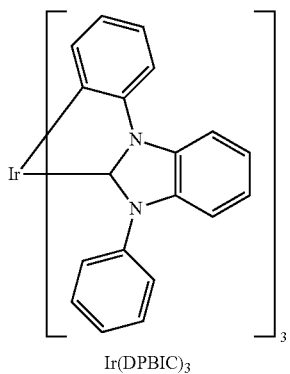
Ir(DPBIC)$_3$ and 60% by weight of compound

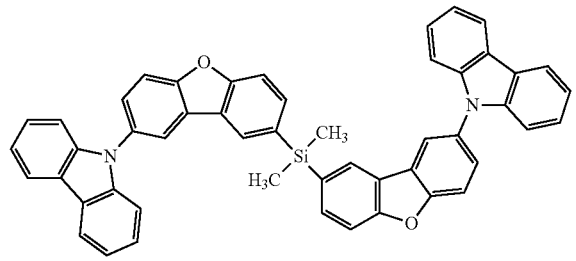 [SMILES: C[Si](C)(c1ccc2oc3ccc(-n4c5ccccc5c5ccccc54)cc3c2c1)c1ccc2oc3ccc(-n4c5ccccc5c5ccccc54)cc3c2c1]

(described in PCT/EP2009/067120) is applied by vapor deposition in a thickness of 20 nm.

Next, compound A-1 is applied as electron transport layer by vapor deposition in a thickness of 30 nm, as are a 2 nm-thick caesium fluoride layer (electron injection layer) and finally a 100 nm-thick Al electrode.

All prefabricated parts are sealed with a glass lid in an inert nitrogen atmosphere.

Comparative Application Example 1

Production and construction of an OLED as in the application example 1, except

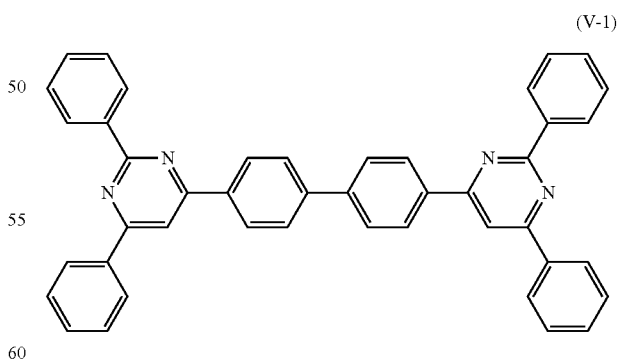
(V-1)

is used instead of compound A-1.

To characterize the OLED, electroluminescence spectra are recorded at various currents and voltages. In addition, the current-voltage characteristic is measured in combination with the light output emitted. The light output can be converted to photometric parameters by calibration with a photometer. To determine the lifetime, the OLED is operated at a constant current density and the decrease in the light output is recorded. The lifetime is defined as that time which lapses until the luminance decreases to half of the initial luminance.

|  | ETM | Voltage [V] | EQE[1] @ 300 nits | Lifetime[2] @ 4000 nits |
|---|---|---|---|---|
| Appl. Ex. 1 | Cpd. A-1 | 3.2 | 15.2% | 131 |
| Comp. Appl. Ex. 1 | Cpd. V-1 | 3.4 | 10.1% | 100 |

[1] External quantum efficiency (EQE) is # of generated photons escaped from a substance or a device/# of electrons flowing through it.
[2] The measured data of the Comparative Application Example is set to 100 and the data of the Application Examples is specified in relation to that of the Comparative Application Example.

The device of application example 1, where compound A-1 is used as electron transport material, shows a better external quantum efficiency and a better life time as the device of comparative application example 1, where the compound V-1 is used as electron transport material.

The invention claimed is:

1. A compound of the formula

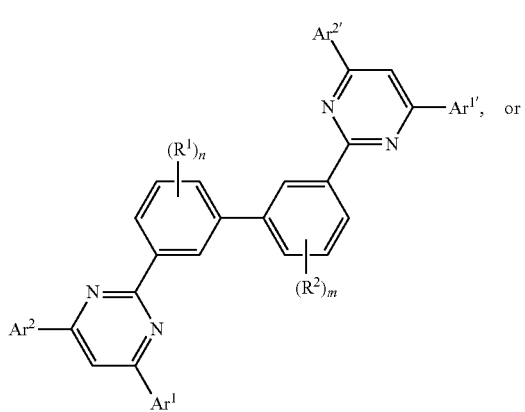

(I)

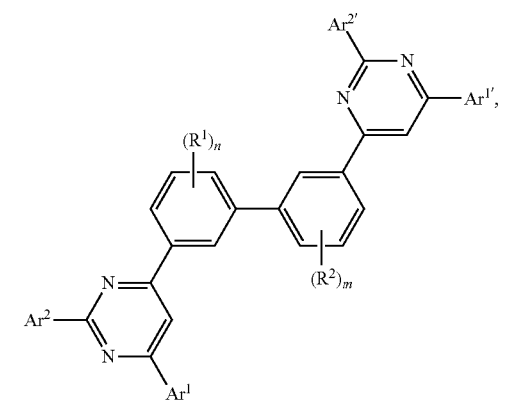

(II)

wherein
Ar$^1$, Ar$^2$, Ar$^{1'}$ and Ar$^{2'}$ are independently of each other a C$_6$-C$_{24}$aryl group, or a C$_2$-C$_{30}$heteroaryl group, which can optionally be substituted by G, a C$_4$-C$_{18}$cycloalkyl group, a C$_6$-C$_{10}$aryl group, a C$_6$-C$_{10}$aryl group which is substituted by a C$_1$-C$_8$alkyl group, a C$_2$-C$_5$heteroaryl group, or a C$_2$-C$_5$heteroaryl group, which is substituted by a C$_1$-C$_8$alkyl group,
R$^1$ and R$^2$ can be the same or different at each occurrence and are F, CN, NR$^{45}$R$^{45'}$, a C$_1$-C$_{25}$alkyl group, a C$_4$-C$_{18}$cycloalkyl group, a C$_1$-C$_{25}$alkoxy group which is substituted by E or interrupted by D, a C$_6$-C$_{24}$aryl group, a C$_6$-C$_{24}$aryl group which is substituted by G, a C$_2$-C$_{30}$heteroaryl group, a C$_2$-C$_{30}$heteroaryl group, which is substituted by G,
m and n are 0, 1, 2, 3, or 4,
D is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—,
E is —OR$^{69}$, —SR$^{69}$, —NR$^{65}$R$^{66}$, —COR$^{68}$, —COOR$^{67}$, —CONR$^{65}$R$^{66}$, —CN, or halogen,
G is E, or C$_1$-C$_{25}$alkyl,
R$^{45}$ and R$^{45'}$ are independently of each other a C$_1$-C$_{25}$alkyl group, a C$_4$-C$_{18}$cycloalkyl group, in which one or more carbon atoms which are not in neighborhood to each other could be replaced by —NR$^{45''}$—, —O—, —S—, —C(=O)—O—, or, —O—C(=O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^1$, and
R$^{45''}$ is a C$_1$-C$_{25}$alkyl group, or a C$_4$-C$_{18}$cycloalkyl group,
R$^{63}$ and R$^{64}$ are independently of each other H, C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—;
R$^{65}$ and R$^{66}$ are independently of each other C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—; or R$^{65}$ and R$^{66}$ together form a five or six membered ring, or ring system;
R$^{67}$ is C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—,
R$^{68}$ is H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—,
R$^{69}$ is C$_6$-C$_{18}$aryl; C$_6$-C$_{18}$aryl, which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—,
R$^{70}$ and R$^{71}$ are independently of each other C$_1$-C$_{18}$alkyl, C$_6$-C$_{18}$aryl, or C$_6$-C$_{18}$aryl, which is substituted by C$_1$-C$_{18}$alkyl, and
R$^{72}$ is C$_1$-C$_{18}$alkyl, C$_6$-C$_{18}$aryl, or C$_6$-C$_{18}$aryl, which is substituted by C$_1$-C$_{18}$alkyl.

2. The compound of formula II according to claim 1, which is a compound of formula

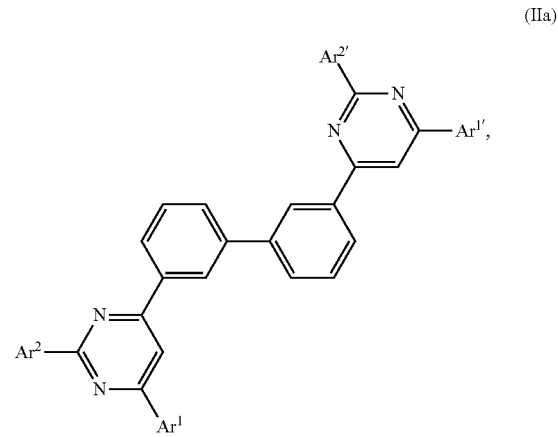

(IIa)

wherein Ar$^1$, Ar$^2$, Ar$^{1'}$ and Ar$^{2'}$ are as defined in claim 1.

3. The compound according to claim 2, wherein $Ar^1$, $Ar^2$, $Ar^{1'}$ and $Ar^{2'}$ are independently of each other selected from
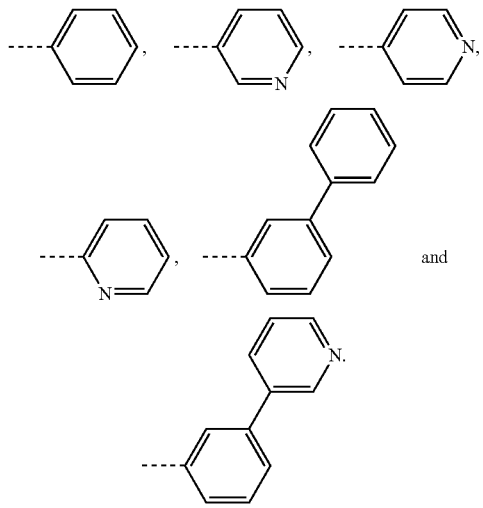
4. The compound according to claim 3:
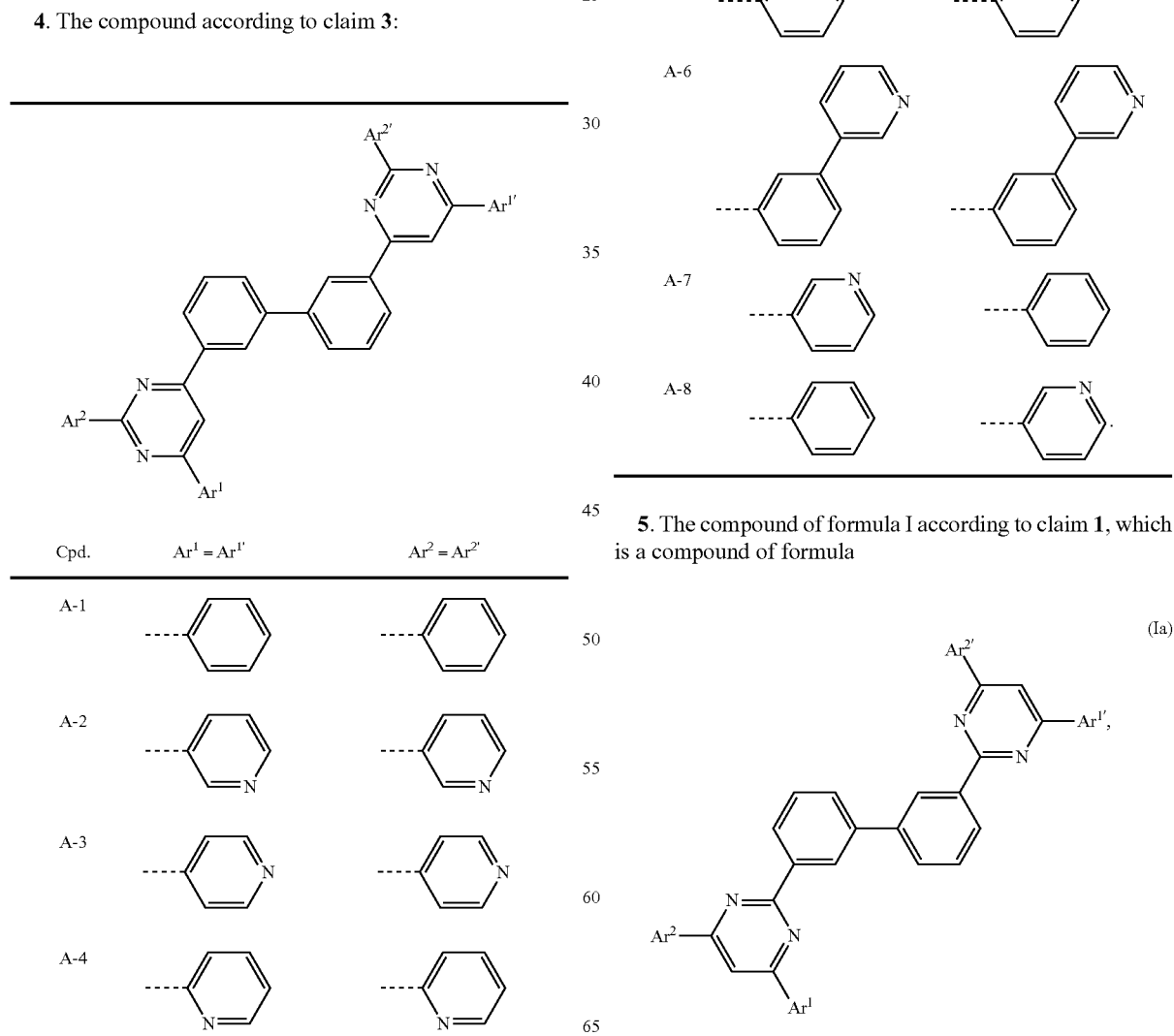
5. The compound of formula I according to claim 1, which is a compound of formula
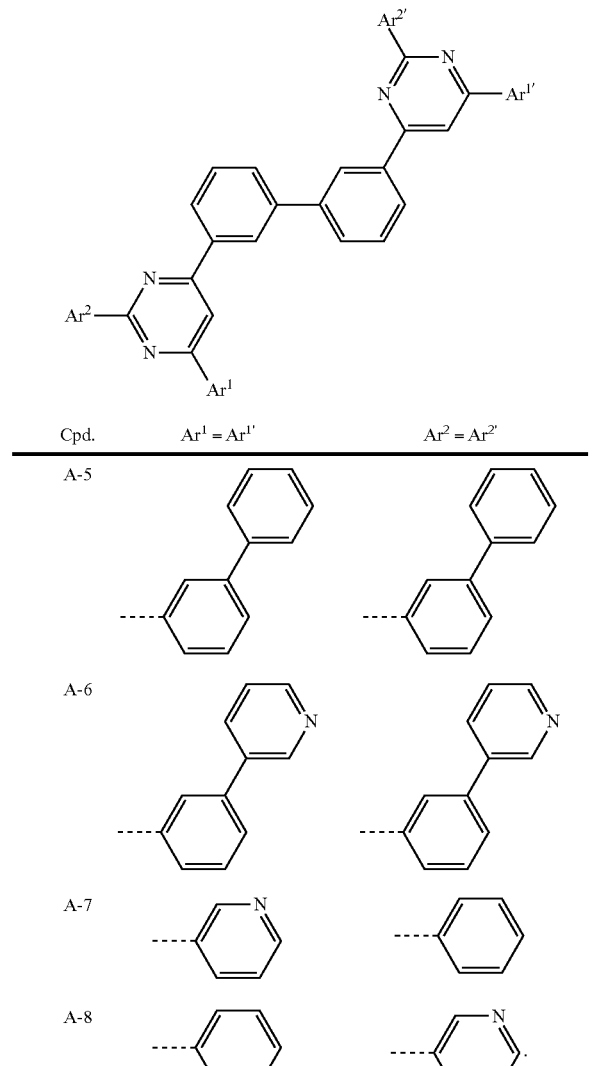
wherein $Ar^1$, $Ar^2$, $Ar^{1'}$ and $Ar^{2'}$ are as defined in claim 1.

6. The compound according to claim 5, wherein Ar¹, Ar², Ar¹' and Ar²' are independently of each other selected from

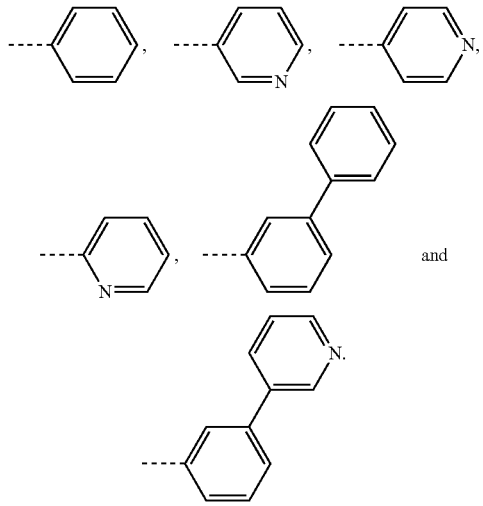

7. The compound according to claim 6:

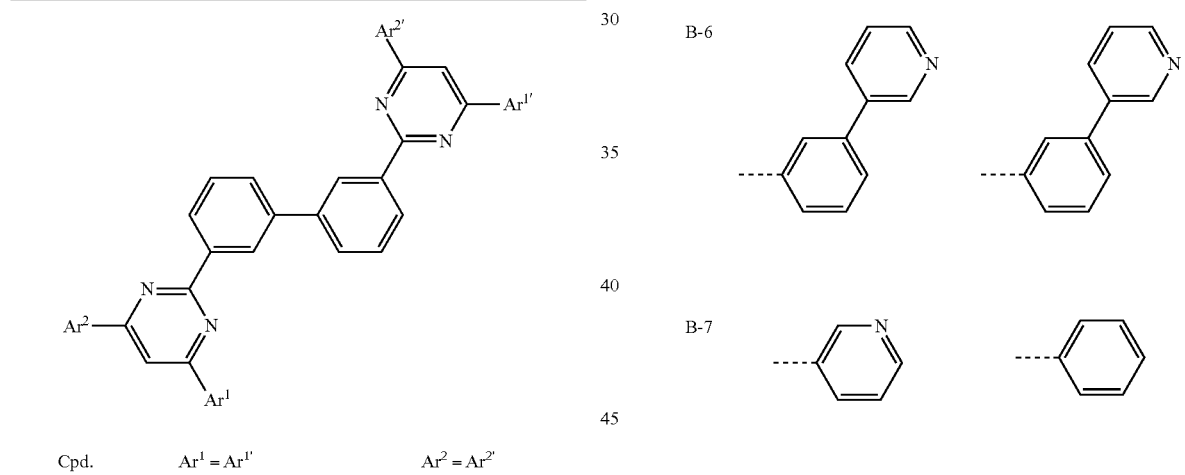

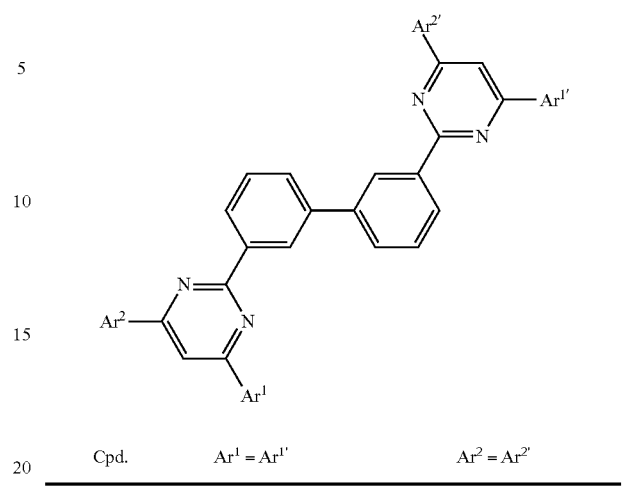

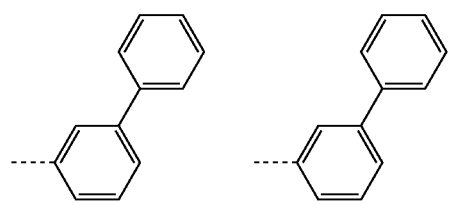

8. An electronic device, comprising a compound according to any of claims 1 to 7.

9. The electronic device according to claim 8, which is an electroluminescent device.

10. An electron transport layer, comprising a compound according to any of claims 1 to 7.

11. An apparatus selected from the group consisting of stationary visual display units, illuminations, information panels, and mobile visual display units comprising the organic electronic device according to claim 8.

12. A process for the preparation of compounds of the formula (I)

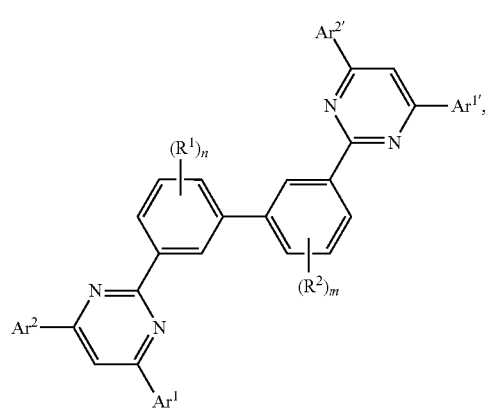

which comprises reacting a compound of formula (III)

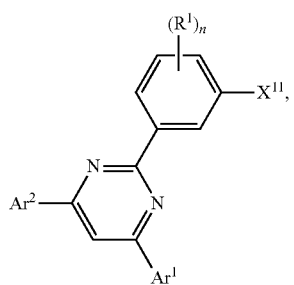

wherein $X^{11}$ stands for halogen, with a compound of formula (IV)

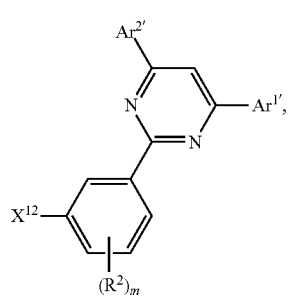

wherein $X^{12}$ is —B(OH)$_2$, —B(OY$^1$)$_2$,

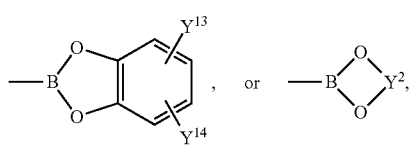

wherein $Y^1$ is independently in each occurrence a $C_1$-$C_{18}$alkyl group and $Y^2$ is independently in each occurrence a $C_2$-$C_{10}$alkylene group and $Y^{13}$ and $Y^{14}$ are independently of each other hydrogen, or a $C_1$-$C_{18}$alkyl group, in the presence of a base and a catalyst in a solvent, wherein Ar$^1$, Ar$^{1'}$, Ar$^2$, Ar$^{2'}$, m, n, R$^1$ and R$^2$ are as defined in claim 1.

13. A process for the preparation of compounds of the formula (II)

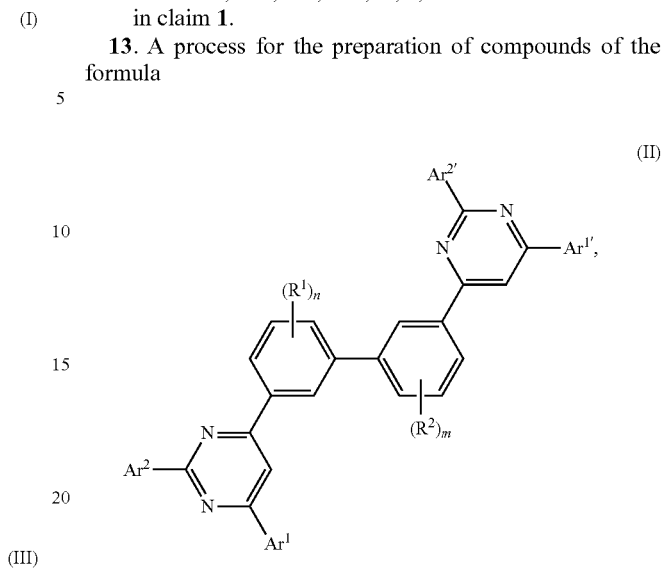

which comprises reacting a compound of formula (V)

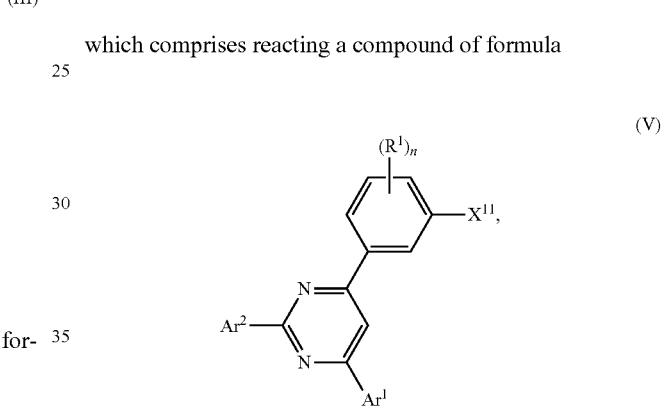

wherein $X^{11}$ stands for halogen, with a compound of formula (VI)

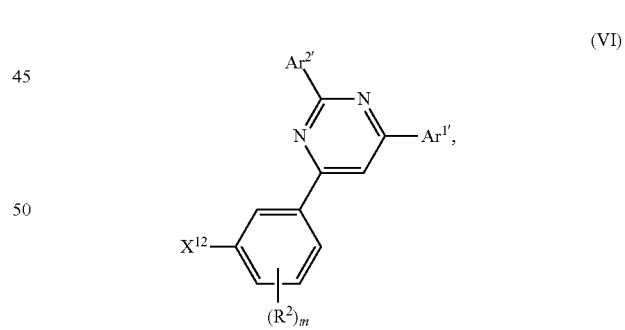

wherein $X^{12}$ is —B(OH)$_2$, —B(OY$^1$)$_2$,

, or 

wherein $Y^1$ is independently in each occurrence a $C_1$-$C_{18}$alkyl group and $Y^2$ is independently in each occurrence a $C_2$-$C_{10}$alkylene group, and $Y^{13}$ and $Y^{14}$ are independently of each other hydrogen, or a $C_1$-$C_{18}$alkyl group, in the presence of a base and a catalyst in a solvent, wherein $Ar^1$, $Ar^{1'}$, $Ar^2$, $Ar^{2'}$, m, n, $R^1$ and $R^2$ are as defined in claim 1.

14. The process according to claim 12, wherein $Y^2$ is $CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{18}$alkyl group.

15. The process according to claim 12, wherein $Y^2$ is —$C(CH_3)_2C(CH_3)_2$—, —$C(CH_3)_2CH_2C(CH_3)_2$— or —$CH_2C(CH_3)_2CH_2$—.

16. The process according to claim 13, wherein $Y^2$ is $CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{18}$alkyl group.

17. The process according to claim 13, wherein $Y^2$ is —$C(CH_3)_2C(CH_3)_2$—, —$C(CH_3)_2CH_2C(CH_3)_2$— or —$CH_2C(CH_3)_2CH_2$—.

18. The apparatus according to claim 11, wherein said apparatus is a stationary visual display unit selected from the group consisting of a visual display unit of a computer, a visual display unit of a television, a visual display unit of a printer, a kitchen appliance and an advertising panel.

19. The apparatus according to claim 11, wherein said apparatus is a mobile visual display unit selected from the group consisting of a cellphone visual display unit, a laptop visual display unit, a digital camera visual display unit, an MP3 player visual display unit, a bus vehicle and destination display, a train vehicle and destination display, an illumination unit; a keyboard; an item of clothing; furniture and wallpaper.

* * * * *